(12) United States Patent
Gallop et al.

(10) Patent No.: US 7,144,877 B2
(45) Date of Patent: Dec. 5, 2006

(54) BILE-ACID DERIVED COMPOUNDS FOR ENHANCING ORAL ABSORPTION AND SYSTEMIC BIOAVAILABILITY OF DRUGS

(75) Inventors: Mark A. Gallop, Los Altos, CA (US); Kenneth C. Cundy, Redwood City, CA (US)

(73) Assignee: XenoPort, Inc., Santa Clara, CA (US)

( * ) Notice: Subject to any disclaimer, the term of this patent is extended or adjusted under 35 U.S.C. 154(b) by 421 days.

(21) Appl. No.: 09/972,411

(22) Filed: Oct. 5, 2001

(65) Prior Publication Data

US 2002/0099041 A1 Jul. 25, 2002

Related U.S. Application Data

(60) Provisional application No. 60/238,758, filed on Oct. 6, 2000.

(51) Int. Cl.
- *A61K 31/56* (2006.01)
- *C07J 9/00* (2006.01)
- *C07J 31/00* (2006.01)
- *C07J 41/00* (2006.01)

(52) U.S. Cl. .................. 514/182; 552/548; 552/550; 552/551

(58) Field of Classification Search ............... 552/548, 552/550, 551; 514/182
See application file for complete search history.

(56) References Cited

U.S. PATENT DOCUMENTS

| | | | |
|---|---|---|---|
| 3,326,758 A | 6/1967 | Irmscher et al. | |
| 4,560,512 A | 12/1985 | Firestone | |
| 5,352,682 A | 10/1994 | Sipos | |
| 5,462,933 A | 10/1995 | Kramer et al. | |
| 5,646,272 A | 7/1997 | Kramer et al. | |
| 5,668,126 A | 9/1997 | Kramer et al. | |
| 5,695,738 A | 12/1997 | Anderson et al. | |
| 5,725,840 A | 3/1998 | Klaveness et al. | |
| 5,942,248 A | 8/1999 | Barnwell | |
| 6,143,738 A | 11/2000 | Zasloff | |
| 6,288,041 B1 | 9/2001 | Chaki et al. | |

FOREIGN PATENT DOCUMENTS

| | | | |
|---|---|---|---|
| JP | 04059792 | * | 2/1992 |
| JP | 11-60594 | | 3/1999 |
| WO | WO 94/29336 | | 12/1994 |
| WO | WO 99/41275 | | 8/1999 |
| WO | WO 01/09163 A2 | | 2/2001 |
| WO | WO 01/76531 A2 | | 10/2001 |
| WO | WO 02/32376 A2 | | 4/2002 |
| WO | 02/100347 | | 12/2002 |

OTHER PUBLICATIONS

Database esp@cenet on STN, PN KR9701149 (Kim Young-Man et al.), Jan. 29, 1997, Abstract only.

Swaan et al., Preface. Advanced Drug Delivery Reviews. 1996, vol. 20, pp. 1-3.

Russell-Jones et al., "Vitamin B12 Mediated Oral Delivery Systems for Granulocyte-Colony Stimulating Factor and Erythropoietin," *Bioconjugate Chemistry*, 1995, vol. 6, pp. 459-465.

Shah et al., "Transcellular Delivery of an Insulin-Transferrin Conjugate in Enterocyte-like Caco-2 Cells," *J. of Pharm. Sci.*, Dec. 1996, vol. 85, No. 12, pp. 1306-1311.

International Search Report mailed Jan. 22, 2002 from PCT/US01/42513.

International Search Report mailed Jan. 23, 2002 from PCT/US01/31486.

International Search Report mailed Dec. 31, 2001 from PCT/US01/31394.

European Search Report from EP 01 98 9083 dated May 25, 2005.

Kramer et al., "Modified Bile Acid as Carriers for Peptides and Drugs", Journal of Controlled Release, vol. 46, (1997), Amsterdam, NL, pp. 17-30.

Lee et al., "Pharmacogenomics of Drug Transporters: The Next Drug Delivery Challenge", Advanced Drug Delivery Reviews, vol. 50, (2001), pp. S33-S40.

European Search Report dated May 26, 2005.

Anelli et al., *Synth. Commun.* 1998, 28, pp. 109-117.

Baringhaus, K.H., et al., Substrate specificity of the ileal and hepatic $Na^+$ / bile acid cotransporters of the rabbit. II. A reliable 3D QSAR pharmacophore model for the ileal Na/bile acid cotransporter, *J. Lipid Res.* 1999, 40, pp. 2158-2168.

Batta, et al., *J. Lipid. Res.* 1991, 32, 977-983.

Bundgaard, H., in *Design of Prodrugs* (Bundgaard, H. Ed.), Elsevier Science B.V., 1985, pp. 1-92.

Bundgaard, H., et al., Esters of N, N-disubstituted 2-hydroxyacetamides as a novel highly biolabile prodrug type for carboxylic acids, *J. Med. Chem.*, 1987, 30, pp. 451-454. Copy needed.

Ho, N. F. H., Utilizing bile acid carrier mechanisms to enhance liver and small intestine absorption, *Ann. N. Y. Acad. Sci.*, 1987, 507, pp. 315-329.

Kagedahl, M., et al., Use of the intestinal bile acid transporter for the uptake of cholic acid conjugates with HIV-1 protease inhibitory activity, *Pharm. Res.*, 1997., 14, pp. 176-180.

Kim, D.C., et al., Evaluation of bile acid transporter in enhancing intestinal permeability of renin-inhibitory peptides, *J. Drug Targeting*, 1993, 1, pp. 347-359.

Kramer, W., et al., Liver-specific drug targeting by coupling to bile acids, *J. Biol. Chem.*, 1992, 267, pp. 18598-18604.

(Continued)

*Primary Examiner*—Barbara P. Badio
(74) *Attorney, Agent, or Firm*—Buchanan Ingersoll & Rooney PC

(57) ABSTRACT

Disclosed are methods for providing enhanced systemic blood concentrations of orally delivered drugs that are incompletely translocated across the intestinal wall of an animal. Also disclosed are methods for the sustained release of drugs, whether poorly or readily bioavailable via oral delivery to animals. Still further, disclosed are compounds and pharmaceutical compositions that are used in such methods.

4 Claims, 26 Drawing Sheets

OTHER PUBLICATIONS

Kramer, W., et al.,. Intestinal absorbtion of peptides by coupling to bile acids, *J. Biol. Chem.*, 1994a, 269, pp. 10621-10627.

Kramer, W., et al., Bile acid derived HMG-CoA reductase inhibitors, *Biochim. Biophys. Acta*, 1994b, 1227, 137-154.

Kramer, W., et al., Substrate specificity of the ileal and hepatic $Na^+$/bile acid cotransporters of the rabbit. I. Transport studies with membrane vesicles and cell lines expressing the cloned transporters, *J. Lipid Res.* 1999, 40, pp. 1604-1617.

Kullak-Ublick, G.A., et al., Hepatobiliary transport, *J. Hepatology* 2000, 32 (Suppl. 1), pp. 3-18.

Navia, M.A., et al., Design principles for orally bioavailable drugs, *Drug Discovery Today*, 1996, 7, pp. 179-189.

Petzinger, E., et al., Hepatobiliary transport of hepatic 3-hydroxy-3-methylglutaryl coenzyme. A reductase inhibitors conjugated with bile acids, *Hepatology* 1995, 22, pp. 1801-1811.

Swaan, P.W., et al., Use of the intestinal and hepatic bile acid transporters for drug delivery, *Adv. Drug Delivery Rev.*, 1996, 20, pp. 59-82.

Tsuji, A., et al., Carrier-mediated intestinal transport of drugs, *Pharm. Res.*, 1996, 13, pp. 963-977.

\* cited by examiner

*The Enterohepatic Circulation with Key Transporter Proteins Mediating Bile Acid Circulation*

*Bile Acid Conjugates of HMG-CoA Reductase Inhibitor*

R=OH S 3554
R=NHCH$_2$CO$_2$H S 3898
R=NHCH$_2$CH$_2$SO$_3$H S 4193

Prodrugs Based on 3-Substituted Bile Acid Derivatives

Variables
(A) Bile Acid Moiety
(B) Steroid Linkage Chemistry
(C) Linker Moiety
(D) Drug Linkage Chemistry (A) Bile Acid Moiety (Other-2)

13a. R=OH  12-oxocholate
b. R=NH-CH₂CH₂-SO₃H  12-oxotaurocholate
c. R=NH-CH₂-CO₂H  12-oxoglycocholate

FIG. 4A
(A) Bile Acid Moiety (Preferred)

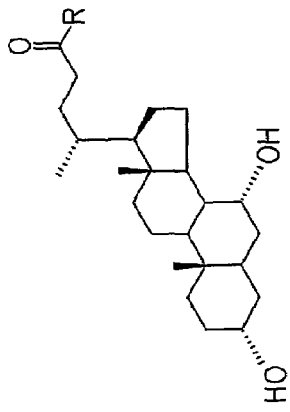

3a. R=OH chenodeoxycholate
b. R=N—SO₃H taurochenodeoxycholate
c. R=N—CO₂H glycochenodeoxycholate

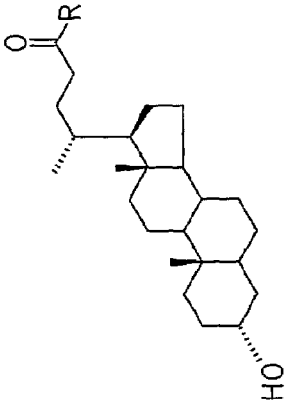

6a. R=OH lithocholate
b. R=N—SO₃H taurolithocholate
c. R=N—CO₂H glycolithocholate

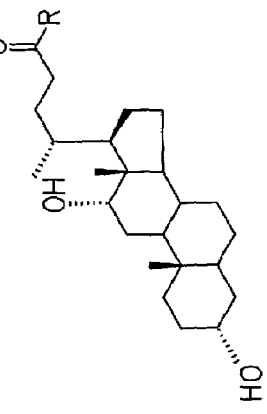

2a. R=OH deoxycholate
b. R=N—SO₃H taurodeoxycholate
c. R=N—CO₂H glycodeoxycholate

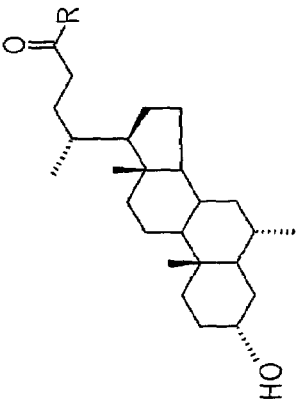

5a. R=OH hyodeoxycholate
b. R=N—SO₃H taurohyodeoxycholate
c. R=N—CO₂H glycohyodeoxycholate

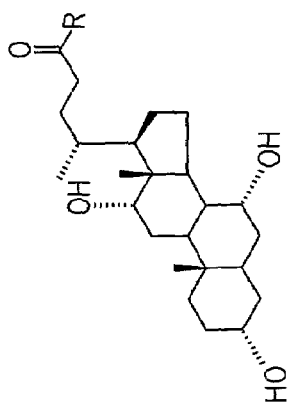

1a. R=OH cholate
b. R=N—SO₃H taurocholate
c. R=N—CO₂H glycocholate

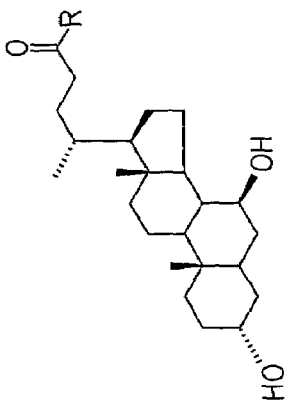

4a. R=OH ursodeoxycholate
b. R=N—SO₃H tauroursodeoxycholate
c. R=N—CO₂H glycoursodeoxycholate

FIG. 4B
(A) Bile Acid Moiety (Other-1)

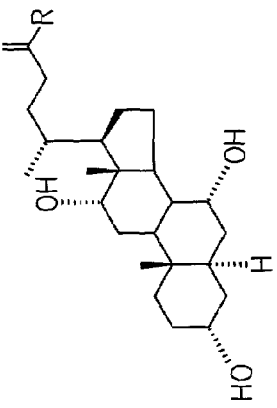

7a. R=OH ursocholate
b. R=NH-CH₂-CH₂-SO₃H tauroursocholate
c. R=NH-CH₂-CH₂-CO₂H glycoursocholate

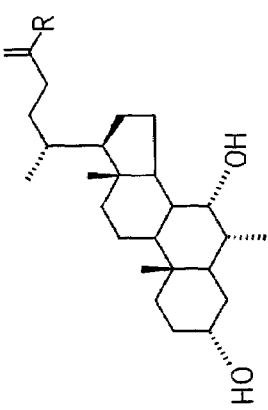

8a. R=OH hyocholate
b. R=NH-CH₂-CH₂-SO₃H taurohyocholate
c. R=NH-CH₂-CH₂-CO₂H glycohyocholate

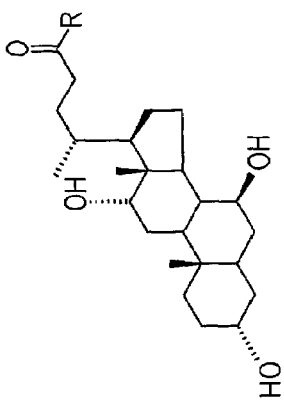

9a. R=OH allocholate
b. R=NH-CH₂-CH₂-SO₃H tauroallocholate
c. R=NH-CH₂-CH₂-CO₂H glycoallocholate

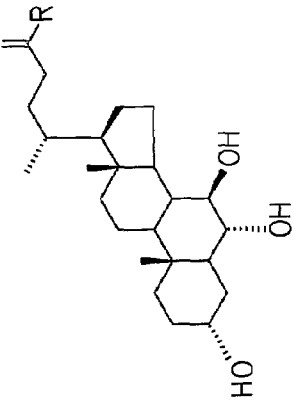

10a. R=OH α-muricholate
b. R=NH-CH₂-CH₂-SO₃H α-muritaurocholate
c. R=NH-CH₂-CH₂-CO₂H α-muriglycocholate

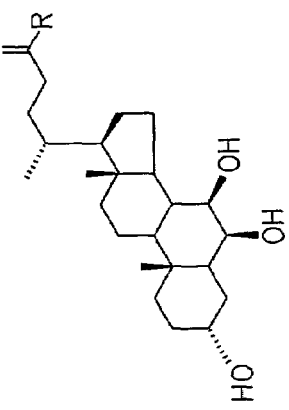

11a. R=OH β-muricholate
b. R=NH-CH₂-CH₂-SO₃H β-muritaurocholate
c. R=NH-CH₂-CH₂-CO₂H β-muriglycocholate

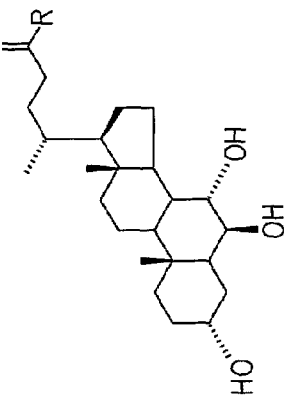

12a. R=OH ω-muricholate
b. R=NH-CH₂-CH₂-SO₃H ω-muritaurocholate
c. R=NH-CH₂-CH₂-CO₂H ω-muriglycocholate (B) Steroid Linkage Chemistry "Z-BA"
1. 3-Hydroxy-Derived Linkages
Both 3α- and 3β- Isomers are Implied a. Ether  b. Ester  c. Carbonate  d. Carbamate e. Phosphate  f. Phosphonate  g. Phosphoramidate (B) Steroid Linkage Chemistry "Z-BA"
2. 3-Amino-Derived Linkages
Both 3α- and 3β- Isomers are Implied a. Amine  b. Amide  c. Carbamate  d. Urea e. Thiourea  f. Sulfonamide  g. Phosphoramidate

FIG. 5C (B) Steroid Linkage Chemistry "Z-BA"
3. 3-Thiol-Derived Linkages
Both 3α- and 3β- Isomers are Implied

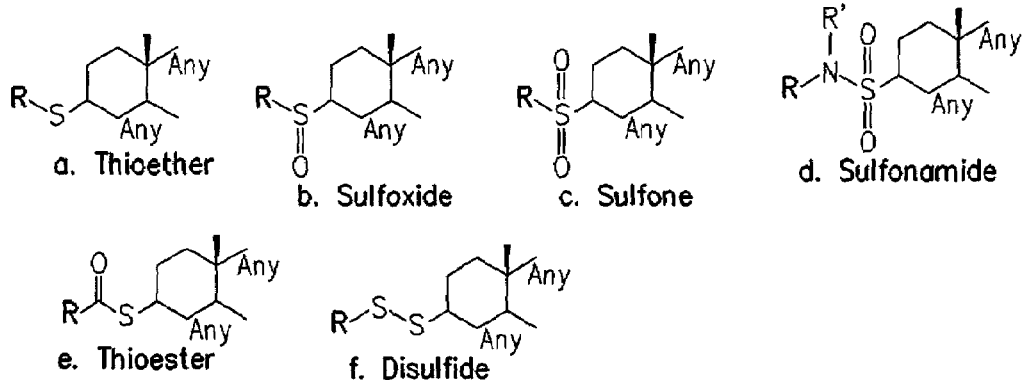

a. Thioether
b. Sulfoxide
c. Sulfone
d. Sulfonamide
e. Thioester
f. Disulfide

FIG. 5D (B) Steroid Linkage Chemistry "Z-BA"
4. 3-Keto-Derived Linkages

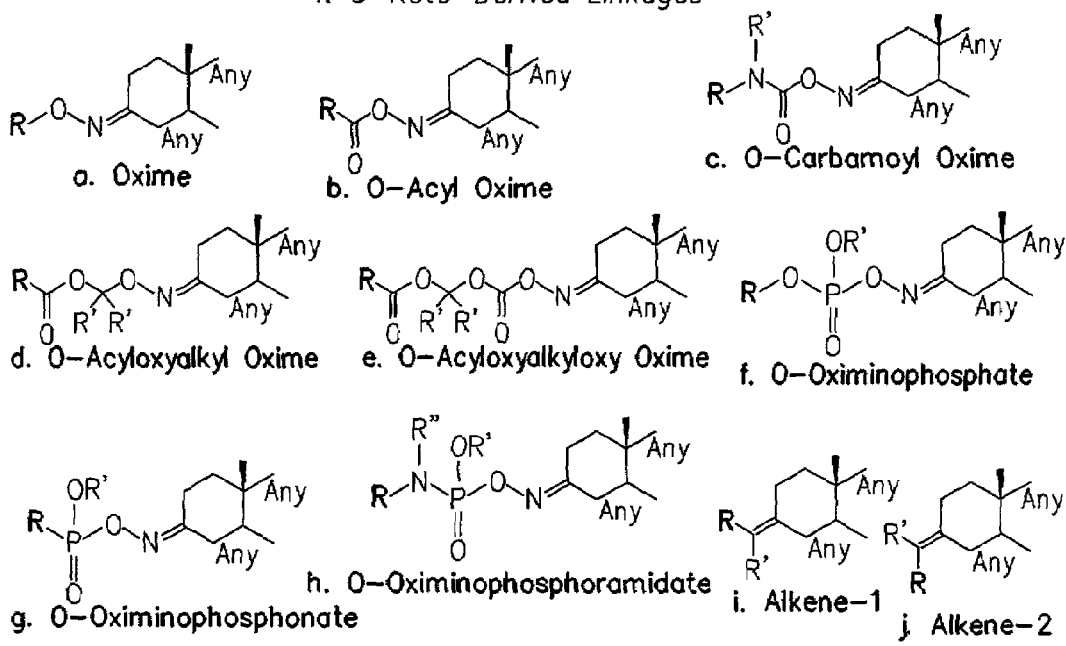

a. Oxime
b. O-Acyl Oxime
c. O-Carbamoyl Oxime
d. O-Acyloxyalkyl Oxime
e. O-Acyloxyalkyloxy Oxime
f. O-Oximinophosphate
g. O-Oximinophosphonate
h. O-Oximinophosphoramidate
i. Alkene-1
j. Alkene-2

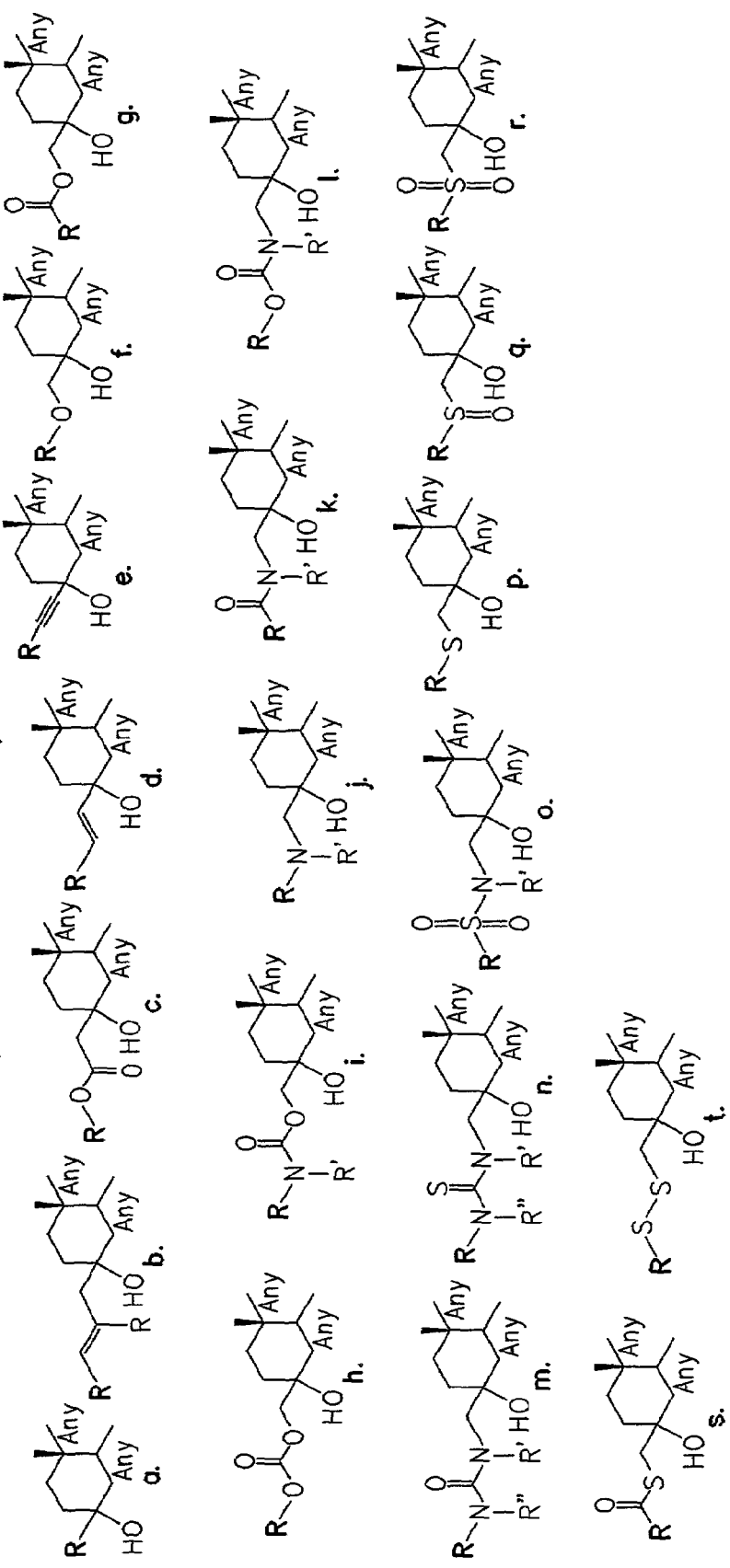
FIG. 5E (B) Steroid Linkage Chemistry "Z-BA"
5. 3,3-Disubstituted Hydroxy Linkages
Both 3α-OH and 3β-OH Isomers are Implied

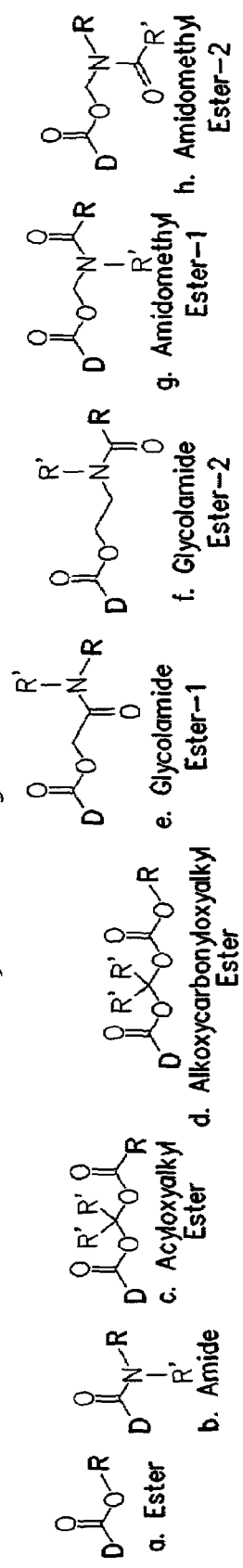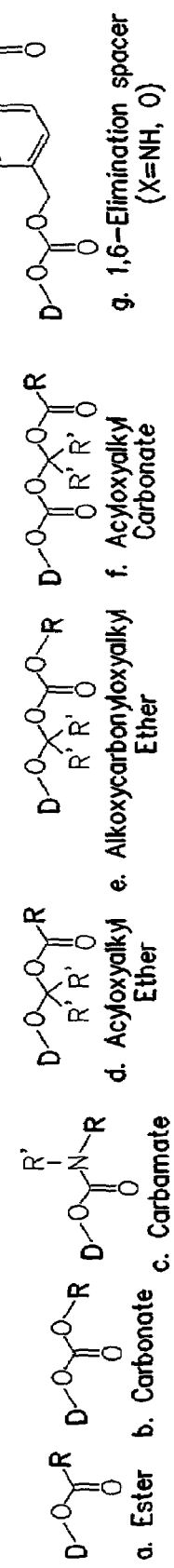
FIG. 7A (D) Drug Linkage Chemistry "DRUG-X-"
1. Carboxylic Acid Drugs
FIG. 7B (D) Drug Linkage Chemistry "DRUG-X-"
2. Alcohol Drugs

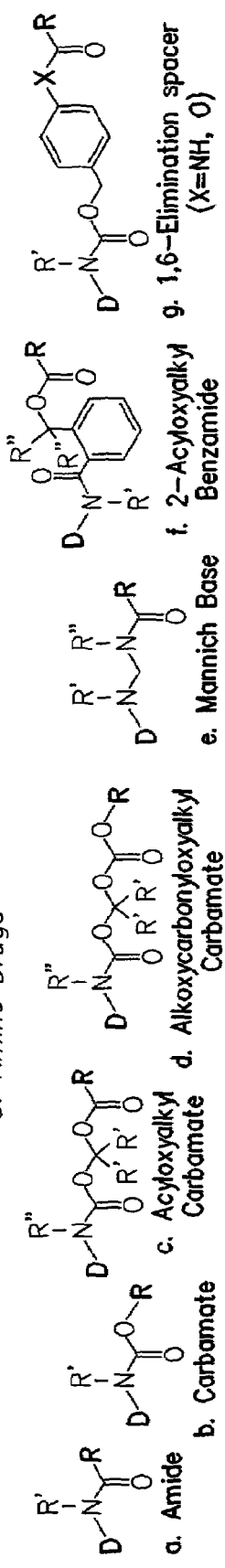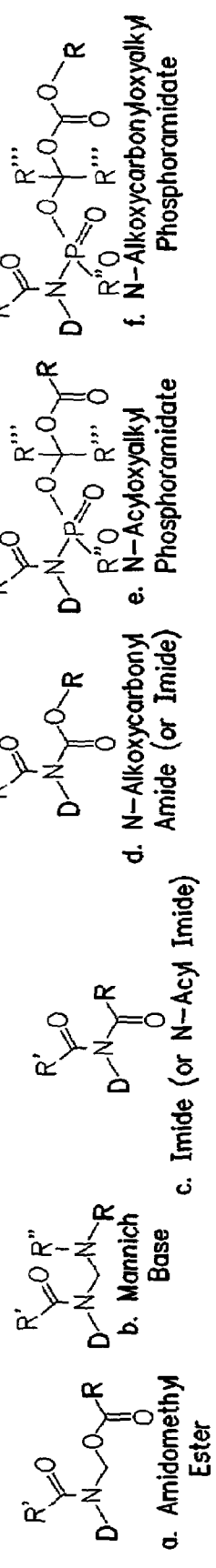
FIG. 7C (D) Drug Linkage Chemistry "DRUG—X—" 3. Amine Drugs
FIG. 7D (D) Drug Linkage Chemistry "DRUG—X—" 4. Amide or Imide Drugs

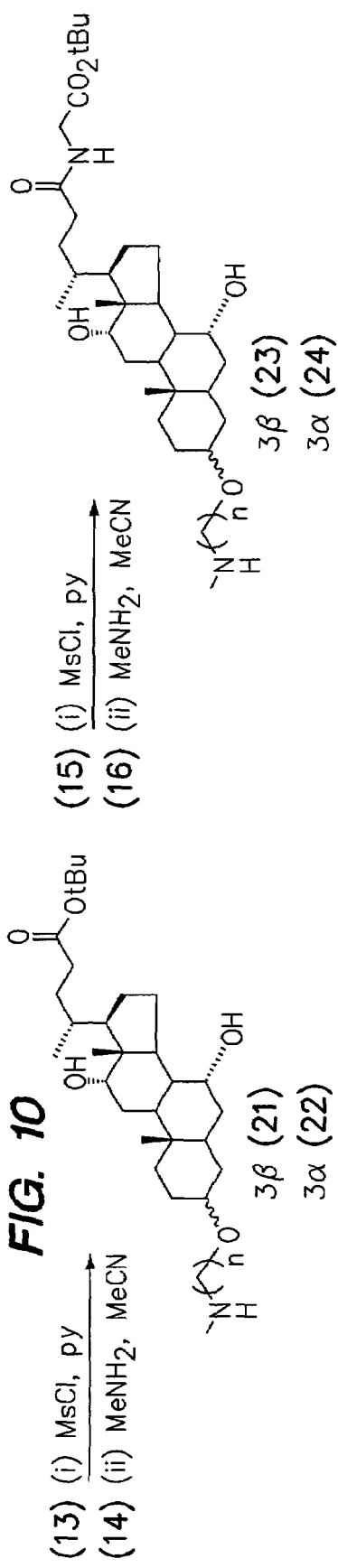
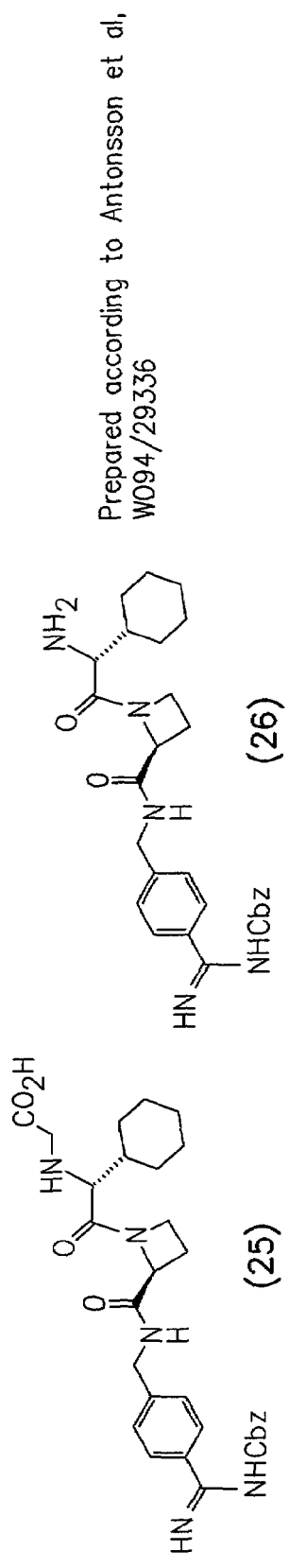
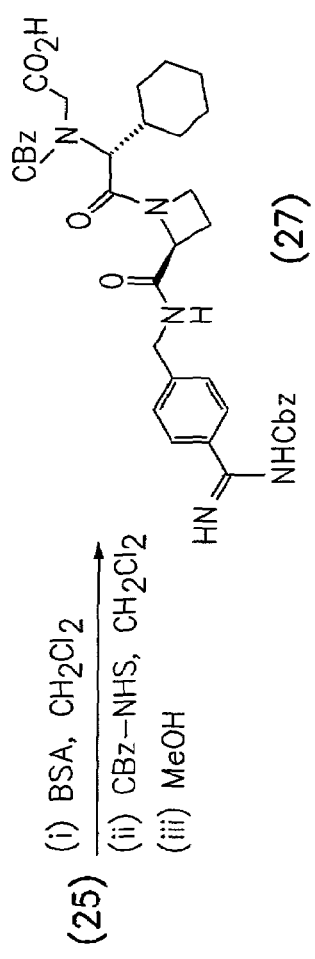
FIG. 10

FIG. 11
(13) (i) Chloromethyl chloroformate CH₂Cl₂, py
(14) (ii) NaI, MeCN
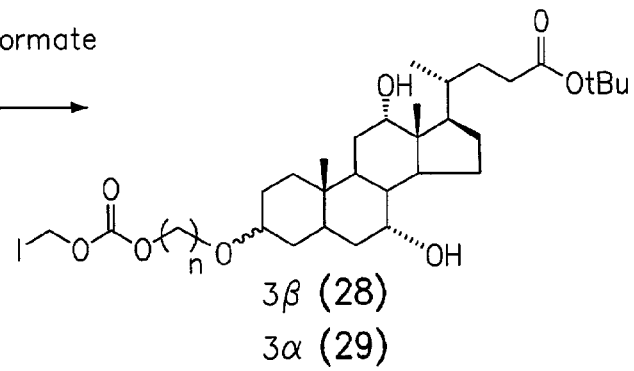
3β (28)
3α (29)
(15) (i) Chloromethyl chloroformate CH₂Cl₂, py
(16) (ii) NaI, MeCN
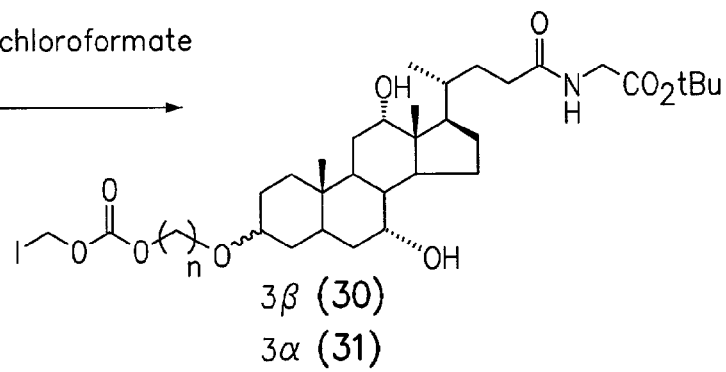
3β (30)
3α (31)
(17) (i) BSA, CH₂Cl₂
(18) (ii) Chloroiodomethane CH₂Cl₂
(iii) NaI, MeCN
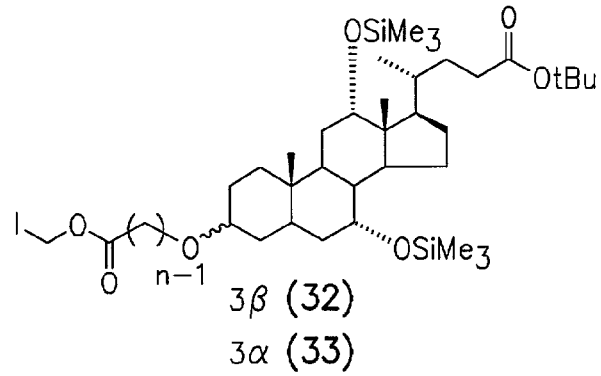
3β (32)
3α (33)
(19) (i) BSA, CH₂Cl₂
(20) (ii) Chloroiodomethane CH₂Cl₂
(iii) NaI, MeCN
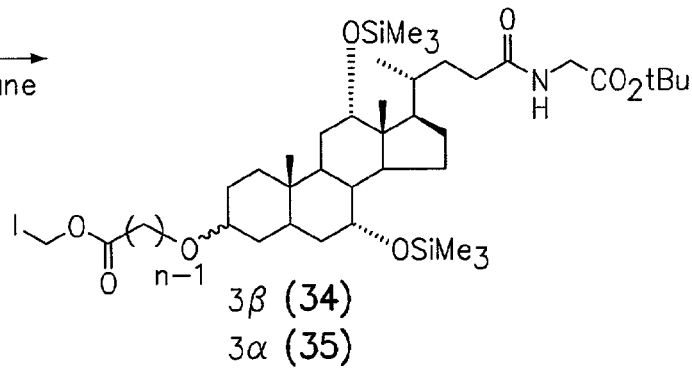
3β (34)
3α (35)

FIG. 13
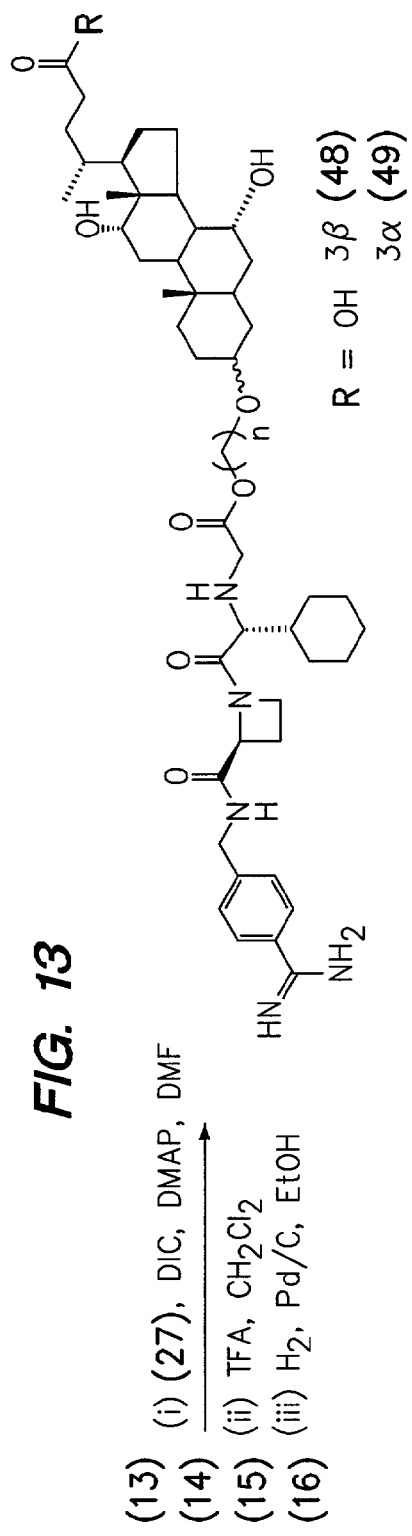
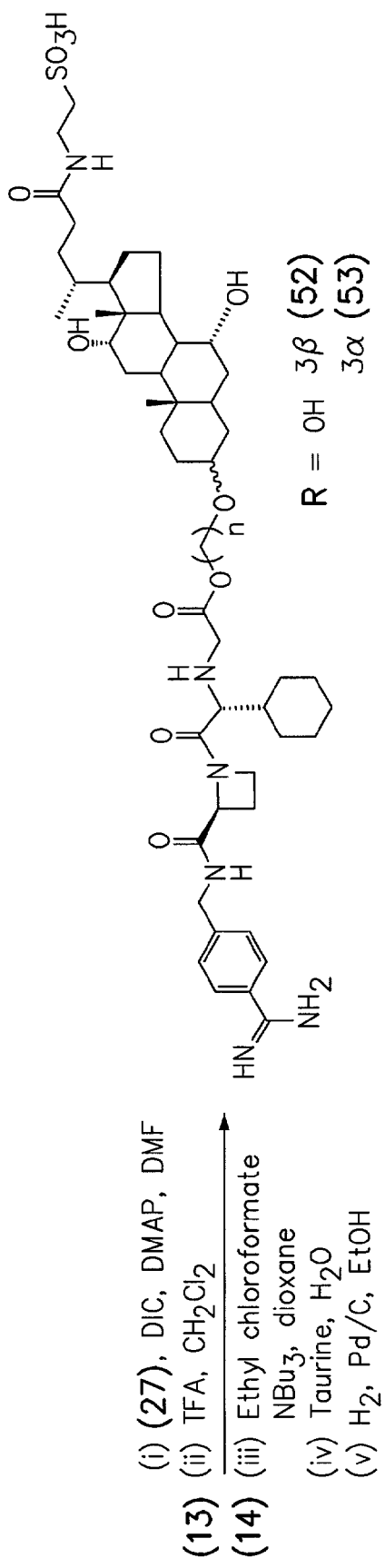
(13) (14) → (i) (27), DIC, DMAP, DMF
(ii) TFA, CH₂Cl₂
(iii) H₂, Pd/C, EtOH
→ (15) (16)
R = OH  3β (48)
          3α (49)
R = NHCH₂CO₂H  3β (50)
                3α (51)
(13) (14) → (i) (27), DIC, DMAP, DMF
(ii) TFA, CH₂Cl₂
(iii) Ethyl chloroformate, NBu₃, dioxane
(iv) Taurine, H₂O
(v) H₂, Pd/C, EtOH
R = OH  3β (52)
          3α (53)

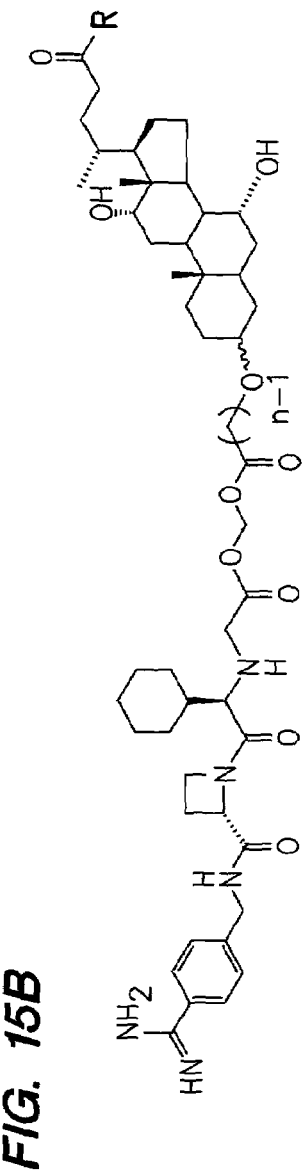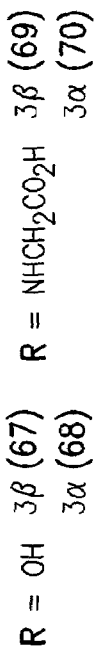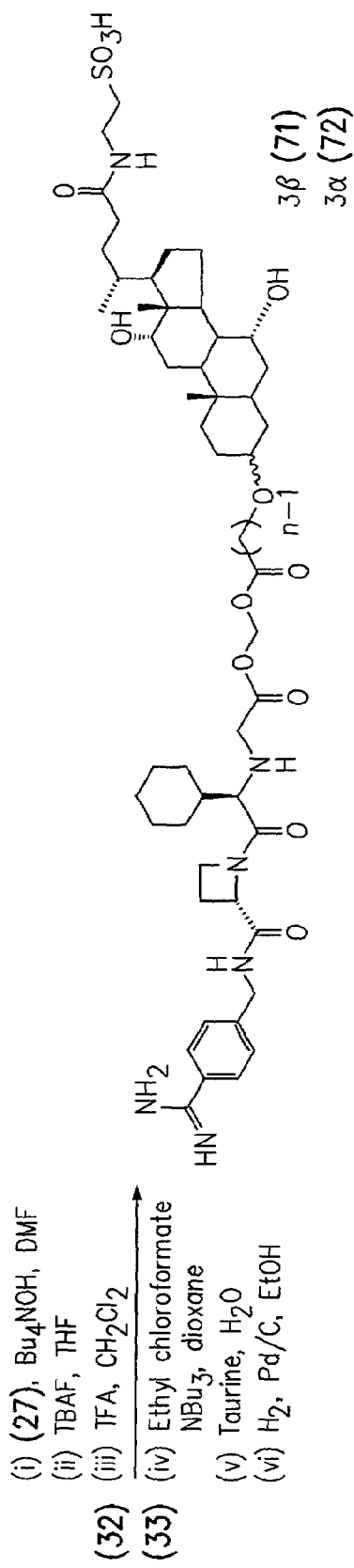
FIG. 15B

BILE-ACID DERIVED COMPOUNDS FOR ENHANCING ORAL ABSORPTION AND SYSTEMIC BIOAVAILABILITY OF DRUGS

CROSS-REFERENCE TO RELATED APPLICATIONS

This application claims the benefit of U.S. Provisional Application Ser. No. 60/238,758, which was filed on Oct. 6, 2000, the disclosure of which is incorporated by reference in its entirety.

References

The following publications, patents and patent applications are cited in this application as superscript numbers

[1] Anelli et al., Synth. Commun. 1998, 28, 109–117.
[2] Antonsson, et al., Intl. Patent Application Publication No. WO 94/29336)
[3] Baringhaus, K.-H.; Matter, H.; Stengelin, S.; Kramer, W. Substrate specificity of the ileal and hepatic Na$^+$/bile acid cotransporters of the rabbit. II. A reliable 3D QSAR pharmacophore model for the ileal Na/bile acid cotransporter. J. Lipid Res. 1999, 40, 2158–2168.
[4] Batta, et al., J. Lipid. Res. 1991, 32, 977–983
[5] Bundgaard, H. in Design of Prodrugs (Bundgaard, H. Ed.), Elsevier Science B. V., 1985, pp. 1–92.
[6] Bundgaard, H.; Nielsen, N. M. Esters of N, N-disubstituted 2-hydroxyacetamides as a novel highly biolabile prodrug type for carboxylic acids. J. Med. Chem. 1987, 30, 451–454.
[7] Ho, N. F. H. Utilizing bile acid carrier mechanisms to enhance liver and small intestine absorption. Ann. N. Y. Acad. Sci. 1987, 507, 315–329.
[8] Johansson, et al., Intl. Patent Application Pubication No. WO 99/41275.
[9] Kagedahl, M.; Swaan, P. W.; Redemann, C. T.; Tang, M.; Craik, C. S.; Szoka, F. C.; Oie, S. Use of the intestinal bile acid transporter for the uptake of cholic acid conjugates with HIV-1 protease inhibitory activity. Pharm. Res. 1997, 14, 176–180.
[10] Kim, D.-C.; Harrison, A. W.; Ruwart, M. J.; Wilkinson, K. F.; Fisher, J. F.; Hidalgo, 1. J.; Borchardt, R. T. Evaluation of bile acid transporter in enhancing intestinal permeability of renin-inhibitory peptides. J. Drug Targeting 1993, 1, 347–359.
[11] Kramer, W.; Wess, G.; Schubert, G.; Bickel, M.; Girbig, F.; Gutjahr, U.; Kowalewski, S.; Baringhaus, K.-H.; Enhsen, A.; Glombik, H.; Mullner, S.; Neckermann, G.; Schulz, S.; Petzinger, E. Liver-specific drug targeting by coupling to bile acids. J. Biol. Chem. 1992, 267, 18598–18604.
[12] Kramer, W.; Wess, G.; Neckermann, G.; Schubert, G.; Fink, J.; Girbig, F.; Gutjahr, U.; Kowalewski, S.; Baringhaus, K.-H.; Boger, G.; Enhsen, A.; Falk, E.; Friedrich, M.; Glombik, H.; Hoffmann, A.; Pittius, C.; Urmann, M. Intestinal absorption of peptides by coupling to bile acids. J. Biol. Chem. 1994a, 269, 10621–10627.
[13] Kramer, W.; Wess, G.; Enhsen, A.; Bock, K.; Falk, E.; Hoffmann, A.; Neckerman, G.; Gantz, D.; Schulz, S.; Nickau, L.; Petzinger, E.; Turley, S.; Dietschy, J. M. Bile acid derived HMG—CoA reductase inhibitors. Biochim. Biophys. Acta 1994b, 1227, 137–154.
[14] Kramer, W.; Wess, G. Modified bile acid conjugates, and their use as pharmaceuticals. U.S. Pat. No. 5,462, 933, 1995.
[15] Kramer, W.; Wess, G. Bile acid conjugates of proline hydroxylase inhibitors. U.S. Pat. No. 5,646,272, 1997a.
[16] Kramer, W.; Wess, G. Bile acid derivatives, processes for their preparation, and use as pharmaceuticals. U.S. Pat. No. 5,668,126, 1997b.
[17] Kramer, W.; Stengelin, S.; Baringhaus, K.-H.; Enhsen, A.; Heuer, H.; Becker, W.; Corsiero, D.; Girbig, F.; Noll, R.; Weyland, C. Substrate specificity of the ileal and hepatic Na$^+$/bile acid cotransporters of the rabbit. I. Transport studies with membrane vesicles and cell lines expressing the cloned transporters. J. Lipid Res. 1999, 40, 1604–1617.
[18] Kullak-Ublick, G. A.; Beuers, U.; Paumgartner, G. Hepatobiliary transport. J. Hepatology 2000, 32 (Suppl. 1), 3–18.
[19] Navia, M. A.; Chaturvedi, P. R. Design principles for orally bioavailable drugs. Drug Discovery Today 1996, 1, 179–189.
[20] Nielsen, N. M.; Bundgaard, H. Glycolamide esters as biolabile prodrugs of carboxylic acid agents: synthesis, stability, bioconversion and physicochemical properties. J. Pharm. Sci. 1988, 77, 285–298.
[21] Nielsen, N. M.; Bundgaard, H. Evaluation of glycolamide esters and various other esters of asprin as true asprin prodrugs. J. Med. Chem. 1989, 32, 727–734.
[22] Petzinger, E.; Nickau, L.; Horz, J. A.; Schulz, S.; Wess, G.; Enhsen, A.; Falk, E.; Baringhaus, K.-H.; Glombik, H.; Hoffmann, A.; Mullner, S.; Neckermann, G.; Kramer, W. Hepatobiliary transport of hepatic 3-hydroxy-3-methylglutaryl coenzyme A reductase inhibitors conjugated with bile acids. Hepatology 1995, 22, 1801–1811.
[23] Swaan, P. W.; Szoka, F. C.; Oie, S. Use of the intestinal and hepatic bile acid transporters for drug delivery. Adv. Drug Delivery Rev. 1996, 20, 59–82.
[24] Tsuji, A.; Tamai, I. Carrier-mediated intestinal transport of drugs. Pharm. Res. 1996, 13, 963–977.

All of the above publications, patents and patent applications are herein incorporated by reference in their entirety to the same extent as if each individual publication, patent or patent application was specifically and individually indicated to be incorporated by reference in its entirety.

BACKGROUND OF THE INVENTION

1. Field of the Invention

This invention is directed to methods for providing enhanced systemic blood concentrations of drugs that are incompletely translocated across the intestinal wall after oral delivery to animals. This invention is also directed to methods for the sustained release of drugs, whether poorly or readily translocated across the intestinal wall after oral delivery to animals. Still further, this invention is directed to compounds and pharmaceutical compositions that are used in such methods.

2. State of the Art

Incomplete or poor oral bioavailability of both existing and developmental stage therapeutic and/or prophylactic compounds represents a major impediment to effective pharmaceutical drug development. Though multiple factors influence the bioavailability of drugs (including solubility, dissolution rate, first-pass metabolism, p-glycoprotein and related efflux mechanisms, etc), low intestinal cell permeability is a particularly significant reason for the poor systemic absorption of many compounds.

Compound uptake from the gut is significantly curtailed by the network of tight junctions formed by the intestinal epithelial cell layer, and the majority of drugs that are orally absorbed traverse this epithelial barrier by passive diffusion across the apical and basolateral membranes of these cells.

The physicochemical features of a molecule that favor its passive uptake from the intestinal lumen into the systemic circulation include low molecular weight (e.g. <500 Da), adequate solubility, and a balance of hydrophobic and hydrophilic character (logP generally 1.5–4.0).[19] Polar or hydrophilic compounds are typically poorly absorbed through an animal's intestine as there is a substantial energetic penalty for passage of such compounds across the lipid bilayers that constitute cellular membranes. Many nutrients that result from the digestion of ingested foodstuffs in animals, such as amino acids, di- and tripeptides, monosaccharides, nucleosides and water-soluble vitamins, are polar compounds whose uptake is essential to the viability of the animal. For these substances there exist specific mechanisms for active transport of the solute molecules across the apical membrane of the intestinal epithelia. This transport is frequently energized by co-transport of ions down a concentration gradient. Solute transporter proteins are generally single sub-unit, multi-transmembrane spanning polypeptides, and upon binding of their substrates are believed to undergo conformational changes which result in movement of the substrate(s) across the membrane.

Over the past 10–15 years, it has been found that a number of orally administered drugs are recognized as substrates by some of these transporter proteins, and that this active transport may largely account for the oral absorption of these molecules.[24] While in most instances the transporter substrate properties of these drugs were unanticipated discoveries made through retrospective analysis, it has been appreciated that, in principle, one might achieve good intestinal permeability for a drug by designing in recognition and uptake by a nutrient transport system.

Incomplete bioavailability of drugs which, nevertheless, are orally delivered, necessitates the administration of a larger dose of such drug to compensate for that amount of drug not delivered to the systemic blood circulation. Such larger doses of the drug, however, may result in greater variability in drug exposure, more frequent occurrence of side effects, decrease in patient compliance, or alternatively, require use of parenteral delivery routes.

One attractive pathway that might be exploitable for oral delivery of such drugs is the intestinal bile acid transport system.[23] Bile acids are hydroxylated steroids that play a key role in digestion and absorption of fat and lipophilic vitamins. After synthesis in the liver, they are secreted into bile and excreted by the gall bladder into the intestinal lumen where they emulsify and help solubilize lipophilic substances. Bile acids are conserved in the body by active uptake from the terminal ileum via the sodium-dependent transporter IBAT (or ASBT) and subsequent hepatic extraction by the transporter NTCP (or LBAT) located in the sinusoidal membrane of hepatocytes. This efficient mechanism to preserve the bile acid pool is termed the enterohepatic circulation (see FIG. 1). In man, the total bile acid pool (3–5 g) recirculates 6–10 times per day giving rise to a daily uptake of approximately 20–30 g of bile acids.

The high transport capacity of the bile acid pathway has been a key reason for interest in this system for drug delivery purposes. Several papers have postulated that chemical conjugates of bile acids with drugs could be used to provide liver site-directed delivery of a drug to bring about high therapeutic concentrations in the diseased liver with minimization of general toxic reactions elsewhere in the body; and gallbladder-site delivery systems of cholecystographic agents and cholesterol gallstone dissolution accelerators.[7] Several groups have explored these concepts in some detail, using the C-24 carboxylic acid, C-3, C-7, and C-12 hydroxyl groups of cholic acid (and other bile acids) as handles for chemically conjugating drugs or drug surrogates.[10,11]

The most rigorous drug targeting studies using the bile acid transport pathway to date relate to work with bile acid conjugates of HMG-CoA reductase inhibitors.[13,14,16,22] Coupling of the HMG-CoA reductase inhibitor HR 780 via an amide linkage to the C-3 position of cholate, taurocholate and glycocholate afforded substrates for both the ileal and liver bile acid transporter proteins (FIG. 2). Upon oral dosing of rats, the cholate conjugate S 3554 led to specific inhibition of HMG-CoA reductase in the liver, and in contrast to the parent compound HR 780, gave significantly reduced inhibition of the enzyme in extra-hepatic organs. Companion studies that looked at the tissue distribution of radiolabeled drugs two hours after i.v., administration through the mesenteric vein of rats also showed dramatically lower systemic levels for the bile acid conjugate relative to the parent. Because inhibition of HMG-CoA reductase requires the presence of the free carboxylic acid moiety in HR 780 this data was taken to indicate that S 3554 served as a prodrug of HR 780, undergoing hydrolysis (and other uncharacterized metabolism) in the rat liver. Interestingly, uptake of S 3554 by liver did not appear to depend on the liver bile acid transporter NTCP (which prefers taurocholate conjugates), but may instead have involved another multispecific organic anion transport system on the sinusoidal hepatocyte membrane.

In summary, while the concept of harnessing the intestinal bile acid uptake pathway to enhance the absorption of poorly absorbed drugs is well appreciated, the existing art has merely demonstrated that bile acid-drug conjugates may be effectively trafficked to the liver and generally excreted into the bile, either unchanged or as some type of metabolite. The art gives no guidance as to how one prepares a composition that exploits the bile acid transport pathway and simultaneously provides therapeutically meaningful levels of a drug substance outside of the enterohepatic circulation.

SUMMARY OF THE INVENTION

This invention is directed to the surprising discovery that the bile acid transport system can be utilized to enhance the systemic bioavailability of orally delivered drugs which are incompletely translocated across the intestinal wall of an animal. This invention, therefore, permits enhanced oral bioavailability in animals of such incompletely translocated drugs and, in addition, permits therapeutic or prophylactic systemic blood concentrations of orally delivered drugs which heretofore could not be achieved by oral administration.

Accordingly, in one of its method aspects, this invention is directed to a method for enhancing the systemic bioavailability of a drug in an animal by increasing the amount of drug translocated across the intestinal wall of said animal, which method comprises:

(a) conjugating said drug via a cleavable linker to a moiety to provide a compound of formula (I):

D-Y-T  (I)

which compound is translocated across the intestinal wall of said animal via the bile acid transport system; where D is a drug which is incompletely translocated across the intestinal wall of said animal; T is a moiety selected to permit the compound of formula (I) to be translocated across the intestinal wall of said animal via the bile acid transport system; and Y is a cleavable linker covalently connecting D to T wherein cleavage of said linker permits said drug or active metabolite thereof to be released into the systemic blood circulation of said animal; and (b) orally administering the compound of formula (I) to said animal.

In another of its method aspects, this invention is directed to a method for providing therapeutic or prophylactic blood concentrations of a drug in an animal which method comprises orally administering to said animal a composition comprising a compound of formula (II):

D'-Y-T     (II)

where D' is a drug which is insufficiently translocated across the intestinal wall to provide therapeutic or prophylactic blood concentrations when orally administered to said animal; T is a moiety selected to permit the compound of formula (II) to be translocated across the intestinal wall of said animal via the bile acid transport system; and Y is a cleavable linker covalently connecting D' to T wherein cleavage of said linker permits therapeutic or prophylactic levels of said drug or active metabolite thereof to be released into the systemic blood circulation of said animal.

Central to the methods of this invention is the appreciation that the selectivity of compounds of formula (I) and (II) to traverse the intestinal wall (and preferably to cycle within the enterohepatic circulation) permits these compounds to act as vehicles for delivery of drugs across this wall where such drugs are otherwise incompletely translocated across the intestinal wall. Moreover, the activity, specificity and localization of enzymatic activity within tissues that comprise the enterohepatic circulation allows for the selection of cleavable linkers wherein a therapeutic or prophylactic amount of the drug conjugated to said transporter compound is cleaved and delivered to the systemic blood circulation of the animal.

The compounds, D-Y—T and D'-Y—T, are preferably selected such that the resulting drug/compound conjugate participates in the enterohepatic circulation. When so selected, the linker covalently connecting the drug to the transporter moiety is preferably selected such that at least 1% and more preferably from about 1 to about 100% of the available drug or active metabolite thereof is released in each cycle within the enterohepatic circulation.

Preferred release rates of the drug in each cycle are from 5% to 95% and, more preferably, 10% to 95%.

When low release rates of the drug or active metabolite are employed, the continuous circulation of the transporter compound/drug conjugate allows for sustained release of a drug or active metabolite thereof by oral administration regardless of whether the drug is completely or incompletely absorbed into the systemic blood circulation.

Accordingly, in another of its method aspects, this invention is directed to a method for achieving sustained therapeutic or prophylactic blood concentrations of a drug or active metabolite thereof in the systemic circulation of an animal which method comprises orally administering to said animal a compound of formula (III):

D"-Y-T'     (III)

where D" is a drug having therapeutic or prophylactic activity when delivered to the systemic circulation of said animal; T' is a moiety selected to permit the compound of formula (III) to be translocated across the intestinal wall of an animal via the bile acid transport system and further selected to permit the compound of formula (III) to participate in the enterohepatic circulation of said animal; and Y is a cleavable linker covalently connecting D" to T' wherein a sufficient amount of the compound of formula (III) is cleaved to release drug D" or active metabolite thereof thereby providing a therapeutic or prophylactic systemic blood concentration in said animal.

Preferably, the cleavable linker Y is selected to provide a therapeutic and/or prophylactic blood concentration in said animal for a period of at least about 10% longer (more preferably at least 50% longer and still more preferably at least 100% longer) than the oral delivery of drug D" itself.

In this embodiment, D" is any drug regardless of whether the drug is completely or incompletely translocated across the intestinal wall into the blood circulation.

As noted above, the selection of linker is preferably made relative to the activity, specificity and localization of enzymatic activity within tissues that comprise the enterohepatic circulation such that the drug is released at a site from where it is made available to the systemic circulation. For example, in one preferred embodiment, the linker is selected to contain one or more ester groups that permit cleavage of such groups by endogenous esterases within such tissues. In another preferred embodiment, the linker is selected to contain one or more amide groups which amide groups permit cleavage of such groups by endogenous proteases. FIGS. 7A through 7D illustrate suitable groups for use in such linker chemistry.

The methods of this invention are preferably achieved by use of compounds of formulae (I), (II) or (III) above. Accordingly, in one of its composition aspects, this invention is directed to a compound of formula (I):

D-Y-T     (I)

where D is a drug which is incompletely translocated across the intestinal wall of said animal; T is a moiety selected to permit the compound of formula (I) to be translocated across the intestinal wall of said animal via the bile acid transport system; and Y is a cleavable linker covalently connecting D to T wherein cleavage of said linker permits said drug or active metabolite thereof to be released into the systemic blood circulation of said animal.

In another of its composition aspects, this invention is directed to a compound of formula (II):

D'-Y-T     (II)

where D' is a drug which is insufficiently translocated across the intestinal wall to provide therapeutic or prophylactic blood concentrations when orally administered to said animal; T is a moiety selected to permit the compound of formula (II) to be translocated across the intestinal wall of said animal via the bile acid transport system; and Y is a cleavable linker covalently connecting D' to T wherein cleavage of said linker permits therapeutic or prophylactic levels of said drug or active metabolite thereof to be released into the systemic blood circulation of said animal.

In still another of its composition aspects, this invention is directed to a compound of formula:

D"-Y-T"     (III)

where D" is a drug having therapeutic or prophylactic activity when delivered to the systemic circulation of said animal; T' is a moiety selected to permit the compound of formula (III) to be translocated across the intestinal wall of an animal via the bile acid transport system and further selected to permit the compound of formula (III) to participate in the enterohepatic circulation of said animal; and Y is a cleavable linker covalently connecting D" to T' wherein a sufficient amount of the compound of formula (III) is cleaved to release drug D" or active metabolite thereof thereby providing a therapeutic or prophylactic systemic blood concentration in said animal.

Preferably, the cleavable linker Y is selected to provide a therapeutic and/or prophylactic blood concentration in said animal for a period of at least about 10% longer (more preferably at least 50% longer and still more preferably at least 100% longer) than the oral delivery of drug D" itself.

Particularly preferred transporter moieties, T, are bile acids. It is recognized in the art that bile acids can be modified while still retaining their ability to participate in the enterohepatic circulation. For example, Kramer[12] states that for optimal recognition by the Na$^+$-dependent bile acid uptake systems in the hepatocyte and the ileocyte, the bile acids should contain a steroid moiety preferably with a cis-orientation of rings A and B, a negative charge in the side chain at position 17 and at least one hydroxyl group, preferably in alpha-orientation, at position 3, 7 or 12 of the steroid nucleus. Thus, drug attachment to these bile acids can utilize any point of substitution provided that the resulting compound can translocate the intestinal wall. FIGS. 4A–4C illustrate numerous bile acids which can be employed to prepare suitable compounds of formula I. A first class of preferred compounds are 3-substituted bile acids. Preferably such compounds are represented by formula (IV)

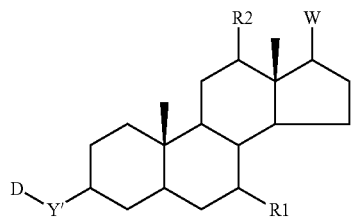

(IV)

where Y' is a cleavable linker; D is a drug, which in non-conjugated form, is incompletely translocated across the intestinal wall when orally administered to an animmal; R' is selected from the group consisting of hydrogen and OH; R$^2$ is selected from the group consisting of hydrogen and OH; and W is selected from the group consisting of —CH(CH$_3$)W' where W' is a substituted alkyl group containing a moiety which is negatively charged at physiological pH which moiety is selected from consisting of —COOH, —SO$_3$H, —SO$_2$H, P(O)(OR$^6$)(OH), —OP(O)(OR$^6$)(OH), —OSO$_3$H and the like and pharmaceutically acceptable salts thereof, R' is selected from the group consisting of alkyl, substituted alkyl, aryl and substituted aryl.

Preferably D is a drug containing at least one moiety selected from the group consisting of hydroxyl, thiol, NH, carboxylic acid (or salt thereof), phosphonic acid (or salt thereof) and phosphoric acid (or salt thereof). The linker group Y' is more preferably represented by the formula X—Y$^c$—Z— where X is the linker chemistry for attachment to the drug; Y$^c$ is a covalent bond or a linker moiety; and Z is the linker chemistry for attachment to the bile acid.

Preferably X is selected from the group consisting of —OC(O)—, —OC(O)NR$^7$—, —OC(O)OCR$^{11}$R$^{12}$O—, —OC(O)OCR$^{11}$R$^{12}$OC(O)—, —OC(O)OCR$^{11}$R$^{12}$OC(O)O—, —OC(O)OCR$^{11}$R$^{12}$OC(O)NR$^7$—, —SC(O)—, —NR$^7$C(O)O—, —NR$^7$C(O)—, —NR$^7$C(O)OCR$^{11}$R$^{12}$OC(O)—, —NR$^7$C(O)OCR$^{11}$R$^{12}$OC(O)O—, —NR$^7$CH$_2$NR$^7$C(O)—, —C(O)O—, —C(O)S—, —C(O)NR$^7$—, —C(O)NR$^7$, —C(O)R$^7$—, —C(O)OCR$^{11}$R$^{12}$O—, —C(O)OCR$^{11}$R$^{12}$OC(O)—, —C(O)OCR$^{11}$R$^{12}$OC(O)O—, —C(O)OCH$_2$C(O)NR$^7$—, —C(O)OCH$_2$CH$_2$NR$^7$C(O)—, —C(O)OCH$_2$NR$^7$C(O)—, —C(O)OCR$^{11}$R$^{12}$OC(O)NR$^7$—, —P(O)(OR$^6$)O—, —P(O)(OR$^6$)NR$^7$—, —P(O)(OR$^6$)OCR$^{11}$R$^{12}$—, —P(O)(OR$^6$)OCR$^{11}$R$^{12}$OC(O)—, —P(O)(OR$^6$)OCR$^{11}$R$^{12}$OC(O)O—, —P(O)(OR$^6$)OCR$^{11}$R$^{12}$OC(O)NR$^7$—, with the underlined atom being derived from the hydroxyl, thiol, NH, carboxylic acid (or salt thereof), phosphonic acid (or salt thereof) or phosphoric acid (or salt thereof) moiety of the drug;

each R$^7$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl; R$^{11}$ and R$^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or R$^{11}$ and R$^{12}$ together with the atoms to which they are attached form a cycloalkyl, substituted cycloalkyl, heterocycle or substituted heterocyclic ring. Such groups are depicted (inter alia) in FIGS. 7A–7D.

Preferably Z is selected from the group consisting of a bond, —O—, —S—, —C(O)O—, —OC(O)O—, —NR$^7$C(O)O—, —OC(O)NR$^7$—, —OP(O)(OR$^6$)O—, —P(O)(OR$^6$)O—, —NR$^7$P(O)(OR$^6$)O—, —C(O)NR$^7$—, —NR$^7$C(O)NR$^7$—, —NR$^7$C(O)NR$^7$—, —S(O)$_2$NR$^7$—, —S(O)—, —S(O)$_2$—, —C(O)S—, —ON=, —C(O)ON=, —NR$^7$C(O)ON=, —C(O)OCR$^{11}$R$^{12}$ON=, and a C=C linkage, wherein R$^6$–R$^{12}$ are defined as above. Such groups are illustrated in FIGS. 5A–5E.

Preferably Y' is a bond or a bivalent hydrocarbyl radical of 1 to 18 atoms having at least one alkylene, alkenylene or alkynylene group, with said at least one alkylene, alkenylene or alkynylene group optionally replaced with —O—, —S—, —NR$^7$—, —C(O)—, —C(S)—, —OC(O)—, —C(O)O, —SC(O)—, —C(O)S—, —SC(S)—, —C(S)S—, —C(O)NR$^7$—, —NR$^7$C(O)—, arylene, substituted arylene, cycloalkylene, substituted cycloalkylene, cycloalkenylene, substituted cycloalkenylene, bivalent heterocyclic group or substituted bivalent heterocyclic group.

Y' is also preferably represented by the formula:

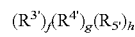

where each of R$^{3'}$, R$^{4'}$ and R$^{5'}$ are independently selected from the group consisting of alkylene, substituted alkylene, alkenylene, substituted alkenylene, alkynylene, substituted alkynylene, cycloalkylene, substituted cycloalkylene, cycloalkenylene, substituted cycloalkenylene, arylene, substituted arylene, heteroarylene, substituted heteroarylene, heterocyclene and substituted heterocyclene; and each of f, g and h are independently an integer from 0 to 3. More preferably, Y$^c$ is alkylene, alkenylene or alkynylene. Such groups are illustrated in FIG. 6.

Particularly preferred examples of suitable cleavable linkers Y' for use in this invention include structures of formulae (i) through (v) as shown below;

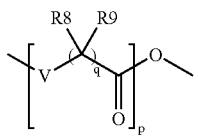
(i)

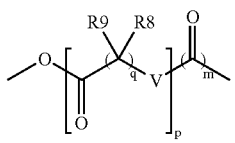
(ii)

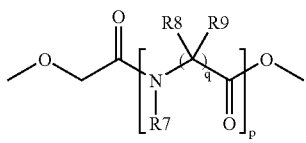
(iii)

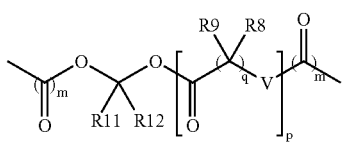
(iv)

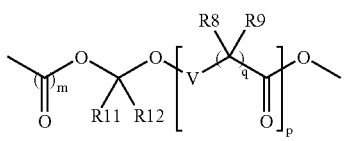
(v)

wherein V is selected from the group consisting of $NR^7$, O, S and $CR^8R^9$; each m is independently 0 or 1; each p is 0, 1, 2, 3 or 4; each q is independently 1, 2, 3, 4, 5 or 6; each $R^7$ $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or, when $R^7$ and $R^9$ are present and attached to adjacent atoms then, together with the atoms to which they are attached form a cycloalkyl, substituted cycloalkyl, heterocycle or substituted heterocyclic ring;

$R^{11}$ and $R^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring. Further illustrations of suitable linkers are found in the examples below.

A second class of preferred compounds are 17-substituted bile acids. Preferably such compounds are represented by formula (V):

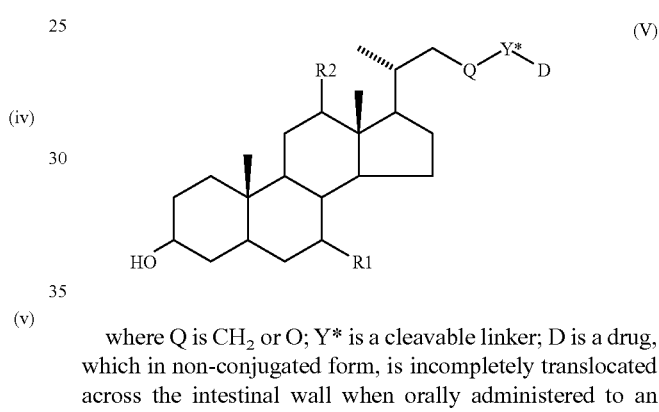
(V)

where Q is $CH_2$ or O; Y* is a cleavable linker; D is a drug, which in non-conjugated form, is incompletely translocated across the intestinal wall when orally administered to an animal; R' is selected from the group consisting of hydrogen and OH; $R^2$ is selected from the group consisting of hydrogen and OH.

The linker group, Y*, is preferably from 1 to 20 atoms in length and Y*-D together contain a moiety which is negatively charged at physiological pH. When drug D contains a primary or secondary amino group preferred compounds of formula (V) are represented by formulae (vi), (vii) and (viii) as shown below;

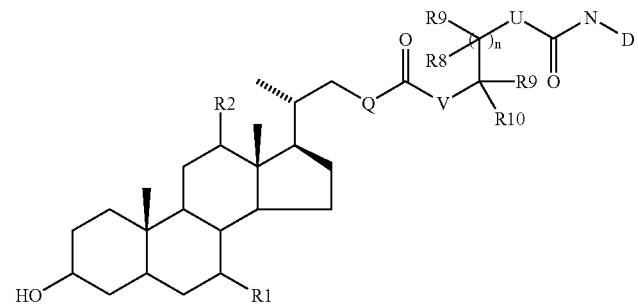
(vi)

(vii)

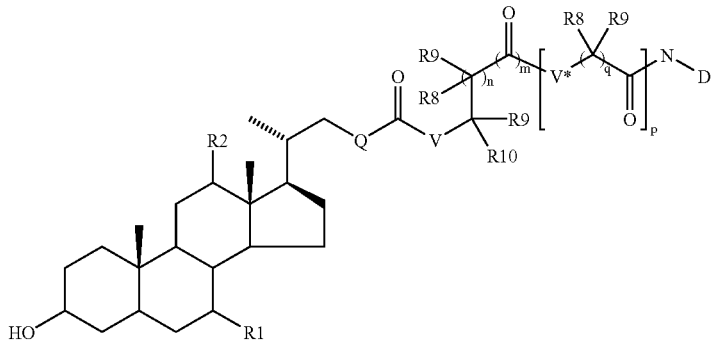

(viii)

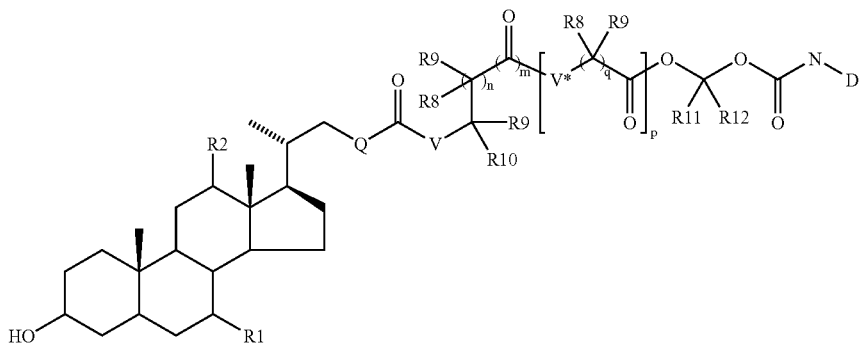

where Q is $CH_2$ or O; V and V* are independently $NR^7$, O, S or $CR^8R^9$; U is $NR^7$, O, S; $R^{10}$ is $R^8$ or $(CRWR^9)_rZ'$; Z' is selected from the group consisting of $CO_2H$, $SO_3H$, $OSO_3H$, $SO_2H$, $P(O)(OR^6)(OH)$, $OP(O)(OR^6)(OH)$ and pharmaceutically acceptable salts thereof; each m is 0 or 1; each n is 0, 1, 2, 3 or 4; each p is 0, 1, 2, 3 or 4, providing that when m is 0 p is not 0; each q is independently 1, 2, 3, 4, 5 or 6; each r is 0 or 1; $R^1$ is selected from the group consisting of hydrogen and OH; $R^2$ is selected from the group consisting of hydrogen and OH; $R^6$ is selected from the group consisting of alkyl, substituted alkyl, aryl and substituted aryl; each $R^7$, $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or, when $R^7$ and $R^9$ are present and are attached to adjacent atoms then, $R^7$ and $R^9$ together with the atoms to which they are attached form a cycloalkyl, substituted cycloalkyl, heterocycle or substituted heterocyclic ring; $R^{11}$ and $R^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring.

When drug D contains a hydroxyl group preferred compounds of formula (V) are represented by formulae (ix), (x) and (xi) as shown below;

(ix)

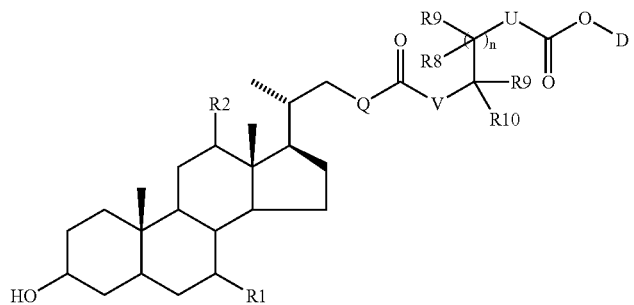

-continued

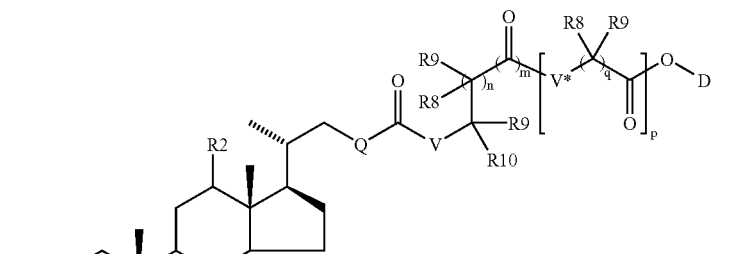

(x)

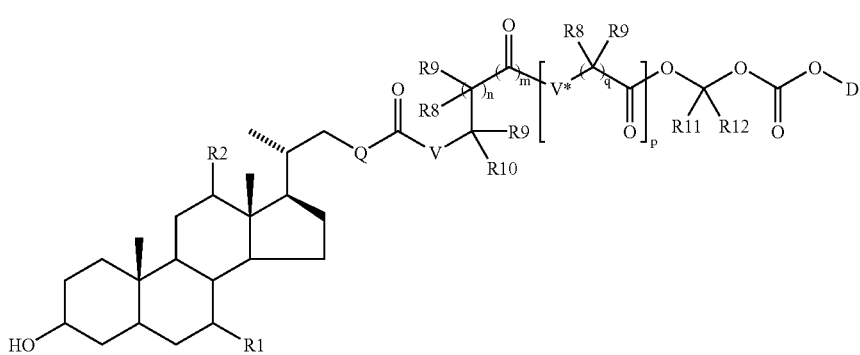

(xi)

where Q is $CH_2$ or O; V and V* are independently $NR^7$, O, S or $CR^8R^9$; U is $NR^7$, O, S; $R^{10}$ is $R^8$ or $(CR^8R_9)_rZ'$; $Z'$ is selected from the group consisting of $CO_2H$, $SO_3H$, $OSO_3H$, $SO_2H$, $P(O)(OR^6)(OH)$, $OP(O)(OR^6)(OH)$ and pharmaceutically acceptable salts thereof; each m is 0 or 1; each n is 0, 1, 2, 3 or 4; each p is 0, 1, 2, 3 or 4, providing that when m is 0 p is not 0; each q is independently 1, 2, 3, 4, 5 or 6; each r is 0 or 1; $R^1$ is selected from the group consisting of hydrogen and OH; $R^2$ is selected from the group consisting of hydrogen and OH; $R^6$ is selected from the group consisting of alkyl, substituted alkyl, aryl and substituted aryl; each $R^7$, $R^8$ and $R^9$ is independently hydrogen, alky, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or, when $R^7$ and $R^9$ are present and attached to adjacent atoms then, $R^7$ and $R^9$ together with the atoms to which they are attached form a cycloalkyl, substituted cycloalkyl, heterocycle or substituted heterocyclic ring; $R^{11}$ and $R^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring.

When drug D contains a carboxylic acid group preferred compounds of formula (V) are represented by formulae (xii) and (xiii) as shown below;

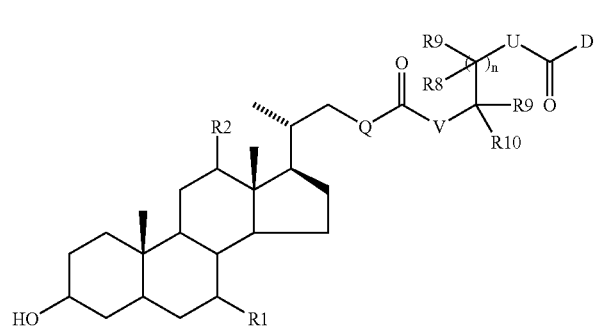

(xii)

-continued

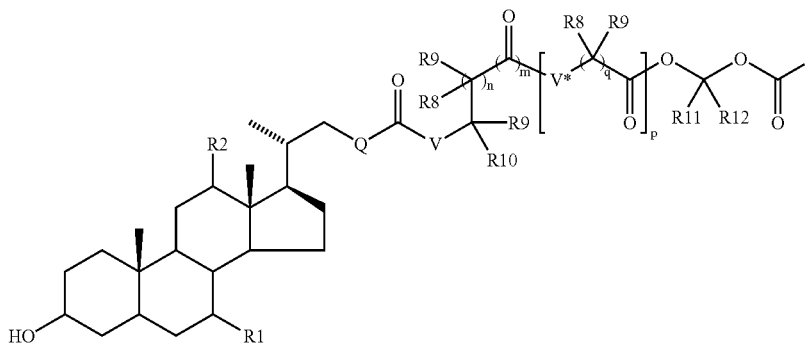

(xiii)

where Q is $CH_2$ or O; V and V* are independently $NR^7$, O, S or $CR^8R^9$; U is $NR^7$, O, S; $R^{10}$ is $R^8$ or $(CR^8R^9)_rZ'$; $Z'$ is selected from the group consisting of $CO_2H$, $SO_3H$, $OSO_3H$, $SO_2H$, $P(O)(OR^6)(OH)$, $OP(O)(OR^6)(OH)$ and pharmaceutically acceptable salts thereof; m is 0 or 1; each n is 0, 1, 2, 3 or 4; each p is 0, 1, 2, 3 or 4; each q is independently 1, 2, 3, 4, 5 or 6; each r is 0 or 1; $R^1$ is selected from the group consisting of hydrogen and OH; $R^2$ is selected from the group consisting of hydrogen and OH; $R^6$ is selected from the group consisting of alkyl, substituted alkyl, aryl and substituted aryl; each $R^7$, $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or, when $R^7$ and $R^9$ are present and attached to adjacent atoms then, $R^7$ and $R^9$ together with the atoms to which they are attached form a cycloalkyl, substituted cycloalkyl, heterocycle or substituted heterocyclic ring; $R^{11}$ and $R^{12}$ are independently hydrogen, alkyl, substituted alky, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring.

The compounds described above are preferably administered as pharmaceutical compositions comprising the drug/cleavable linker/transporter compounds described above and a pharmaceutically acceptable excipient.

BRIEF DESCRIPTION OF THE DRAWINGS

FIGS. 4A–4C illustrate several preferred bile acids for use in preparing compounds of formula (I).

FIGS. 5A through 5E illustrate suitable linker chemistry between the bile acid "BA" and the second terminal reactive functional "Z" of linker "-X-Y-Z" which can be used in preparing compounds of formula I.

FIGS. 7A through 7D illustrate suitable linker chemistry between the drug "D" and the first terminal reactive functional "X" of linker "-X-Y-Z" which can be used in preparing compounds of formula I.

FIGS. 8–22 illustrate reaction schemes for preparing compounds of formula (II).

DETAILED DESCRIPTION OF THE INVENTION

Figure 1:
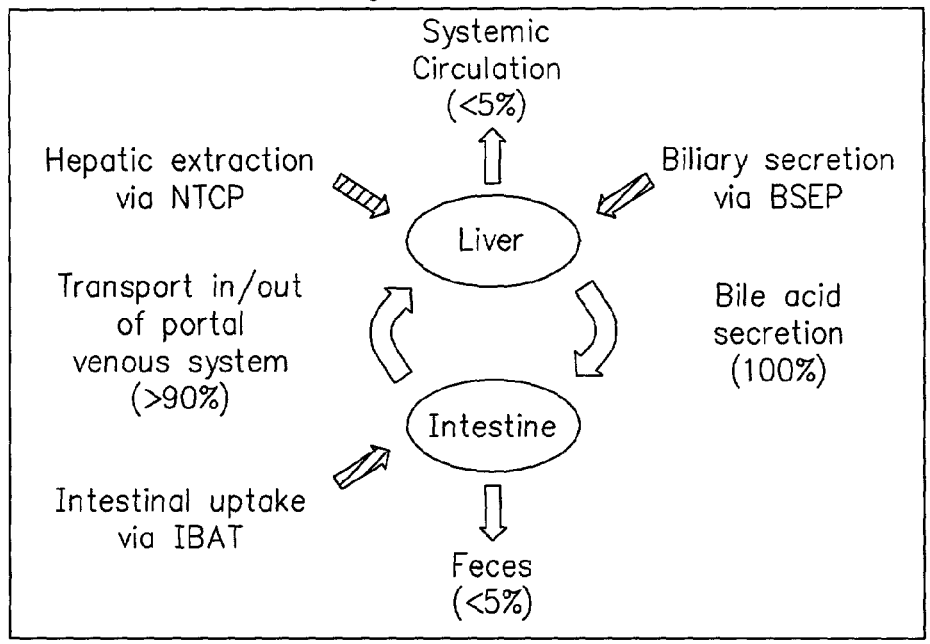
FIG. 1 illustrates the enterohepatic circulation with key transporter proteins identified which mediate bile acid circulation.
Figure 2:
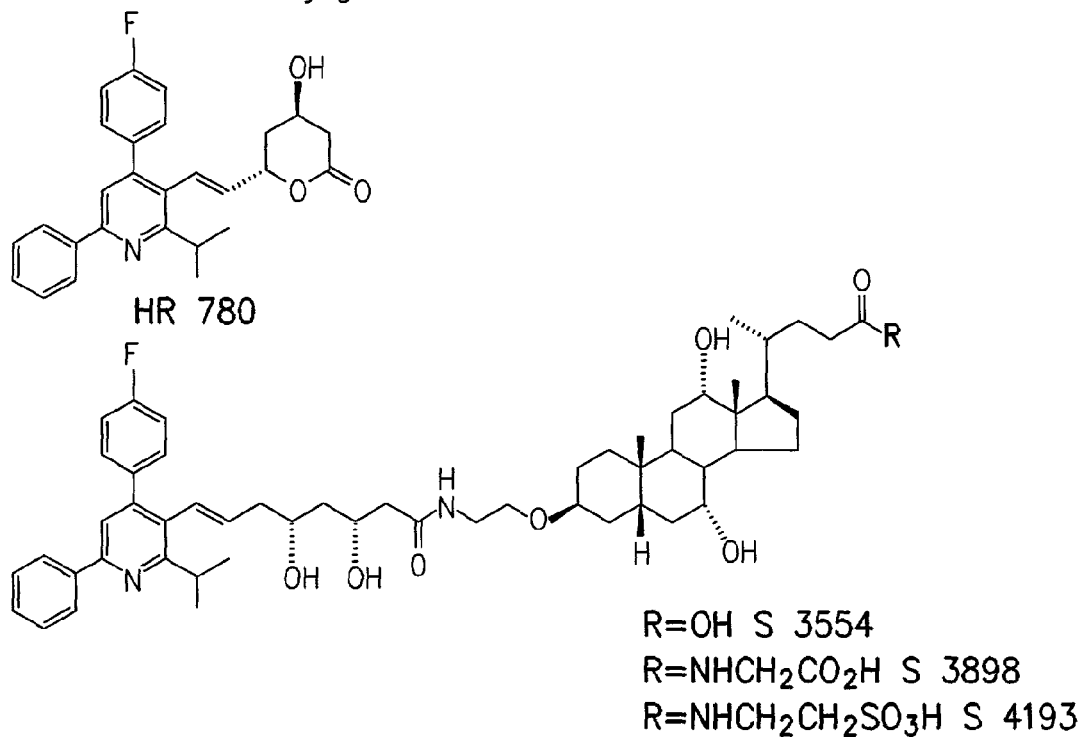
FIG. 2 illustrates the prior art HMG-CoA reductase inhibitor HR 780 as well as prior art conjugates employing the lactone opened ring of HR 780 coupled to a bile acid.

This invention provides compositions and methods for providing enhanced systemic blood concentrations of orally delivered drugs that are incompletely translocated across the intestinal wall of an animal. This invention also provides methods and compositions for the sustained release of drugs, whether poorly or readily bioavailable via oral delivery to animals. However, prior to describing this invention in further detail, the following terms will first be defined:

Definitions

As used herein, the term "animal" refers to various species such as mammalian and avian species including, by way of example, humans, cattle, sheep, horses, dogs, cats, turkeys, chicken, and the like. Preferably, the animal is a mammal and even more preferably is a human.

"Orally delivered drugs" refer to drugs which are administered to an animal in an oral form, preferably, in a pharmaceutically acceptable diluent. Oral delivery includes ingestion of the drug as well as oral gavage of the drug.

"Systemic bioavailability" refers to the rate and extent of systemic exposure to a drug or a metabolite thereof as reflected by the area under the systemic blood concentration versus time curve.

"Translocation across the intestinal wall" refers to movement of a drug or drug conjugate by a passive or active mechanism, or both, across an epithelial cell membrane of any region of the gastrointestinal tract.

"Active metabolite of a drug" refers to products of in vivo modification of the compound D-Y-T, D'-Y-T or D"-Y-T' which have therapeutic or prophylactic effect.

"Therapeutic or prophylactic blood concentrations" refers to systemic exposure to a sufficient concentration of a drug or an active metabolite thereof over a sufficient period of time to effect disease therapy or to prevent the onset or reduce the severity of a disease in the treated animal.

"Sustained release" refers to release of a drug or an active metabolite thereof into the systemic circulation over a prolonged period of time relative to that achieved by administration of a conventional formulation of the drug.

"Tissue of the enterohepatic circulation" refers to the blood, plasma, intestinal contents, intestinal cells, liver cells, biliary tract or any fraction, suspension, homogenate, extract or preparation thereof.

"Conjugating" refers to the formation of a covalent bond.

"Bile acid transport system" refers to any membrane transporter protein capable of causing a bile acid or a derivative thereof to be translocated across a membrane of a cell of the gastrointestinal tract or liver.

"Active transport or active transport mechanism" refers to the movement of molecules across cellular membranes that:
 a) is directly or indirectly dependent on an energy mediated process (i.e. driven by ATP hydrolysis, ion gradient, etc); or
 b) occurs by facilitated diffusion mediated by interaction with specifictransporter proteins; or
 c) occurs through a modulated solute channel.

"A moiety selected to permit a compound of formula (I), (II) or (III) to be translocated across the intestinal wall of an animal via the bile acid transport system" refers to compounds which, when conjugated to the drug/cleavable linker moiety, are translocated across the intestinal wall via the bile acid transport system. Evaluation of which candidate compounds can be so translocated across the intestinal wall can be conducted by the in vitro assay set forth in Example 49 below.

"Treating" a particular disease or disorder means reducing the number of symptoms and/or severity of symptoms of the disease, and/or reducing or limiting the further progression of the disease.

"Preventing" a disease or disorder means preventing or inhibiting the onset or occurrence of the disease or disorder.

"Drugs which are insufficiently translocated across the intestinal wall to provide therapeutic or prophylactic blood concentrations" refers to drugs which, when administered orally at tolerable doses or using a practical dosage regimen, cannot provide blood concentrations of the drug or active metabolite thereof sufficient to effect either disease therapy or prophylaxis. Examples of such drugs include, for instance:
 (i) the antibiotics, cefepime, ceftazidime, ceftriaxone, aztreonam, meropenem, imipenem;
 (ii) the anticancer agents, paclitaxel, docetaxel, doxorubicin, fludarabine, gemcitabine, pentostatin, camptothecin;
 (iii) the thrombin inhibitors, argatroban, melagatran, napsagatran;
 (iv) the renin inhibitors, enalkiren, ciprokiren, terlakiren;
 (v) the HIV protease inhibitors, kynostatin, A-77003, SB-206343, XM-323;
 (vi) the gpIIb/IIIa inhibitors, lamifiban; orbofiban; fradafiban, FK-633; and
 (vii) the influenza neuraminidase inhibitors, zanamivir, BCX-1812.

"Practical dosage regimen" refers to a schedule of drug administration that is practical for a patient to comply with. For human patients, a practical dosage regimen for an orally administered drug is likely to be an aggregate dose of less than 10 g/day.

"Incompletely translocated drugs" refer to those drugs wherein less than 90%, typically less than 75%, and more typically less than 50% of the drug delivered orally to an animal is absorbed into the systemic blood circulation of the animal as the drug itself or as an active metabolite thereof, wherein incomplete absorption is due, at least in part, to incomplete translocation of the drug or active metabolite thereof across the intestinal wall of the animal. Examples of incompletely translocated drugs include, for instance, bisphosphonates such as alendronate, clondronate, ibandronate, incadronate, pamidronate, risedronate, tiludronate, zoledronate.

"Drugs that are either completely or incompletely translocated across the intestinal wall into the systemic blood circulation of an animal" refer to any of the well known orally delivered drugs currently delivered by oral administration as well as drugs which cannot be orally administered because such drugs are insufficiently translocated across the intestinal wall of an animal to provide therapeutic or prophylactic blood concentrations in said animal.

As used herein, the term "drug" refers to a compound that exhibits therapeutic (i.e. therapeutic/prophylactic) or diagnostic utility when administered in effective amounts to a mammal. Preferably the drug exhibits therapeutic (i.e. therapeutic/prophylactic) utility.

Preferably, drugs that fall into the following categories:
 i) drugs which are insufficiently translocated across the intestinal wall to provide therapeutic or prophylactic blood concentrations;
 ii) incompletely translocated drugs; or
 iii) drugs that are either completely or incompletely translocated across the intestinal wall into the systemic blood circulation of an animal contain suitable functionality to provide points of linkage in forming compounds of formula (I), (II) and (III) above. Such functionality includes, by way of example, carboxyl groups, amine groups and hydroxyl groups.

Examples of drugs containing carboxyl groups include, for instance, angiotensin-converting enzyme inhibitors such as alecapril, captopril, 1-[4-carboxy-2-methyl-2R,4R-pentanoyl]-2, 3-dihydro-2S-indole-2-carboxylic acid, enalaprilic acid, lisinopril, N-cyclopentyl-N-[3-[(2,2-dimethyl-1-oxopropyl)thio]-2-methyl-1-oxopropyl]glycine, pivopril, (2R, 4R)-2-hydroxyphenyl)-3-(3-mercaptopropionyl)-4-thiazolidinecarboxylic acid, (S) benzamido-4-oxo-6-phenylhexenoyl-4-carboxypyrrolidine, [2S-1 [R*(R*))]] 2α, 3αβ, 7αβ]-1 [2-[[1-carboxy-3-phenylpropyl]-amino]-1-oxopropyl]octahydro-1H-indole-2-carboxylic acid, [3S-1 [R*(R*))]], 3R*]-2-[2-[[1-carboxy-3-phenylpropyl]-amino-1-oxopropyl]-1,2,3,4-tetrahydro-3-isoquinolone carboxylic acid and tiopronin; cephalosporin antibiotics such as cefaclor, cefadroxil, cefamandole, cefatrizine, cefazedone, cefazuflur, cefazolin, cefbuperazone, cefmenoxime, cefinetazole, cefodizime, cefonicid, cefoperazone, ceforanide, cefotaxime, cefotefan, cefotiam, cefoxitin, cefpimizole, cefpirome, cefroxadine, cefsulodin, cefpiramide, ceftazidime, ceftezole, ceftizoxime, ceftriaxone, cefuroxime, cephacetrile, cephalexin, cephaloglycin, cephaloridine, cephalosporin, cephanone, cephradine and latamoxef; penicillins such as amoxycillin, ampicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, mezlocillin, nafcillin, oxacillin, phenethicillin, piperazillin, sulbenicillin, temocillin and ticarcillin; non-steroidal antiinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclenofac, diflunisal, etodolac, fenbufen, fenclofenac, fenclosic acid, fenoprofen, ferobufen, flufenamic acid, flufenisal, flurbiprofm, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-11-oxodibenz[b,f]oxepin-2nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac; prostaglandins such as ciprostene, 16-deoxy-16-hydroxy-16-vinyl prostaglandin $E_2$, 6,16-dimethylprostaglandin $E_2$, epoprostostenol, meteneprost, nileprost, prostacyclin, prostaglandins $E_1$, $E_2$, or $F_{2\alpha}$ and thromboxane $A_2$; quinolone antibiotics such as acrosoxacin, cinoxacin, ciprofloxacin, enoxacin, flumequine, naladixic acid, norfloxacin, ofloxacin, oxolinic acid, pefloxacin, pipemidic acid and piromidic acid.

Representative drugs containing amine groups include: acebutalol, albuterol, alprenolol, atenolol, bunolol, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alinidine, alizapride, amiloride, aminorex, aprinocid, cambendazole, cimetidine, clonidine, cyclobenzadole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, dimethoxyphenethylamine, N-[3 (R)-[2-piperidin-4-yl]ethyl]-2-piperidone-1-yl]acetyl-3(R)-methyl-β-alanine, adrenolone, aletamine, amidephrine, amphetamine, aspartame, bamethan, betahistine, clorprenaline, chlortermine, dopamine, ephrinephrine etryptamine, fenfluramine, methyldopamine, norepinephrine, tocainide, enviroxime, nifedipine, nimodipine, triamnterene, norfloxacin and similar compounds such as pipedemic acid, 1-ethyl-6-fluoro-1,4dihydro-4-oxo-7-(1-piperazinyl)-1,8-napthyridine-3-carboxy 1-cyclopropyl-6-fluoro-1,4-dihydro-4-oxo-7-(piperazinyl)-3-quinolinecarboxylic acid.

Representative drugs containing hydroxy groups include: steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosteron and tigestol; tranquilizers such as dofexazepam, hydroxyzin, lorazepam and oxazepam; neuroleptics such as acetophenazine, carphenazine, fluphenazine, perphenyzine and piperaetazine; cytostatics such as aclarubicin, daunorubicin, dihydro-5-azacytidine, doxorubicin, epirubicin, estramustin, etoposide, 7-hydroxychlorpromazin, neplanocin A, pentostatin, podophyllotoxin, vinblastin, vincristin, vindesin; hormones and hormone antagonists such as buserilin, gonadoliberin, icatibrant and leuprorelin acetate; antihistamines such as terphenadine; analgesics such as diflunisal, naproxol, paracetamol, salicylamide and salicyclic acid; antibiotics such as azidamphenicol, cefamandol, chloramphenicol, clavulanic acid, clindamycin, comptothecin, demeclocyclin, doxycyclin, imipenem, latamoxef, novobiocin, oleandomycin, oxytetracyclin, tetracyclin and thiamenicol; prostaglandins such as arbaprostil, carboprost and prostacydin; antidepressives such as 8-hydroxychlorimipramine and 2-hydroxyimipramine; antihypertonics such as sotarol and fenoldopam; anticholinerogenics such as biperidine, carbidopa, procyclidin and trihexyphenidal; antiallergenics such as cromolyn; glucocorticoids such as betamethasone, budenosid, chlorprednison, clobetasol, clobetasone, corticosteron, cortisone, cortodexon, dexamethason, flucortolon, fludrocortisone, flumethasone,flunisolid, fluprednisolon, flurandrenolide, flurandrenolon acetonide, hydrocortisone, meprednisone, methylpresnisolon, paramethasone, prednisolon, prednisol, triamcinolon and triamncinolon acetonide; narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon and pentazocin; stimulants such asmazindol and pseudoephidrine; anaesthetics such as hydroxydion and propofol; β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol and timolol; α-sympathomimetics such as adrenalin, metaraminol, midodrin, norfenefrin, octapamine, oxedrin, oxilofrin, oximetazolin and phenylefrin; β-sympathomimetics such as bamethan, clenbuterol, fenoterol, hexoprenalin, isoprenalin, isoxsuprin, orciprenalin, reproterol, salbutamol and terbutalin; bronchodilators such as carbuterol, dyphillin, etophyllin, fenoterol, pirbuterol, rimiterol and terbutalin; cardiotonics such as digitoxin, dobutamin, etilefrin and prenalterol; antimycotics such as amphotericin B, chlorphenesin, nystatin and perimycin; anticoagulants such as acenocoumarol, dicoumarol, phenprocoumon and warfarin; vasodilators such as bamethan, dipyrimadol, diprophyllin, isoxsuprin, vincamin and xantinol nicotinate; antihypocholesteremics such as compactin, eptastatin, mevinolin and simvastatin; miscellaneous drugs such as bromperidol (antipsychotic), dithranol (psoriasis) ergotamine (migraine) ivermectin (antihelminthic), metronidazole and secnizadole (antiprotozoals), nandrolon (anabolic), propafenon and quinadine (antiarythmics), serotonin (neurotransmitter) and silybin (hepatic disturbance).

Preferably the drug is not a GABA analog; L-Dopa, an L-aromatic amino acid decarboxylase inhibitor or catechol O-methyl transferase inhibitor or derivatives thereof; a naturally occurring α-amino acid or an ester or carboxamide of a naturally occurring α-amino acid; a polypeptide or peptidomimetic derived from a linear oligopeptide containing at least 3 (α-amino acids; an oligonucleotide; a cyclophane derivative, a diethylenetriaminopentaacetate derivative, or paramagnetic ion chelates thereof; histamine or tyramine; 5-de-O-methylsporaricin; a bis-(2-chloroethyl)amine containing nitrogen mustard; an HMG—CoA reductase inhibitor; a proline hydroxylase inhibitor; fluvalinate; a steroid containing the carbon substructures of the following formula:

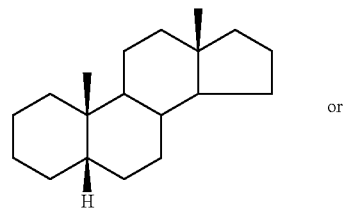

or

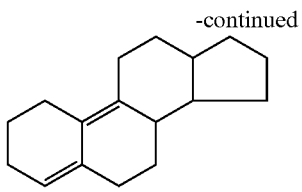

"GABA analog" preferably refers to a moiety of the following formula:

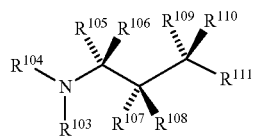

wherein $R^{103}$ is selected from the group consisting of hydrogen, an amino-protecting group, or a covalent bond linking the moiety to either Y' or Y";

$R^{104}$ is hydrogen, or $R^{104}$ and $R^{109}$ together with the atoms to which they are attached form a heterocyclic ring;

$R^{105}$ and $R^{106}$ are independently selected from the group consisting of hydrogen, alkyl, substituted alkyl, alkenyl, substituted alkenyl, alkynyl, aryl, substituted aryl, heteroaryl and substituted heteroaryl;

$R^{107}$ and $R^{108}$ are independently selected from the group consisting of hydrogen, alkyl, substituted alkyl, alkenyl, alkynyl, aryl, substituted aryl, heteroaryl and substituted heteroaryl, or $R^{107}$ and $R^{108}$ together with the atoms to which they are attached form a cycloalkyl, substituted cycloalkyl, heterocyclic or substituted heterocyclic ring;

$R^{109}$ and $R^{110}$ are independently selected from the group consisting of hydrogen, alkyl, substituted alkyl, alkenyl, alkynyl, aryl, substituted aryl, heteroaryl and substituted heteroaryl;

$R^{111}$ is selected from the group consisting of carboxylic acid, carboxylic amide, carboxylic ester, sulfonamide, phosphonic acid, acidic heterocycle, sulfonic acid, hydroxamic acid and $C(O)R^{112}$;

$R^{112}$ is a covalent bond linking the GABA analog moiety to either Y' or Y* provided only one of $R^{103}$ and $R^{112}$ links the moiety to Y' or Y*.

"Acidic heterocycle" refers to a reprotonatable heterocycle having a pKa less than 7.0. Examples of such heterocycles include the following:

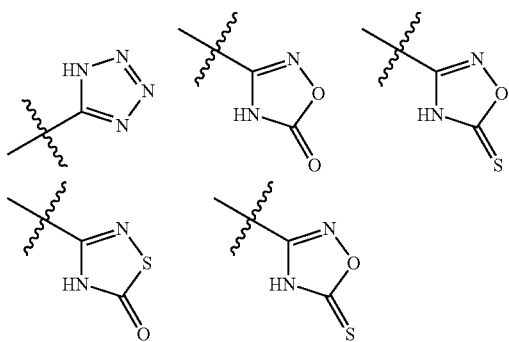

"Derivatives of L-DOPA" preferably refers to L-DOPA molecules wherein:

a) a hydrogen atom of the amino group of the L-DOPA molecule is replaced with —C(O)$R^{204}$, —C(O)O$R^{205}$ or an amino acid group, wherein $R^{204}$ is selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, and $R^{205}$ is selected from the group consisting of alkyl, substituted alkyl, cycloalkyl, substituted cycloalkyl, aryl, substituted aryl, aralkyl, substituted aralkyl, heteroaryl and substituted heteroaryl; and/or b) one or two hydrogen atoms of the two —OH groups of the catechol group of the L-DOPA molecule are replaced with —C(O)$R^{204}$, —C(O)O$R^{205}$ and/or —OC$R^{203}R^{204}$OC(O)$R^{205}$ wherein $R^{203}$ and $R^{204}$ independently are members selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, or $R^{203}$ and $R^{204}$ together with the carbon atom to which they are attached form a cycloalkyl, substituted cycloalkyl, heterocycle or substituted heterocyclic ring, or the two —OH groups of the catechol group of the L-DOPA molecule are protected with a 5-membered cyclic carbonate or 2,3-dioxo-1,4-dioxane ortho fused with a benzene ring of the catechol group of the L-DOPA molecule; and/or c) the OH group of the carboxyl moiety is replaced by —O$R^{204}$ with the proviso that one of the amino hydrogen atoms, the hydroxyl group of the carboxyl moiety or the hydrogen atom of one of the hydroxyl groups of the catechol is removed to form a covalent bond to either Y' or Y*.

"An inhibitor of L-aromatic amino acid decarboxylase" preferably refers to L-aromatic amino acid decarboxylase inhibitors such as carbidopa and benzserazide optionally with a hydrogen atom of the amino or the hydrazido group of the L-aromatic amino acid decarboxylase inhibitor replaced with —C(O)$R^{304}$, —C(O)O$R^{305}$ or an amino acid group, wherein $R^{304}$ is selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, and $R^{305}$ is selected from the group consisting of alkyl, substituted alkyl, cycloalkyl, substituted cycloalkyl, aryl, substituted aryl, aralkyl, substituted aralkyl, heteroaryl and substituted heteroaryl; and/or optionally with one or two hydrogen atoms of the two —OH groups of the catechol or the three —OH groups of the pyrogallol group of the L-aromatic amino acid decarboxylase inhibitor are replaced with —C(O)$R^{304}$, —C(O)O$R^{305}$ and/or —OC$R^{303}R^{304}$OC(O)$R^{305}$ wherein $R^{303}$ and $R^{304}$ independently are members selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, or $R^{303}$ and $R^{304}$ together with the carbon atom to which they are attached form a cycloalkyl, substituted cycloalkyl, heterocycle or substituted heterocyclic ring; or optionally with two adjacent —OH groups of the catechol or pyrogallol group protected with a 5-membered cyclic carbonate or 2,3-dioxo-1,4-dioxane ortho fused with a benzene ring of the catechol or pyrogallol group; and/or the OH group of the carboxyl moiety is replaced by —O$R^{304}$ with the proviso that one of the amino hydrogen atoms, the hydroxyl group of the carboxyl moiety or the hydrogen atom of one of the hydroxyl groups of the catechol/pyrogallol is removed to form a covalent bond to either Y' or Y*.

"Catechol O-methyl transferase inhibitor" preferably refers to catechol O-methyl transferase inhibitors such as entacapone, nitecapone and tolcapone optionally with one or two hydrogen atoms of two hydroxyl groups of the catechol group replaced with —C(O)R$^{304}$, —C(O)OR$^{305}$ and/or —OCR$^{303}$R$^{304}$OC(O)R$^{305}$ wherein R$^{303}$ and R$^{304}$ independently are members selected from the group consisting of hydrogen, alkyl, substituted alkyl, cycloalkyl, substituted cycloalkyl, aryl, substituted aryl, aralkyl, substituted aralkyl, heteroaryl and substituted heteroaryl, or R$^{303}$ and R$^{304}$ together with the carbon atom to which they are attached form a cycloalkyl, substituted cycloalkyl, heterocycle or substituted heterocyclic ring, R$^{305}$ is selected from the group consisting of alkyl, substituted alkyl, cycloalkyl, substituted cycloalkyl, aryl, substituted aryl, aralkyl, substituted aralkyl, heteroaryl and substituted heteroaryl, or the OH group of the carboxyl moiety is replaced by —OR$^{304}$, with the proviso that one of the amino hydrogen atoms or the hydrogen atom of one of the hydroxyl groups of the catechol is removed to form a covalent bond to either Y' or Y*.

"Linear oligopeptide" refers to an amide oligomer comprising either a terminal amino group or a terminal carboxylic acid group or (preferably) both a terminal amino group and a terminal carboxylic acid group, which oligomer is formed by condensation of the terminal amino residue of at least one amino acid (or GABA analog) with the terminal carboxylic acid residue of at least a second amino acid (or GABA analog). In addition to the GABA analog, the amino acids comprising the oligopeptide are either α-amino acids, β-amino acids, or a mixture of α-amino acids and β-amino acids. Note that when an α-amino acid additionally contains either a β-amino group or a β-carboxylic acid group (e.g. as in aspartic acid) a linear oligopeptide formed from such an amino acid is intended to imply that it is the α-amine or α-carboxylic acid moiety (or both) of such residue that is involved in amide formation.

"α-Amino acids" are molecules of the formula:

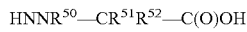
HNNR$^{50}$—CR$^{51}$R$^{52}$—C(O)OH wherein:

R$^{50}$ is hydrogen or R$^{50}$ and R$^{51}$ together with the atoms to which they are attached form a heterocyclyl ring;

R$^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{51}$ and R$^{52}$ together with the atoms to which they are attached form a cycloalkyl, substituted cycloalkyl, heterocyclyl or substituted heterocyclyl ring.

"β-Amino acids" are molecules of formula:

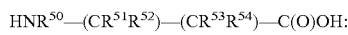
HNR$^{50}$—(CR$^{51}$R$^{52}$)—(CR$^{53}$R$^{54}$)—C(O)OH:

wherein:

R$^{50}$ is hydrogen or R$^{50}$ and R$^{51}$ together with the atoms to which they are attached form a heterocyclyl ring;

R$^{51}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{51}$ and R$^{52}$ together with the atoms to which they are attached form a cycloalkyl, substituted cycloalkyl, heterocyclyl or substituted heterocyclyl ring, or R$^{51}$ and R$^{53}$ together with the atoms to which they are attached form a cycloalkyl, substituted cycloalkyl, heterocyclyl or substituted heterocyclyl ring;

R$^{52}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R$^{53}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl or R$^{53}$ and R$^{54}$ together with the atoms to which they are attached form a cycloalkyl, substituted cycloalkyl, heterocyclyl or substituted heterocyclyl ring;

R$^{54}$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl.

"Naturally occurring amino acid" refers to any of the alpha-amino acids that are the chief components of proteins. The amino acids are either synthesized by living cells or are obtained as essential components of the diet. Such amino acids include, for example, the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"Derived from a compound" refers to a moiety that is structurally related to such a compound. The structure of the moiety is identical to the compound except at 1 or 2 positions. At these positions either a hydrogen atom attached to a heteroatom, or a hydroxyl moiety of a carboxylic, phosphonic, phosphoric or sulfonic acid group has been replaced with a covalent bond that serves as a point of attachment to another moiety. For example, the moiety:

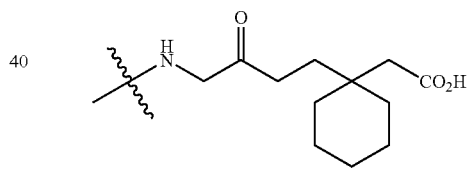

is derived from a linear oligopeptide comprising glycine and the drug gabapentin. In this moiety, a hydrogen atom has been replaced with a covalent bond. "Derived from a linear oligopeptide" is meant to specifically denote that the point of attachment is either the terminal amino group or the terminal acid group of the oligopeptide.

"Cleavable linker" refers to linkers that contain one or more functional groups which permit cleavage of such groups in vivo by, for example, endogenous enzymes. Preferably, the functional group subject to cleavage in the cleavable linker is attached adjacent the drug moiety, D, such that upon cleavage, the free drug is released. The cleavable linker preferably comprises one or more functional groups such as ester groups, amide groups, glycolamide ester groups, amidomethyl esters, acyloxyalkyl esters, alkoxycarbonyloxyalkyl esters, and the like. FIGS. 7A through 7D illustrate suitable cleavable linker functionality which can be used.

The term "drug/cleavable linker/transporter compound" (which sometimes is referred to as the "drug-transporter compound", "drug/linker/transporter compound" and "drug/ cleavable linker/transporter conjugate" refers to compounds of formula (I), (II) and/or (III).

"Alkyl" refers to alkyl groups preferably having from 1 to 20 carbon atoms and more preferably 1 to 6 carbon atoms. This term is exemplified by groups such as methyl, t-butyl, n-heptyl, octyl, dodecyl and the like.

"Substituted alkyl" refers to an alkyl group, preferably of from 1 to 20 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, SO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl—O-" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl—O—".

"Acyl" refers to the groups H—C(O)—, alkyl—C(O)—, substituted alkyl—C(O)—, alkenyl—C(O)—, substituted alkenyl—C(O)—, alkynyl—C(O)—, substituted alkynyl—C(O)- cycloalkyl—C(O)—, substituted cycloalkyl—C(O)—, aryl—C(O)—, substituted aryl—C(O)—, heteroaryl—C(O)—, substituted heteroaryl—C(O), heterocyclic—C(O)—, and substituted heterocyclic—C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl—C(O)O—, substituted alkyl—C(O)O—, alkenyl—C(O)O—, substituted alkenyl—C(O)O—, alkynyl—C(O)O—, substituted alkynyl—C(O)O—, aryl—C(O)O—, substituted aryl—C(O)O—, cycloalkyl—C(O)O—, substituted cycloalkyl—C(O)O—, heteroaryl—C(O)O—, substituted heteroaryl—C(O)O—, heterocyclic—C(O)O—, and substituted heterocyclic—C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 20 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 20 carbon atoms and more preferably 3 to 6 carbon atoms and having at least 1 and preferably from 1–2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkylene" refers to a divalent alkylene group preferably having from 1 to 20 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to alkylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Alkenylene" refers to a divalent alkenylene group preferably having from 2 to 20 carbon atoms and more preferably 1 to 6 carbon atoms and having from 1 to 2 sites of alkenyl unsaturation. This term is exemplified by groups such as ethenylene (—CH=CH—), propenylene (—$CH_2$CH=CH—), and the like.

"Substituted alkenylene" refers to alkenylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Alkynylene" refers to a divalent alkynylene group preferably having from 2 to 20 carbon atoms and more preferably 1 to 6 carbon atoms and having from 1 to 2 sites of alkynyl unsaturation. This term is exemplified by groups such as ethynylene, propynylene and the like.

"Substituted alkynylene" refers to alkynylene groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic, substituted heterocyclic and substituted alkenyl groups having amino groups blocked by conventional blocking groups such as Boc, Cbz, formyl, and the like or alkenyl/substituted alkenyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2$NRR where R is hydrogen or alkyl.

"Amidino" refers to the group $H_2$NC(=NH)— and the term "alkylamidino" refers to compounds having 1 to 3 alkyl groups (e.g., alkylHNC(=NH)—).

"Thioamidino" refers to the group RSC(=NH)- where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O) substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O— alkyl, —NRC(O)O— substituted alkyl, —NRC(O)O— alkenyl, —NRC(O)O— substituted alkenyl, —NRC(O)O— alkynyl, —NRC(O)O— substituted alkynyl, —NRC(O)O— cycloalkyl, —NRC(O)O— substituted cycloalkyl, —NRC(O)O— aryl, —NRC(O)O— substituted aryl, —NRC(O)O— heteroaryl, —NRC(O)O— substituted heteroaryl, —NRC(O)O— heterocyclic, and —NRC(O)O— substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR—alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl,—OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O) NR-alkynyl, —NRC(O)NR-substituted alkynyl, —NRC(O)NR-aryl, —NRC(O)NR-substituted aryl, —NRC(O)NR-cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxyamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Arylene" refers to a divalent unsaturated aromatic carbocyclic group of from 6 to 14 carbon atoms having a single ring (e.g., phenylene) or multiple condensed rings (e.g., naphthylene or anthrylene) which condensed rings may or may not be aromatic. Preferred arylenes include phenylene and naphthylene.

"Substituted arylene" refers to arylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O- which includes, by way of example, phenoxy, naphthoxy, and the like.

"Substituted aryloxy" refers to substituted aryl-O- groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di- arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkenyl" refers to cyclic alkenyl groups of frm 3 to 8 carbon atoms having a single cyclic ring.

"Substituted cycloalkyl" and "substituted cycloalkenyl" refers to an cycloalkyl or cycloalkenyl group, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkylene" refers to divalent cyclic alkylene groups of from 3 to 8 carbon atoms having a single cyclic ring including, by way of example, cyclopropylene, cyclobutylene, cyclopentylene, cyclooctylene and the like.

"Cycloalkenylene" refers to a divalent cyclic alkenylene groups of frm 3 to 8 carbon atoms having a single cyclic ring.

"Substituted cycloalkylene" and "substituted cycloalkenylene" refers to a cycloalkylene or cycloalkenylene group, preferably of from 3 to 8 carbon atoms, having from 1 to 5 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamnino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Guanidino" refers to the groups —NRC(=NR)NRR, —NRC(=NR)NR-alkyl, —NRC(=NR)NR-substituted alkyl, —NRC(=NR) NR-alkenyl, —NRC(=NR)NR-substituted alkenyl, —NRC(=NR)NR-alkynyl, —NRC(=NR) NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"N,N-Dimethylcarbamyloxy" refers to the group —OC(O)N(CH$_3$)$_2$.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the group consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroarylene" refers to a divalent aromatic carbocyclic group of from 2 to 10 carbon atoms and 1 to 4 heteroatoms selected from the group consisting of oxygen, nitrogen and sulfur within the ring. Such heteroarylene groups can have a single ring (e.g., pyridylene or furylene) or multiple condensed rings (e.g., indolizinylene or benzothienylene). Preferred heteroarylenes include pyridylene, pyrrolylene, indolylene and furylene.

"Substituted heteroarylene" refers to heteroarylene groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$- substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO 2—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O— aryl, —C(O)O— substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, inidazolidine, imidazoline, piperidine, piperazine, indoline, phthalimide, 1,2,3,4-tetrahydroisoquinoline, 4,5,6,7-tetrahydrobenzo [b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclene" refers to a divalent saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclene" refers to heterocyclene groups which are substituted with from 1 to 3 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, —C(O)O— aryl, —C(O)O—substituted aryl, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from the group consisting of alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl.

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of Formula I or II which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The compounds of formulae I, II and III above can be prepared by covalent coupling a difunctionalized linker precursor with a drug and a suitable transporter compound. The linker precursor is selected to contain at least one reactive functionality that is complementary to at least one reactive functionality on the drug and at least one reactive functionality on the transporter compound. Such complementary reactive groups are well known in the art as illustrated below:

COMPLEMENTARY BINDING CHEMISTRIES

| First Reactive Group | Second Reactive Group | Linkage |
|---|---|---|
| hydroxyl | carboxylic acid | ester |
| amine | carboxylic acid | amide |
| hydroxyl | isocyanate | urethane |
| amine | epoxide | hydroxylamine |
| sulfonyl halide | amine | sulfonamide |
| hydroxyl | alkyl/aryl halide | ether |
| aldehyde | amine/NaCNBH$_3$ | amine |
| ketone | amine/NaCNBH$_3$ | amine |
| amine | isocyanate | urea |

Suitable linker precursors include, by way of example, dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the linker precursor is reacted with a complementary functionality on the drug and on the transporter compound to form a compound of formula (I), (II) or (III) above.

Examples of dicarboxylic acids useful as cleavable linkers herein include, for example, succinic acid, maleic acid, etc.

Examples of diols include, for example, polyoxyalkylene compounds of the general formula HO(alkylene—O)$_a$—H where alkylene is as defined herein and a is an integer from 1 to 20.

Examples of diamines include, for example, polyalkylene amine compounds of the general formula H$_2$N(alkylene-NH)$_a$—H where alkylene is as defined herein and a is an integer from 1 to 20. Reaction of the complementary functional groups to form a covalent linkage follows conventional chemical reactions. For example, drugs with a carboxylic acid group or an amine group (as described above) can be reacted under conventional conditions with an amine or a carboxylic acid to form an amide bond using conventional coupling techniques and reagents, such carbodiimides, BOP reagent and the like which are well known in the peptide art. Alternatively, amine and hydroxyl groups can be reacted with an isocyanate under conventional conditions to form a urea or carbamate linkage respectively.

The examples set forth below illustrate protocols for the synthesis of specific drugs/cleavable linker/transporter compounds.

The transporter moiety, T, is selected to permit the drug/cleavable linker/transporter compound to be translocated across the intestinal wall of an animal via the bile acid transport system. Evaluation of which candidate compounds can be so translocated across the intestinal wall can be conducted by the in vitro assay set forth in Example 48 below.

Particularly preferred transporter moieties, T, are bile acids. In this regard, through the application of molecular biological tools, the key transporter proteins responsible for movement of the bile acid pool through the enterohepatic circulation have been defined in several species,[18] as depicted in FIG. 1. In man, the predominant circulating species are C-24 glycine and taurine conjugates of cholic acid. Transport of these conjugates via IBAT in the apical membrane of enterocytes, NTCP (or LBAT) in the sinusoidal membrane of hepatocytes and biliary secretion across the canalicular membrane of hepatocytes via the bile salt export pump BSEP and/or MRP2 are critical steps in the enterohepatic cycle. Canalicular transport is typically rate-limiting for the formation of bile, and the ~160 kDa BSEP protein is an ATP-dependent export pump homologous with the MDR P-glycoproteins. The sodium-dependent cotransporters IBAT and NTCP share 36% sequence homology and are known to have distinct, but overlapping, substrate specificities. Other constituents of the bile acid pool are substrates for these transporters, including glycine and taurine conjugates of the "primary" bile acid chenodeoxycholic acid, as well as conjugates of the "secondary" bile acids deoxycholic acid and lithocholic acid, which are formed from the primary bile salts through bacterial metabolism within the intestine.

Structure-activity studies with a panel of naturally occurring and synthetic steroid derivatives have been used to elucidate pharmacophoric features of these molecules that are important for recognition by the ileal and hepatic transporters.[3,17] One key observation is that the 3α—OH group present in all natural bile acids is not essential for high affinity interaction with the IBAT and NTCP transporters, making derivatization at C-3 of the steroid nucleus attractive for the design of bile acid-drug conjugates for enhancing intestinal drug absorption.

Figure 4C:
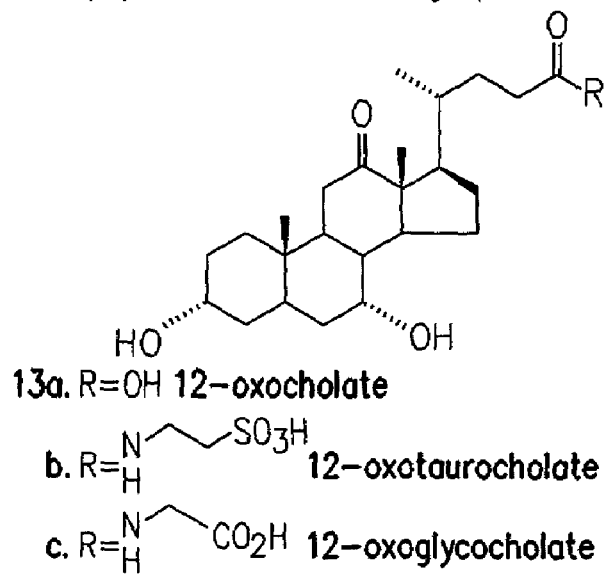
Figure 5A:
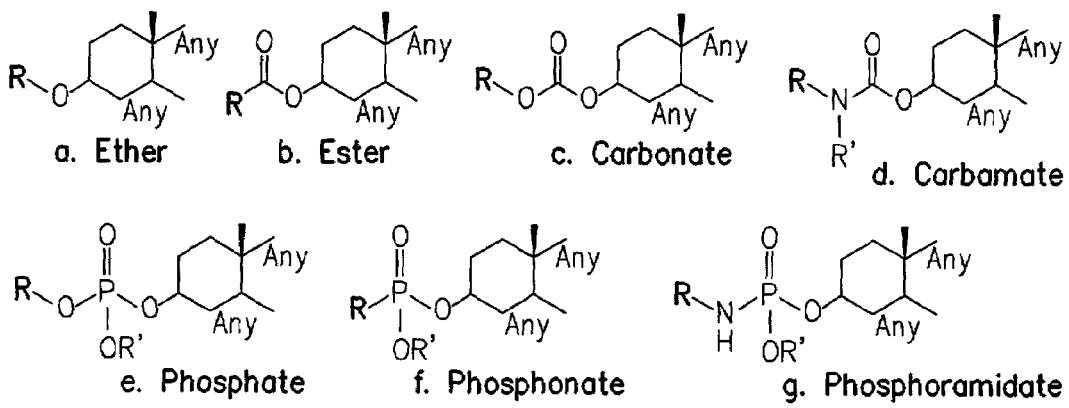
Figure 5B:
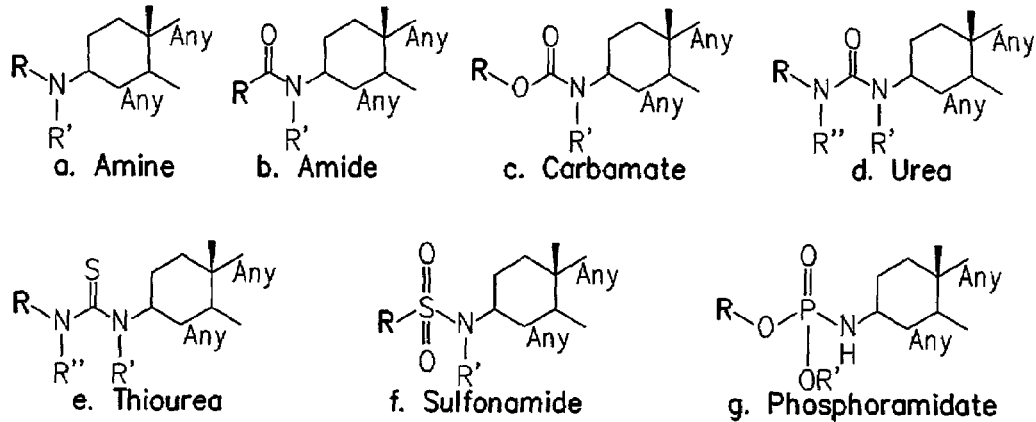

It is also recognized in the art that bile acids can be modified at other locations while still retaining their ability to participate in the enterohepatic circulation. For example, Kramer[12] states that for optimal recognition by the Na$^+$-dependent bile acid uptake systems in the hepatocyte and the ileocyte, the bile acids should contain a steroid moiety preferably with a cis-orientation of rings A and B, a negative charge in the side chain at position 17 and at least one hydroxyl group at position 3, 7 or 12 of the steroid nucleus. Thus, drug attachment to these bile acids can utilize any point of substitution provided that the resulting compound can translocate the intestinal wall. FIGS. 4A–4C illustrate numerous bile acids which can be employed to prepare suitable compounds of formula (I).

Especially preferred bile acids are derivatives of cholic acid, chenodeoxycholic acid, ursodeoxycholic acid, deoxycholic acid, hyodeoxycholic acid and lithocholic acid as set forth in FIG. 4A.

In addition to the complementary chemistry of the functional groups on the linker to the drug and transporter compound, the linker is also selected to be cleavable in vivo. Cleavable linkers are well known in the art and are selected such that at least one of the covalent bonds of the linker that attaches the drug to the transporter compound can be readily broken in vivo thereby providing for the drug or active metabolite thereof to be available to the systemic blood circulation. The linker is selected such that the reactions required to break the cleavable covalent bond are favored at the physiological site in vivo which permits drug (or active metabolite thereof) release into the systemic blood circulation.

The selection of suitable cleavable linkers to provide effective concentrations of the drug or active metabolite thereof for release into the systemic blood circulation can be evaluated relative to one or more of the endogeneous enzymes of the enterohepatic circulation as set forth in the in vitro assay provided in Example 49 below. The use of such endogenous enzymes in this in vitro assay provides a correlation to in vivo cleavage of the drug or active metabolite thereof from the drug/cleavable linker/transporter compound. The specific correlation of the in vitro results to in vivo results can be made by correlating in vivo concentrations of released drug as determined per Example 50 below with the in vitro data. Again such correlation is well within the skill of the art.

Specifically, each candidate drug/cleavable linker/transporter compound is evaluated in this assay and the rate of cleavage of drug or active metabolite thereof from each candidate compound is determined. It is understood that the cleavage rate for each candidate compound will reflect several variables such as the specific drug employed, the chemistry and point of attachment of the drug to the cleavable linker, the specific linker employed, the chemistry and point of attachment of the transporter moiety to the cleavable linker, the enzyme or enzymes assayed, etc. While each of these factors plays a role in the rate of cleavage of drug or active metabolite thereof from the candidate compound, the overall effects of these factors and hence the release rate of the drug or active metabolite thereof can be routinely evaluated using the in vitro assay of Example 49.

The respective cleavage rates of candidate drug/cleavable linker/transporter compounds are then correlated to the desired cleavage rate for a particular drug such that therapeutic and/or prophylactic concentrations of the drug or active metabolite thereof are provided to the systemic blood circulation. Such concentrations for each drug or active metabolite are readily ascertained by the skilled artisan using routine skill in the art based on the weight, age, sex, condition, etc. of the treated patient. In point of fact, for drugs that are currently delivered parenterally, intravenously, etc., such concentrations are already known in the art. Based on these factors, the skilled artisan can readily select the suitable drug/cleavable linker/transporter compound from the group of candidate compounds.

It is recognized that the exact cleavage mechanism employed is not critical to the methods of this invention provided, of course, that the drug/cleavable linker/transporter compound cleaves in vivo in some form to provide for the drug or active metabolite thereof for release into the systemic blood circulation. For example, without being limited to any theory, several different cleavage scenarios are possible:

(a) after uptake by IBAT, the drug/linker/transporter conjugate undergoes drug cleavage within the enterocyte and the liberated drug either diffuses passively across the basolateral membrane, or is subject to an active efflux process into the portal circulation. Drug that survives first pass hepatic extraction enters the systemic circulation while the bile acid moiety may be subject to enterohepatic cycling and metabolism.

(b) the drug/linker/transporter conjugate is transported intact across the enterocyte and undergoes cleavage in the portal blood. Drug that survives first pass hepatic extraction enters the systemic circulation while the bile acid pro-moiety may be subject to enterohepatic cycling and metabolism.

(c) the drug/linker/transporter conjugate is transported intact across the enterocyte and is extracted from the portal blood across the sinusoidal membrane of hepatocytes via NTCP (and perhaps other transporters, e.g. OATP). Drug or active metabolite thereof resulting from cleavage of the pro-moiety within the hepatocyte may then rejoin the portal circulation via diffusion or active transport back across the basolateral membrane, with clearance of the bile acid fragment being mediated by canalicular excretion and/or metabolism.

(d) the drug/linker/transporter conjugate is sufficiently robust that a significant quantity survives complete enterohepatic cycling (e.g., serving as substrates for each of the transporters IBAT, NTCP and BSEP, before being secreted back into the intestine). Prodrug cleavage in any of the physiological compartments noted above would liberate drug that could ultimately access the systemic circulation.

As noted above, one beneficial outcome from this scenario is modification of the drug pharmacokinetics (relative to administration of the drug alone) to provide a sustained release of the drug from its enterohepatic reservoir.

An additional possibility arises for drug/linker/transporter conjugate that are selective IBAT substrates and are not substrates for transporters within the sinusoidal hepatocyte membrane (e.g. NTCP, OATP's, etc.). Here the conjugate may be delivered intact to the systemic circulation, where it can undergo cleavage to drug or active metabolite thereof in the blood or in specific tissues harboring the appropriate enzymatic activity.

For drugs that are incompletely translocated across the intestinal wall, systemic exposure is achieved by cleavage in a tissue that is encountered after absorption (e.g. enterocyte, blood, liver, etc.). A preferred conjugate of this type is at least 1% cleaved to produce the free drug or an active metabolite thereof within a 60 minute period, when examined by one or more of the standard in vitro methods III through XI as described in Table 1 of Example 49.

For drugs that are translocated across the intestinal wall but fail to provide a sufficiently sustained systemic exposure to support a convenient dosing regimen (i.e. drugs requiring dosing more than once per day), sustained systemic exposure can be achieved by slow cleavage of the conjugate in any tissue that is encountered during enterohepatic recirculation (e.g., contents of the intestinal lumen, enterocyte, blood, liver, biliary tract, etc). A preferred conjugate of this type is at least 1% cleaved to produce the free drug or an active metabolite thereof within a 60 minute period, when examined by any one or more of the standard methods described in Table 1 of the Example 49.

A first class of conjugates of this present invention are preferably based upon C-3 substituted bile acid derivatives of formula (IV)

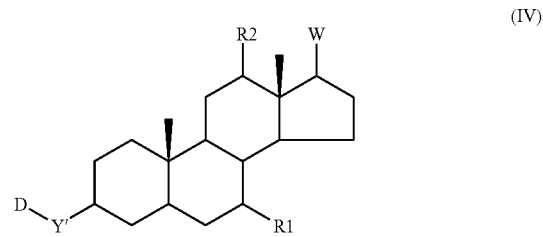

Figure 3:
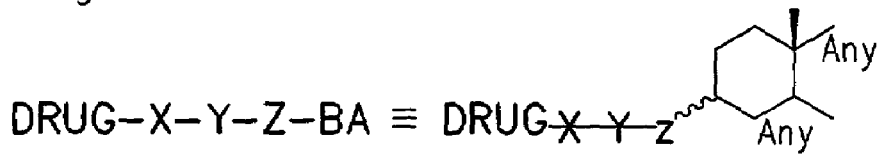
FIG. 3 illustrates that compounds of formula I can be deconvolved into a drug moiety "D", a bile acid moiety "BA", and a linker moiety represented by "-X-Y-Z" where X is the linker chemistry for attachment to the drug "D"; Y is the linker moiety and Z is the linker chemistry for attachment to the bile acid "BA".

(IV)

and are modular molecules comprising four different components in addition to the drug itself (see FIG. 3): (a) the bile acid moiety; (b) the steroid linkage chemistry (Z); (c) the linker moiety ($Y^c$); (d) the drug linkage chemistry (X). The latter three components are represented as —X—$Y^c$—Z— above.

Thus for any given drug there exists a diverse virtual library of conjugates which may be able to use the bile acid transport pathway to achieve intestinal absorption and good systemic bioavailability. Examples of useful inputs at each position of variability are listed in FIGS. 4–7. In FIGS. 4A–C are listed a number of naturally occurring bile acid molecules that are substrates for active uptake by the ileal and liver transporter proteins[17]. For any particular steroid both the parent C-24 carboxylic acid and the corresponding taurine and glycine conjugates may be useful, with the amide derivatives being generally preferred. The bile acid compounds (1)–(6) listed in FIG. 4A are superior substrates for the ileal transporter and are particularly preferred. Most particularly preferred are conjugates of the more hydrophilic steroids cholic acid (1), chenodeoxycholic acid (3) and ursodeoxycholic acid (4).

FIGS. 5A–E list useful examples of linkage chemistry to the C-3 carbon of the steroid A ring. When the C-3 carbon is $sp^3$ hybridized, both and α and β stereoisomers can be formed and have utility. Note that these linkages to the steroid nucleus include metabolically stable bonds (such as the ether a in FIG. 5A) as well as potentially cleavable bonds (such as the ester b or carbonate c in FIG. 5A). In these latter instances the steroid linkage chemistry may also optionally fulfill the role of the drug linkage chemistry (i.e. there is no intervening linker), while in other instances a linker is still employed and the prodrug may ultimately undergo cleavage into multiple fragments (the drug or active metabolite thereof, the bile acid and one or more linker fragments).

Figure 6:
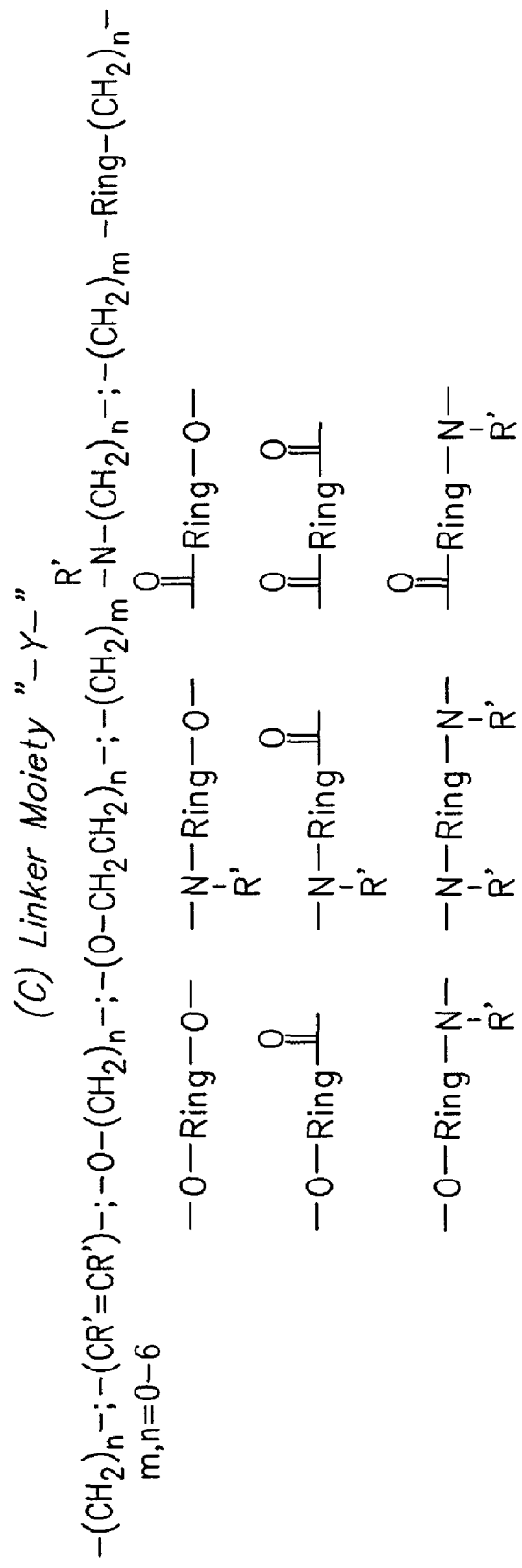
FIG. 6 illustrates suitable linker moieties.
Figure 8:
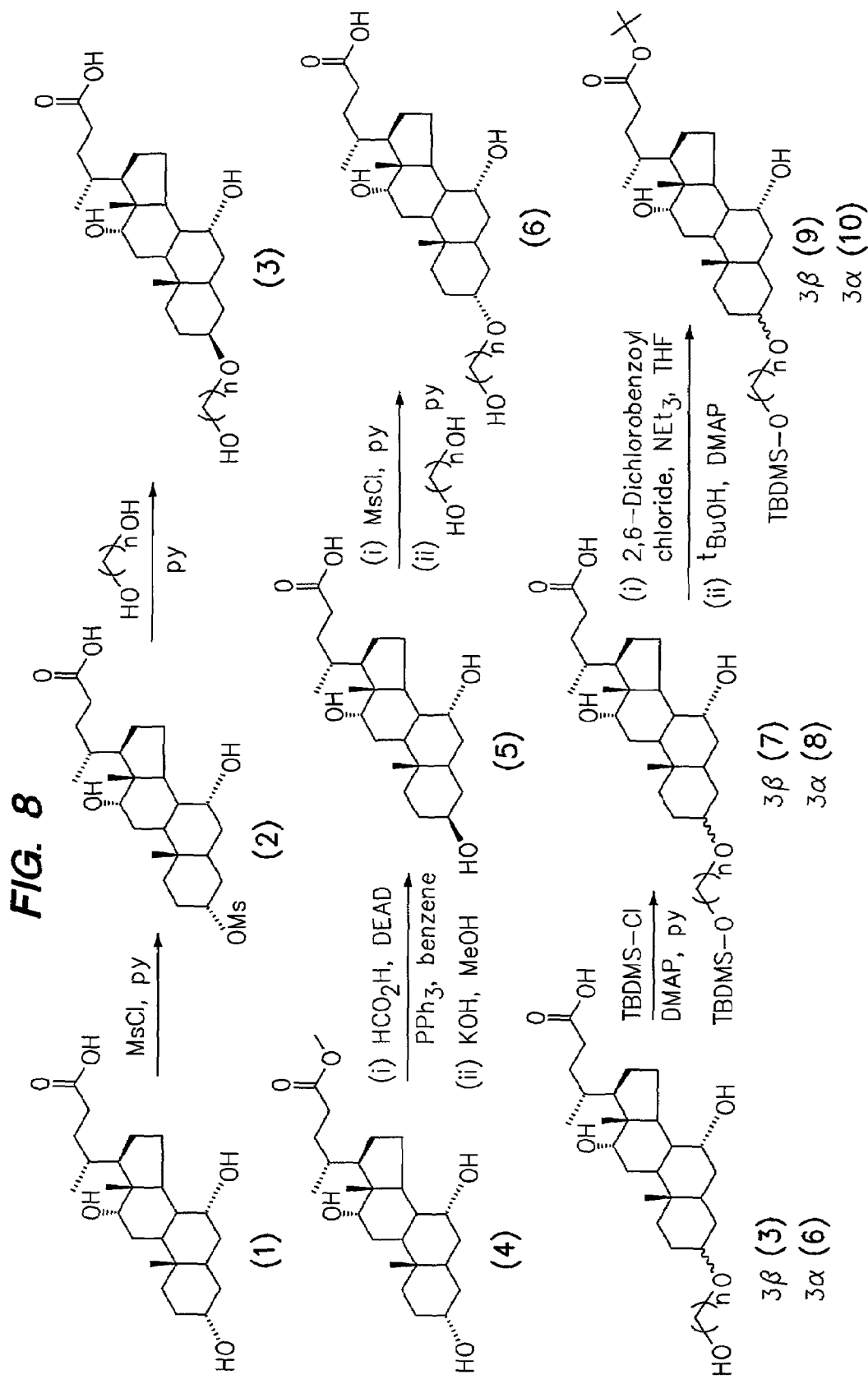
Figure 9:
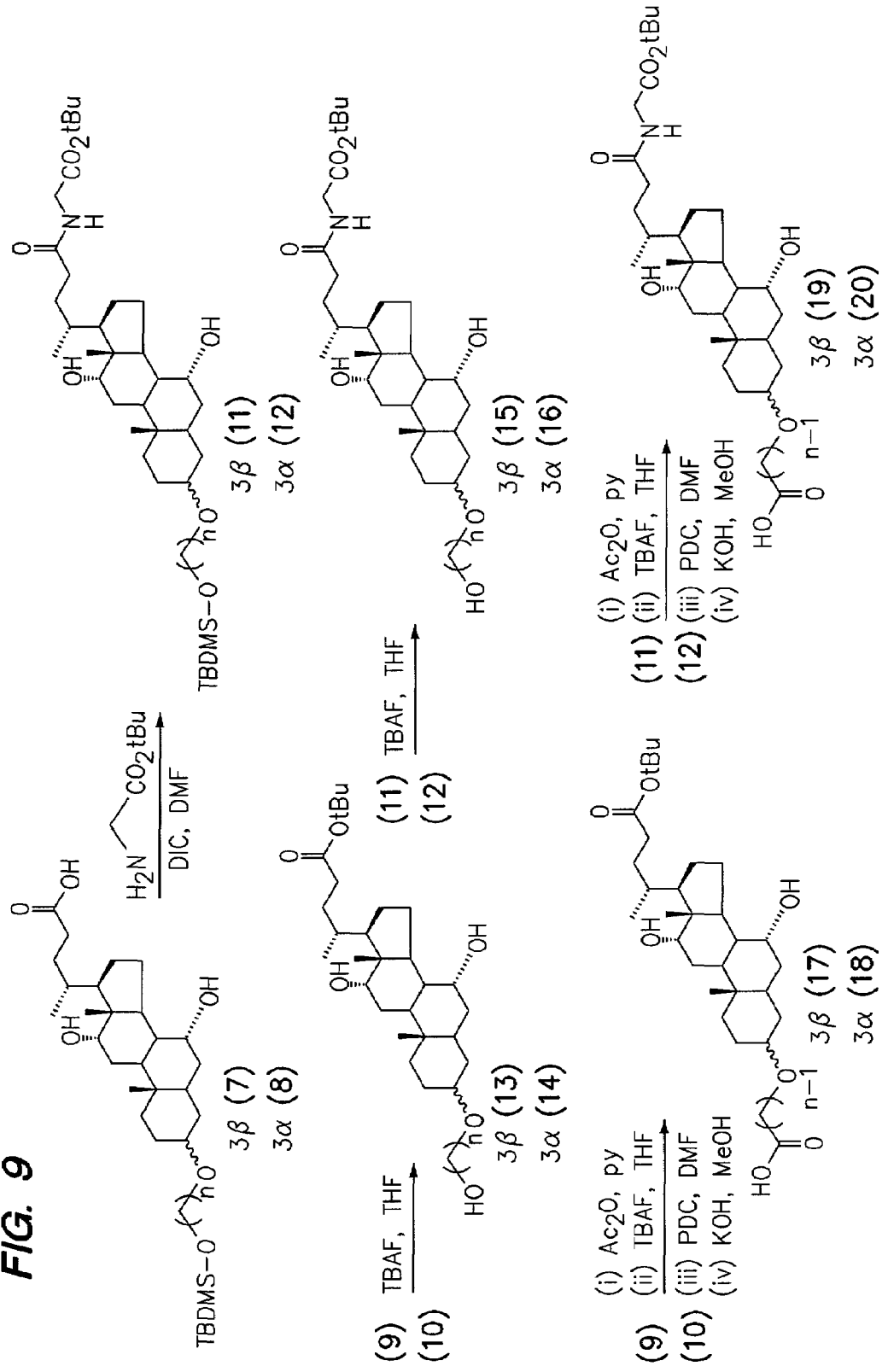
Figure 12:
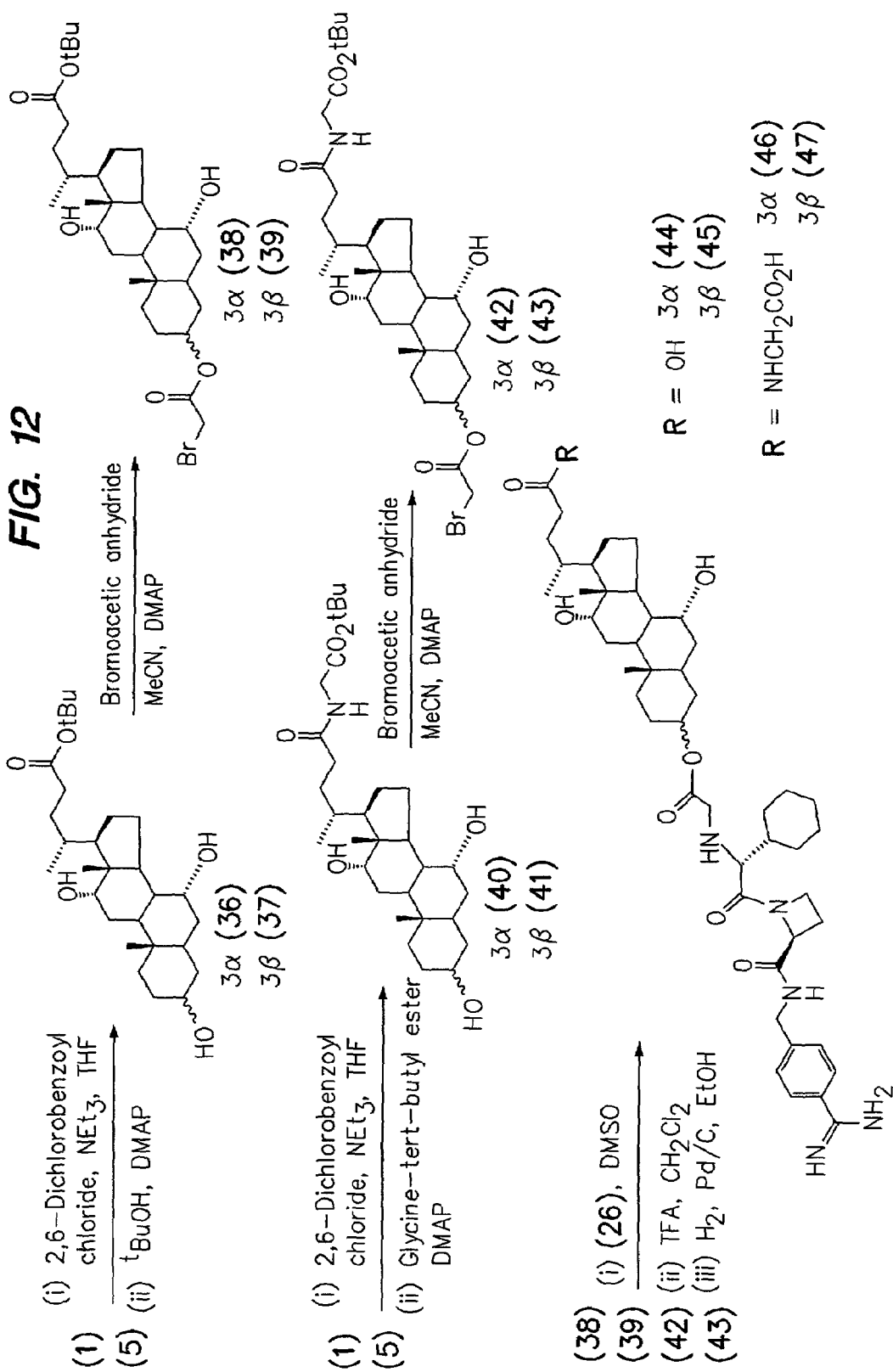
Figure 14:
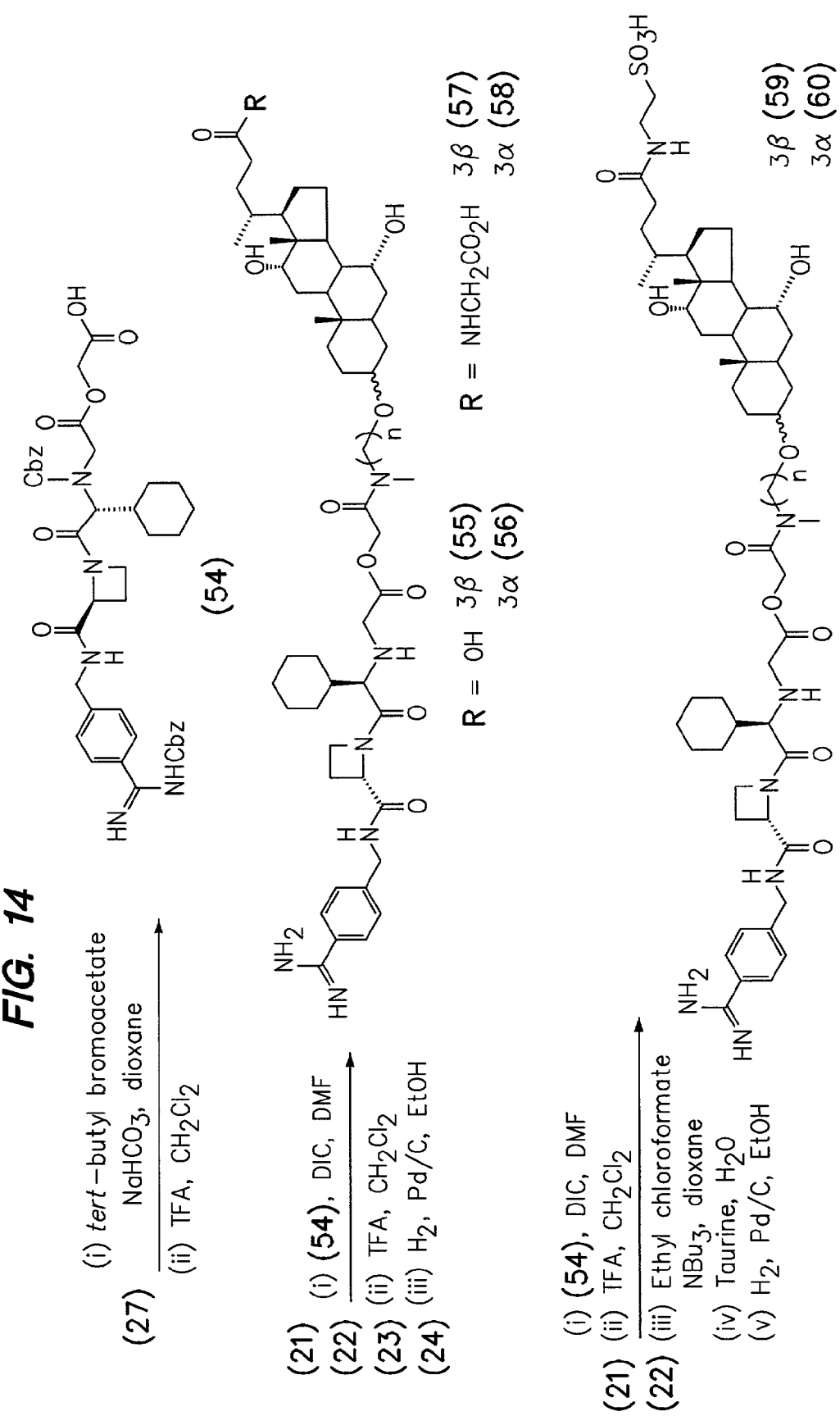
Figure 15A:
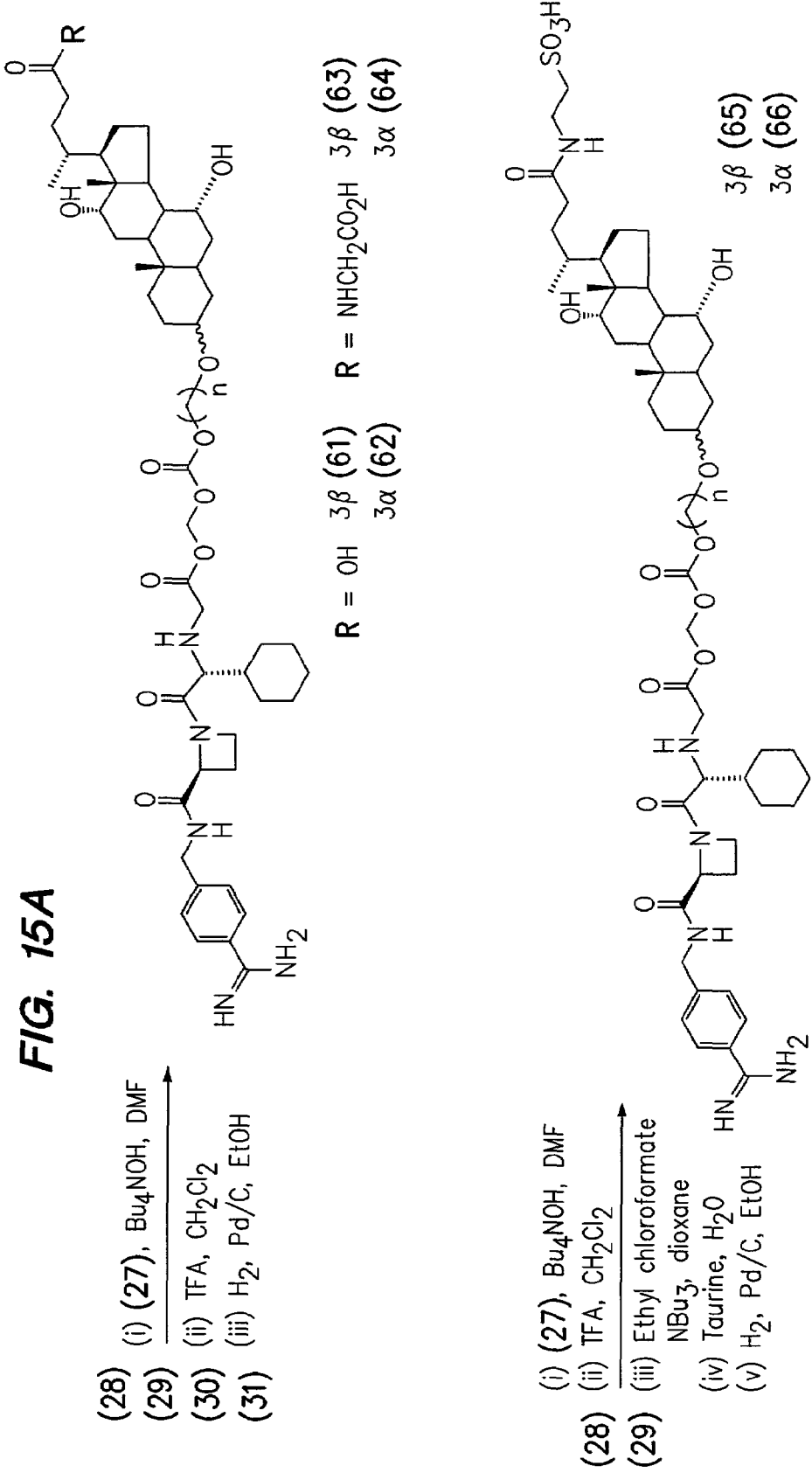
Figure 16:
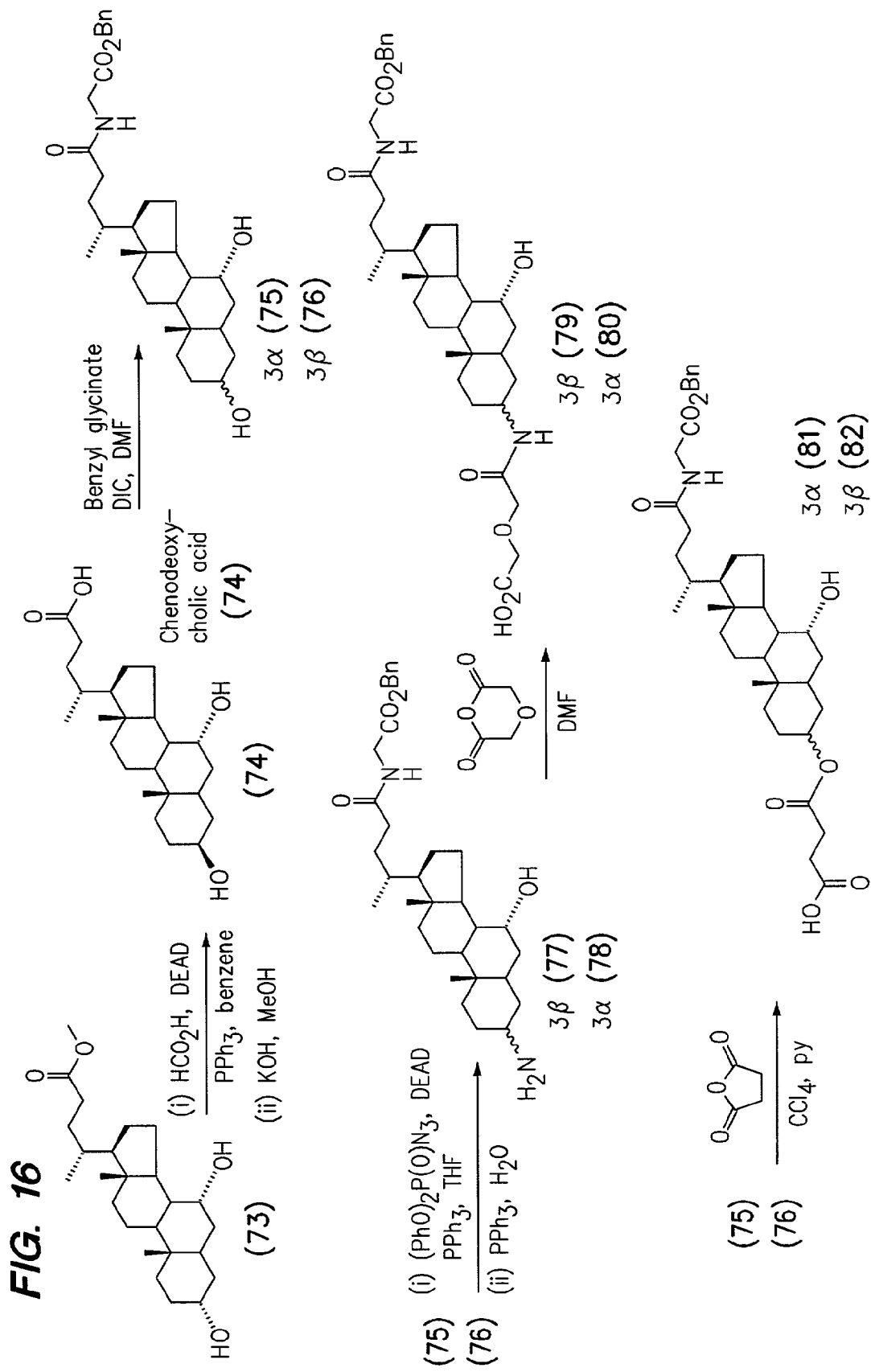
Figure 17:
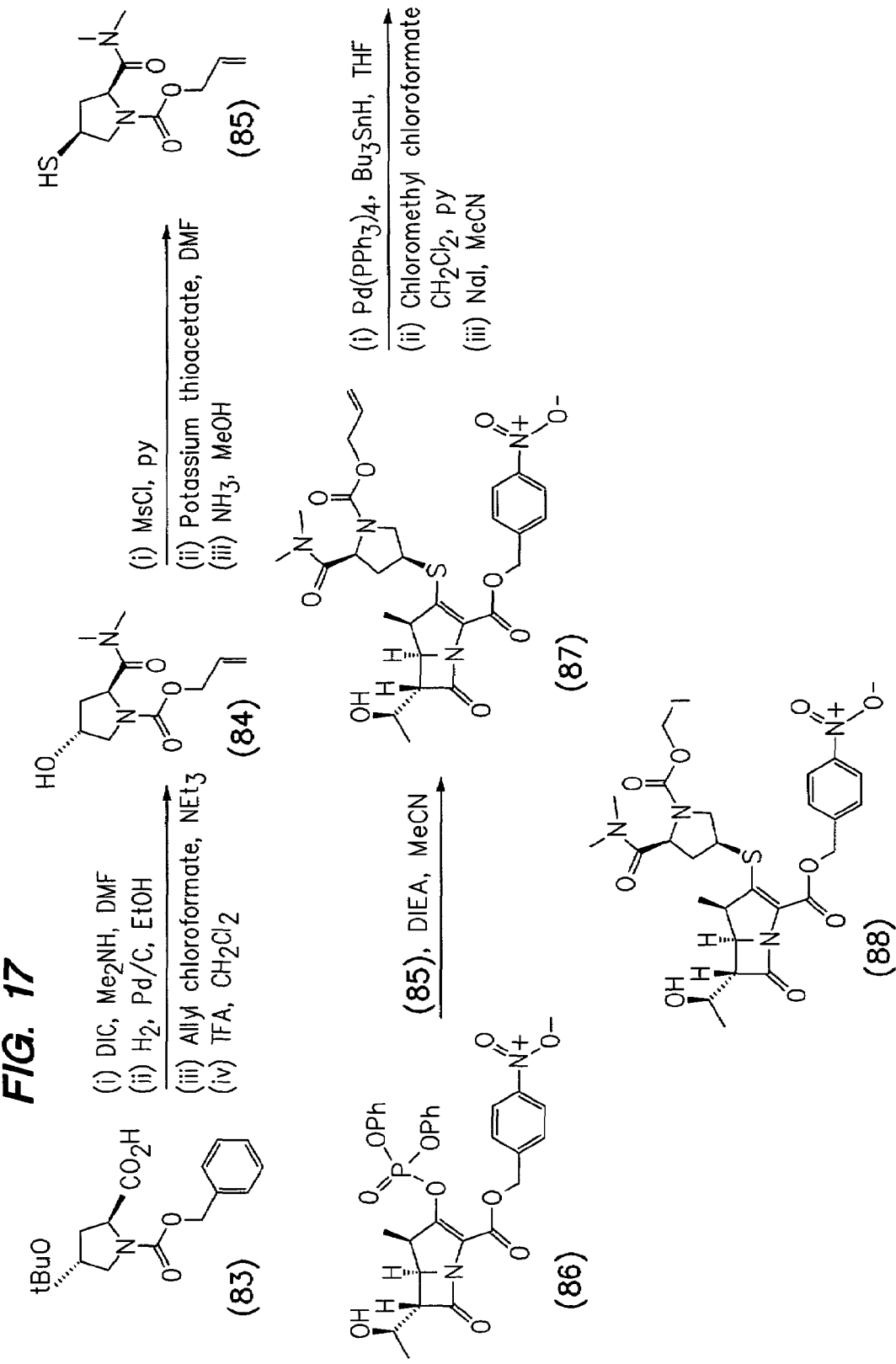
Figure 18:
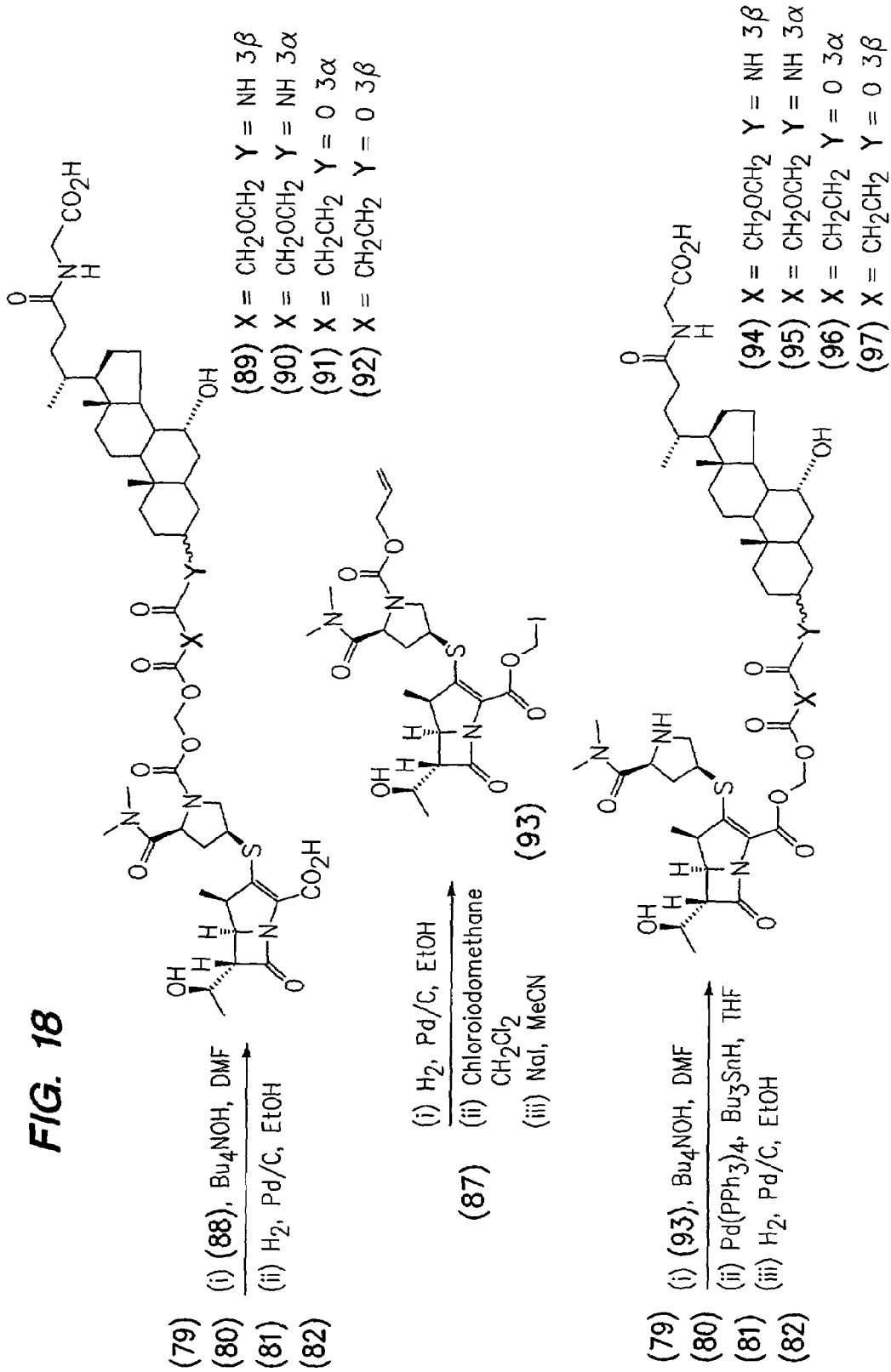
Figure 19:
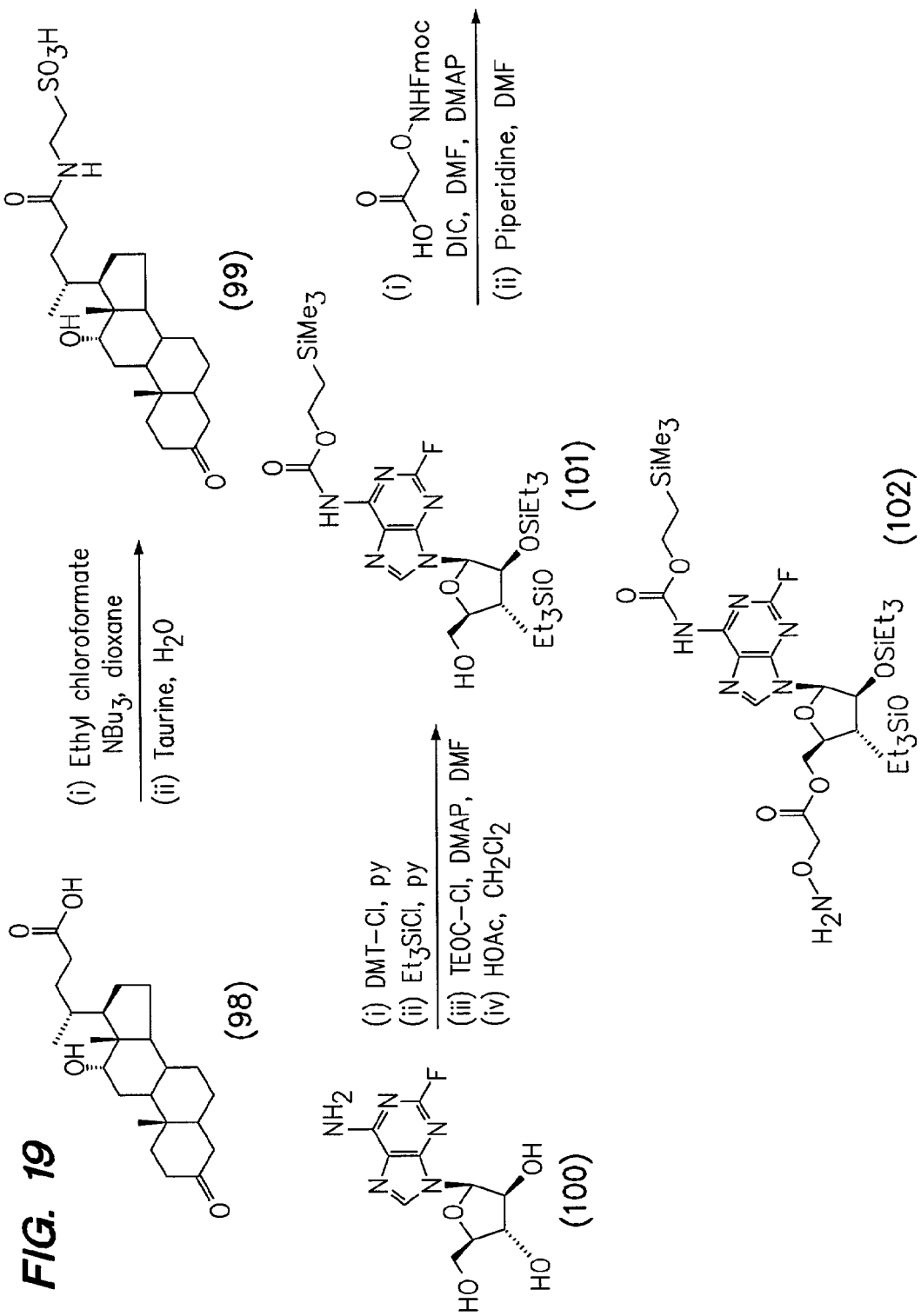
Figure 20:
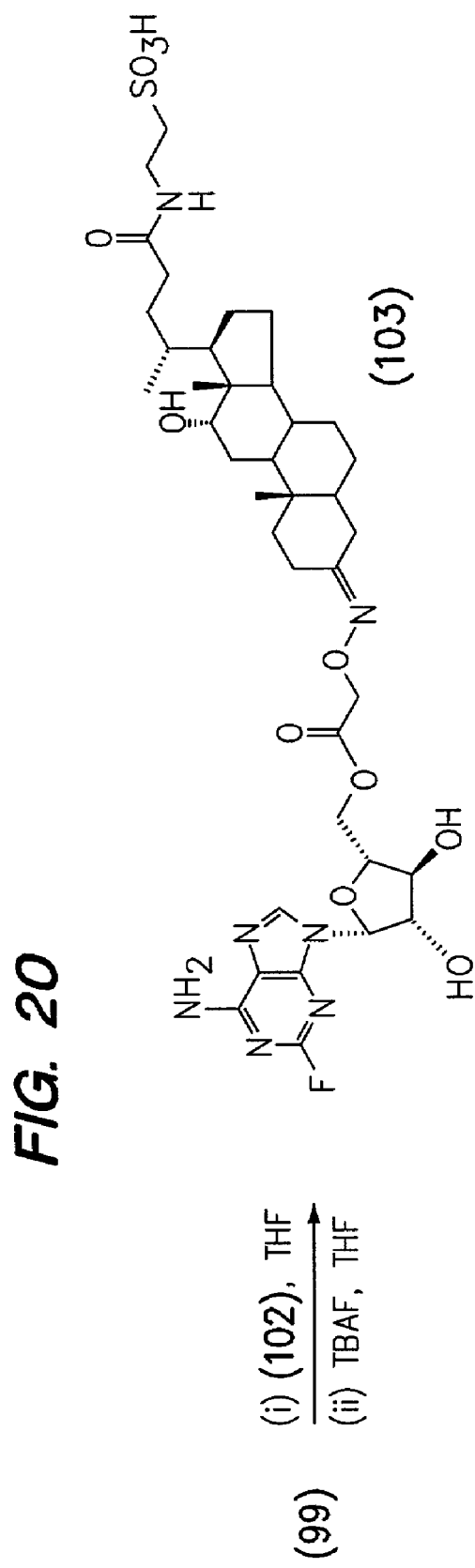
Figure 21:
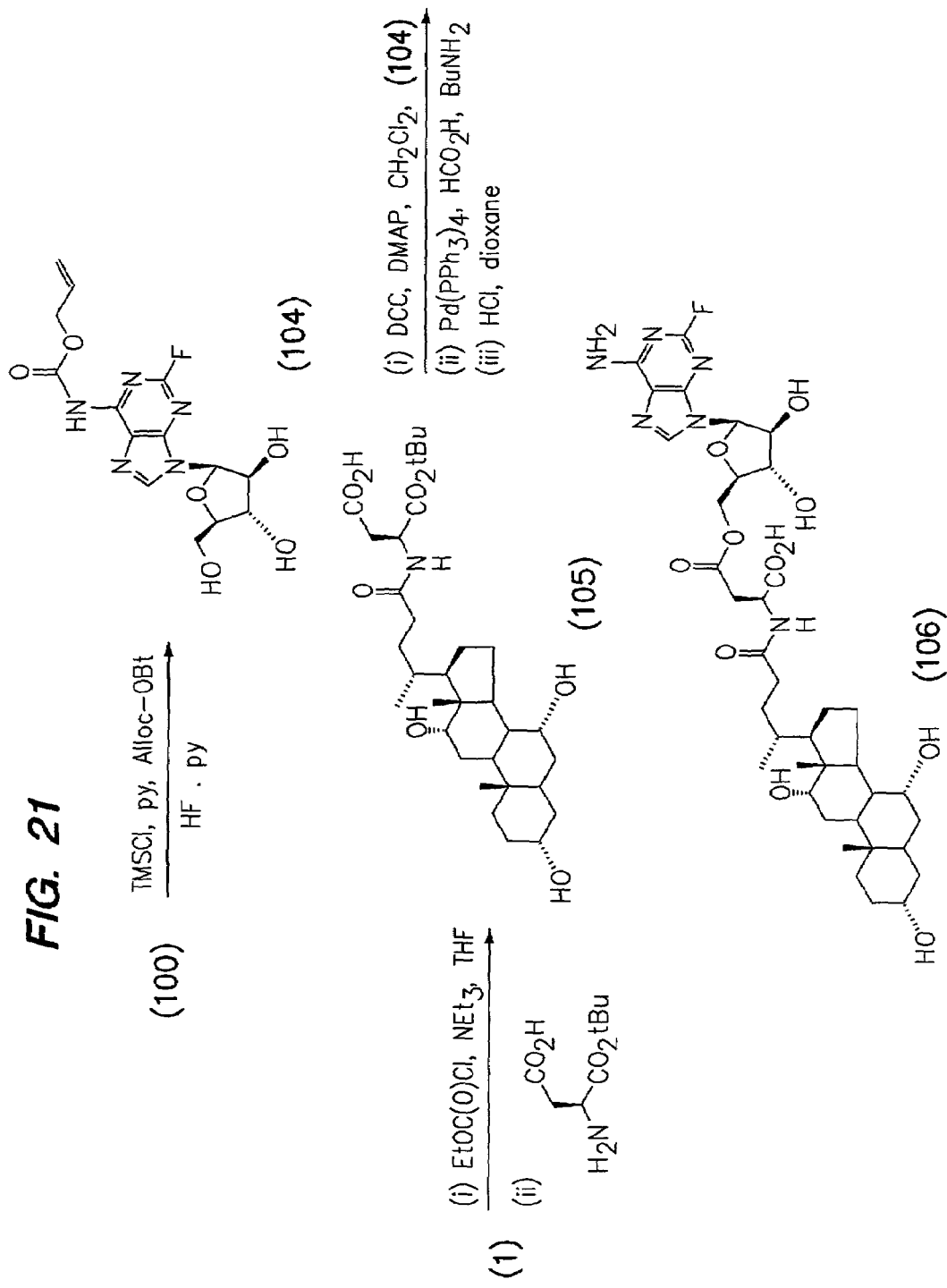
Figure 22:
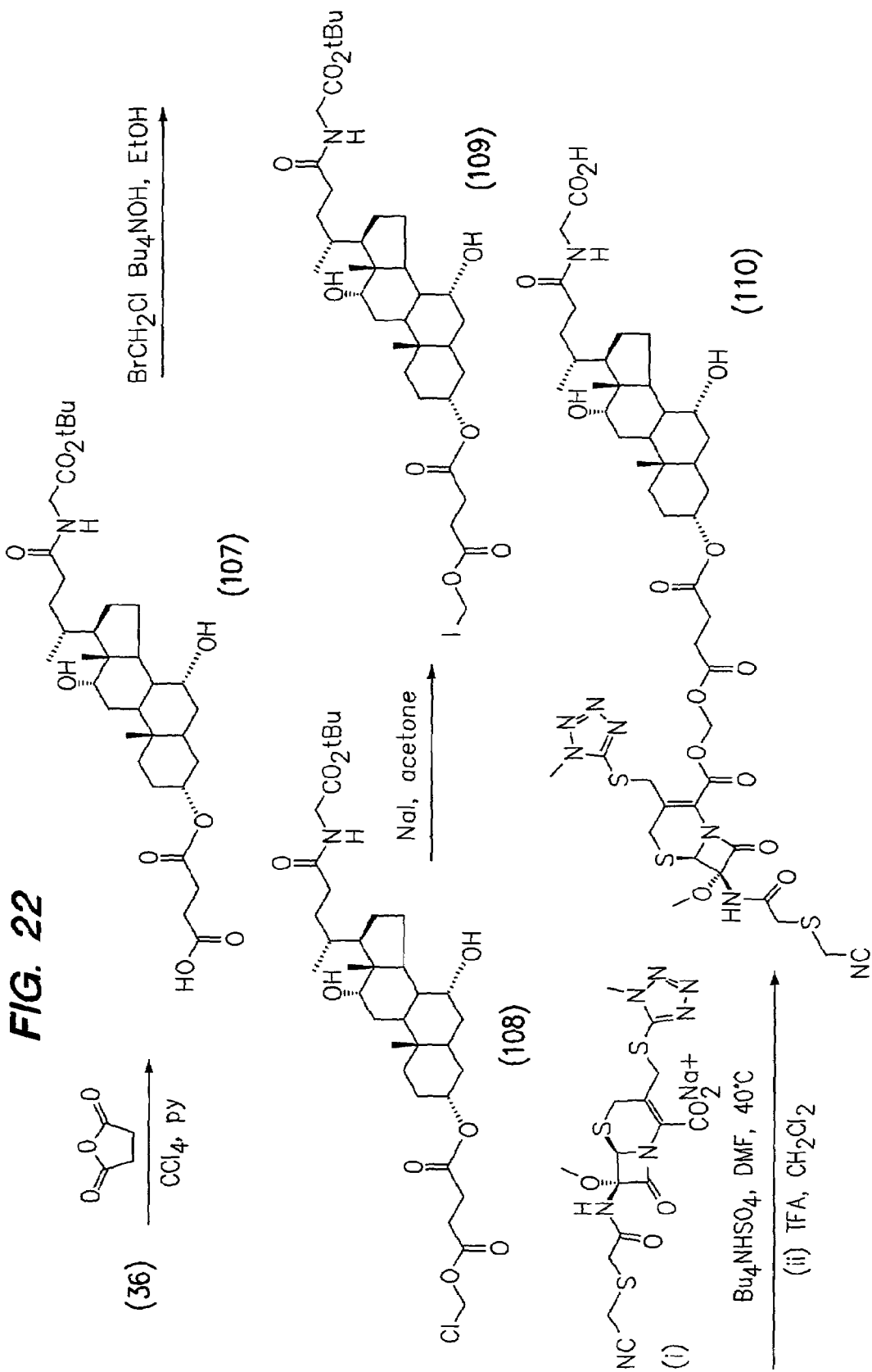

A broad range of linker moieties Y$^c$ are found to be useful in the present compositions, as listed in FIG. 6. A specific linker will be chosen bearing in mind the need to ensure recognition of the conjugate by the bile acid transporter(s), as well as appropriate presentation to the relevant metabolizing enzyme(s) responsible for prodrug cleavage. The kinetics of conjugate cleavage may be manipulated by careful selection of this linker fragment. In addition the nature of the linker moiety may be used to fine tune the physicochemical and/or pharmacological characteristics of the conjugate or its metabolites.

FIGS. 7A–D illustrate useful drug linkage chemistries on the basis of the chemical functionality within the drug to which the linker/transporter is to be attached. Methods for conjugation to carboxylic acid, phosphonic acid, alcohol, amine, amide or imide functionalities are well known within the are. The most commonly exploited biotransformation for prodrug cleavage is endogenous esterase activity. The substrate specificity and levels of esterase activity vary widely with tissue type in vivo, with significant activity being frequently found in hepatocytes. Esterolytic cleavage can also be used to trigger unmasking of prodrug derivatives of amines and amides (e.g. by decomposition of acyloxyalkyl carbamates or amidomethyl esters). Specialized conjugates (e.g. the glycolamide and amidomethyl esters e-h in FIG. 7A) can also be used to target specific esterase activity within plasma such as cholinesterase-like activity[5][20,21].

Particularly preferred examples of suitable cleavable linkers Y' for use in this invention include structures of formulae (i) through (v) as shown below;

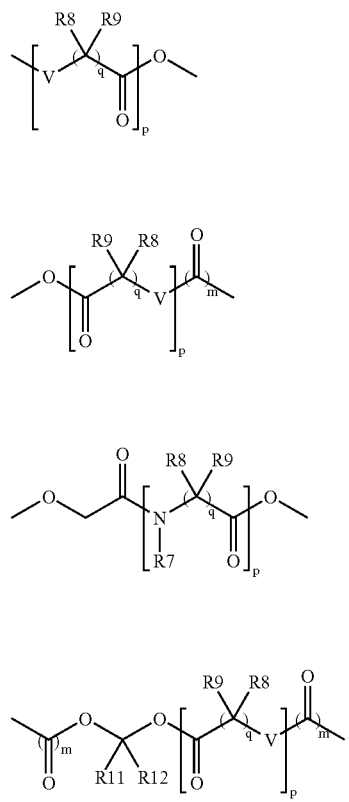

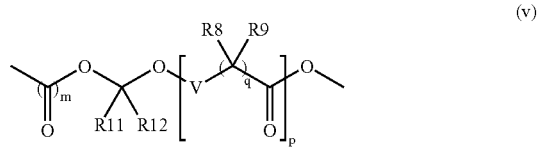

wherein V is selected from the group consisting of NR$^7$, O, S and CR$^8$R$^9$; each m is independently 0 or 1; each p is 0, 1, 2, 3 or 4; each q is independently 1, 2, 3, 4, 5 or 6; each R$^7$, R$^8$ and R$^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or R$^8$ and R$^9$ together with the atoms to which they are attached form a cycloalkyl, substituted cycloalkyl, heterocycle or substituted heterocyclic ring, or when R$^7$ and R$^9$ are present and attached to adjacent atoms, then R$^7$ and R$^9$ together with the atoms to which they are attached form a cycloalkyl, substituted cycloalkyl, heterocycle or substituted heterocyclic ring; and R$^{11}$ and R$^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or R$^{11}$ and R$^{12}$ together with the atoms to which they are attached form a cycloalkyl, substituted cycloalkyl, heterocycle or substituted heterocyclic ring.

A second class of conjugates of this present invention are preferably based upon C-17 substituted bile acid derivatives of formula (V);

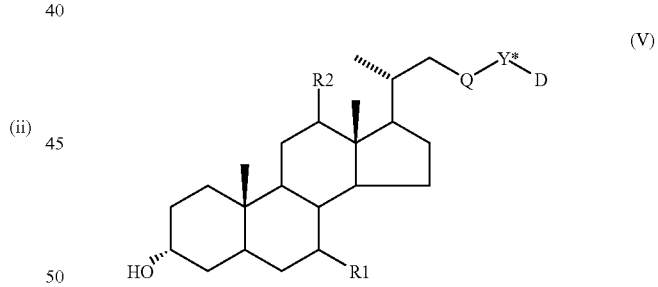

where Q is CH$_2$ or O; D is a drug, which in non-conjugated form, is incompletely translocated across the intestinal wall when orally administered to an animal; Y* is a cleavable linker group, preferably from 1 to 20 atoms in length and Y*-D together contain a moiety which is negatively charged at physiological pH; R$^1$ is selected from the group consisting of hydrogen and OH; R$^2$ is selected from the group consisting of hydrogen and OH.

Particularly preferred compounds of formula (V) are represented by formulae (vi) through (xiii), and are categorized according to the presence of amino, hydroxy or carboxylic acid groups within the drug molecule D, as shown below;

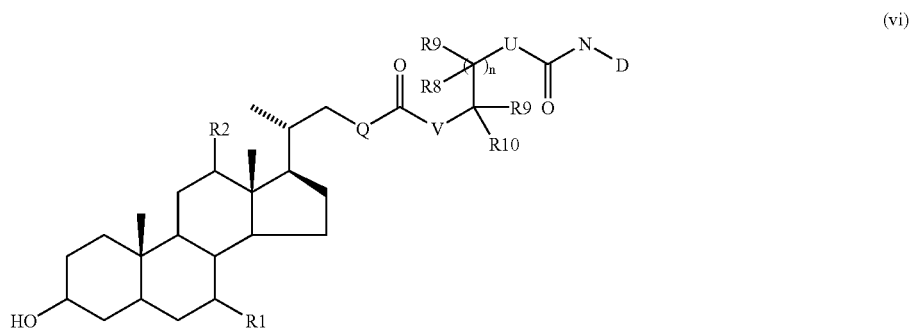
(vi)
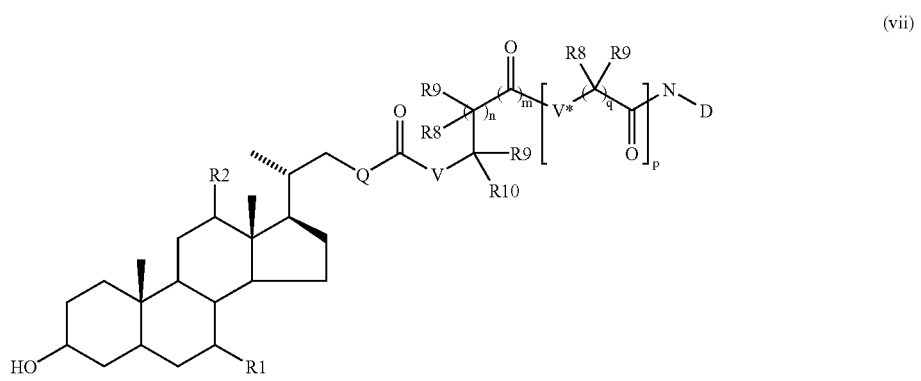
(vii)
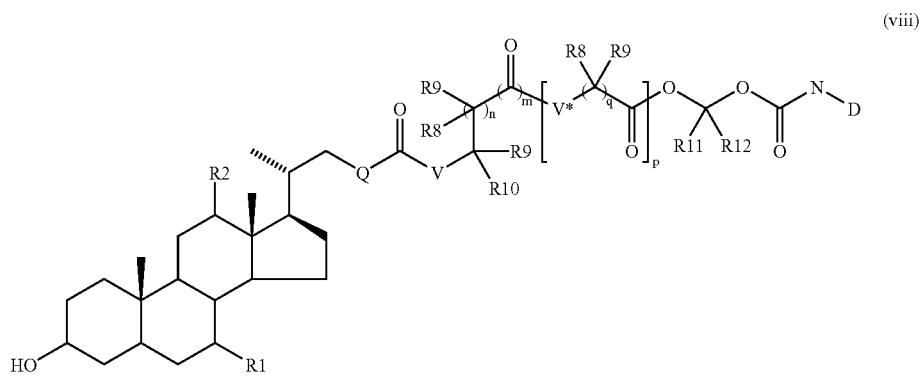
(viii)
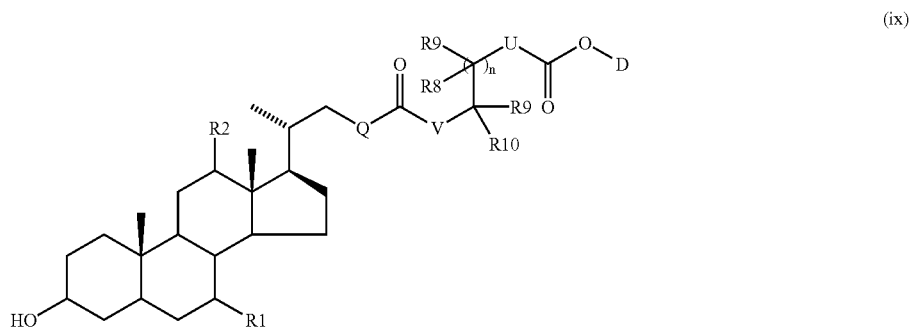
(ix)

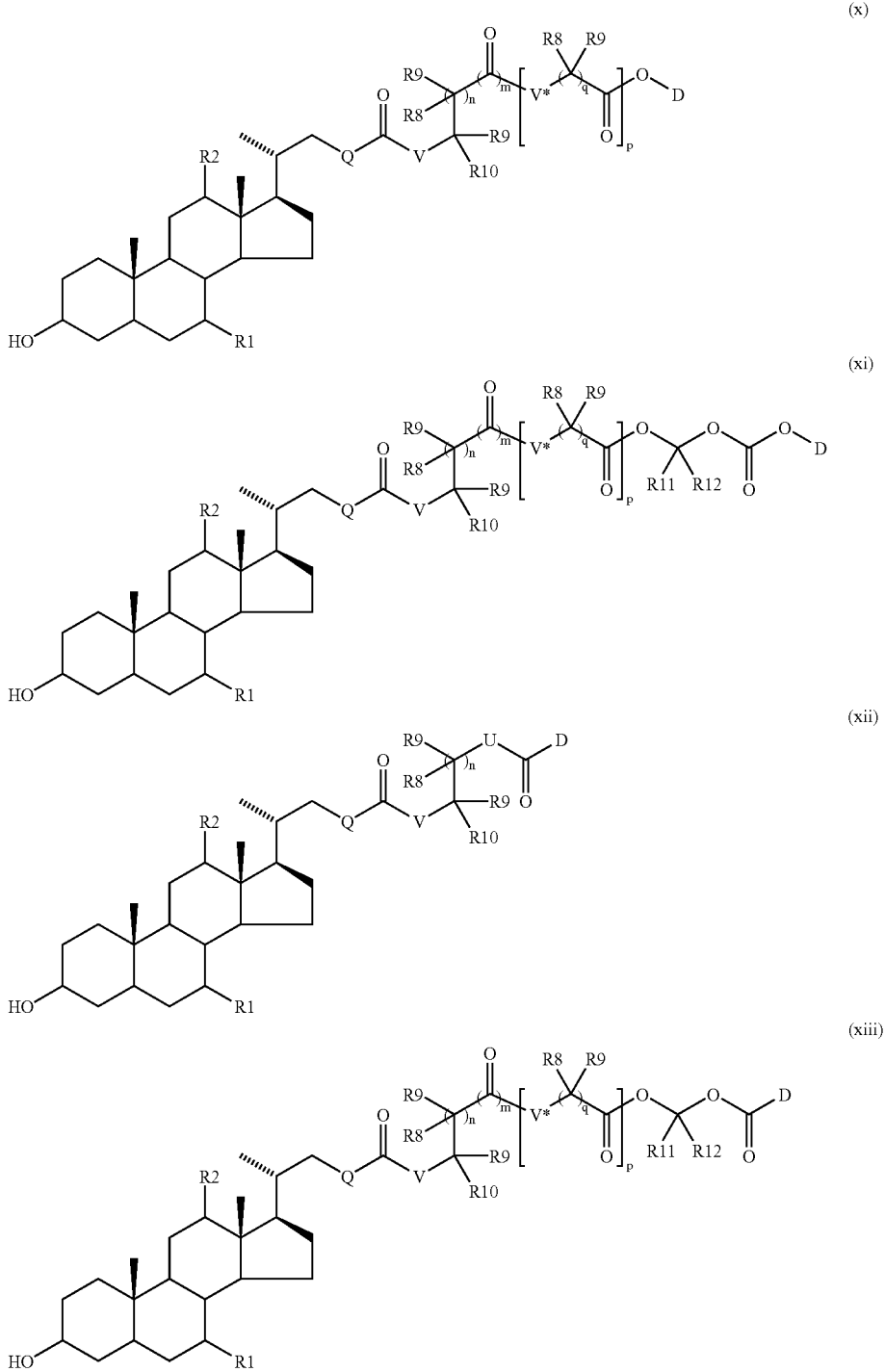

The compounds of formula (vi) comprise carbamate, thiocarbamate and urea derivatives of primary or secondary amine-containing drugs; the compounds of formula (vii) comprise amide derivatives of primary or secondary amine-containing drugs; the compounds of formula (viii) comprise acyloxyalkylcarbamate derivatives of primary or secondary amine-containing drugs;

where Q is $CH_2$ or O; V and V* are independently $NR^7$, O, S or $CR^8R^9$; U is $NR^7$, O, S; $R^{10}$ is $R^8$ or $(CR^8R^9)_rZ'$; $Z'$ is selected from the group consisting of $CO_2H$, $SO_3H$, $OSO_3H$, $SO_2H$, $P(O)(OR^6)(OH)$, $OP(O)(OR^6)(OH)$ and pharmaceutically acceptable salts thereof; each m is 0 or 1; each n is 0, 1, 2, 3 or 4; each p is 0, 1, 2, 3 or 4, providing that when m is 0 p is not 0; each q is independently 1, 2, 3, 4, 5 or 6; each r is 0 or 1; R' is selected from the group consisting of hydrogen and OH; $R^2$ is selected from the group consisting of hydrogen and OH; $R^6$ is selected from the group consisting of alkyl, substituted alkyl, aryl and substituted aryl; each $R^7$, $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or, when $R^7$ and $R^9$ are present and attached to adjacent atoms, then $R^7$ and $R^9$ together with the atoms to which they are attached form a cycloalkyl, substituted cycloalkyl, heterocycle or substituted heterocyclic ring; $R^{11}$ and $R^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring.

The compounds of formula (ix) comprise carbonate, thiocarbonate and carbamate derivatives of hydroxyl-containing drugs; the compounds of formula (x) comprise ester derivatives of hydroxyl-containing drugs; the compounds of formula (xi) comprise acyloxyalkylcarbonate derivatives of hydroxyl-containing drugs;

where Q is $CH_2$ or O; V and V* are independently $NR_7$, O, S or $CR^8R^9$; U is $NR^7$, O, S; $R^{10}$ is $R^8$ or $(CR^8R^9)_rZ'$; Z' is selected from the group consisting of $CO_2H$, $SO_3H$, $OSO_3H$, $SO_2H$, $P(O)(OR^6)(OH)$, $OP(O)(OR^6)(OH)$ and pharmaceutically acceptable salts thereof; each m is 0 or 1; each n is 0, 1, 2, 3 or 4; each p is 0, 1, 2, 3 or 4, providing that when m is 0 p is not 0; each q is independently 1, 2, 3, 4, 5 or 6; each r is 0 or 1; $R^1$ is selected from the group consisting of hydrogen and OH; $R^2$ is selected from the group consisting of hydrogen and OH; $R^6$ is selected from the group consisting of alkyl, substituted alkyl, aryl and substituted aryl; each $R^7$, $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or when $R^7$ and $R^9$ are present and attached to adjacent qtoms, then $R^7$ and $R^9$ together with the atoms to which they are attached form a cycloalkyl, substituted cycloalkyl, heterocycle or substituted heterocyclic ring; $R^{11}$ and $R^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring.

The compounds of formula (xii) comprise ester, thioester and amide derivatives of carboxylic acid-containing drugs; the compounds of formula (xiii) comprise acyloxyalkyl ester derivatives of carboxylic acid-containing drugs;

where Q is $CH_2$ or O; V and V* are independently $NR^7$, O, S or $CR^8R^9$; U is $NR^7$, O, S; $R^{10}$ is $R^8$ or $(CR^8R^9)_rZ'$; Z' is selected from the group consisting of $CO_2H$, $SO_3H$, $OSO_3H$, $SO_2H$, $P(O)(OR^6)(OH)$, $OP(O)(OR^6)(OH)$ and pharmaceutically acceptable salts thereof; each m is 0 or 1; each n is 0, 1, 2, 3 or 4; each p is 0, 1, 2, 3 or 4; each q is independently 1, 2, 3, 4, 5 or 6; each r is 0 or 1; $R^1$ is selected from the group consisting of hydrogen and OH; $R^2$ is selected from the group consisting of hydrogen and OH; $R^6$ is selected from the group consisting of alkyl, substituted alkyl, aryl and substituted aryl; each $R^7$, $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or when $R^7$ and $R^8$ are present and attached to adjacent atoms, then $R^7$ and $R^9$ together with the atoms to which they are attached form a cycloalkyl, substituted cycloalkyl, heterocycle or substituted heterocyclic ring; $R^{11}$ and $R^{12}$ are independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^{11}$ and $R^{12}$ together with the atoms to which they are attached form a cycloalkyl, substituted cycloalkyl, heterocycle or substituted heterocyclic ring.

In practice, drug/cleavable linker/transporter compounds may be prepared according to this invention by judicious selection of, e.g., a bile acid moiety, a steroid linkage chemistry, a linker moiety and a drug linkage chemistry. Alternatively, combinatorial libraries of drug/cleavable linker/transporter compounds may be prepared and candidates, optimized with respect to the desired levels of systemic exposure achievable upon oral dosing, are selected after application of in vitro and/or in vivo screens for transport, cleavage and absorption as described below.

Outlined in FIGS. 8–22 below is the preparation of a series of drug /cleavable linker/transporter compounds of several clinically utilized drugs having poor oral bioavailability wherein the transporter moiety is selected to be a bile acid. Specifically described are preparation of compounds (44)–(53) and (55)–(72) as conjugates of the thrombin inhibitor melagatran; compounds (89)–(92) and (94)–(97) as conjugates of the carbapenem antibiotic meropenem; and compound (103) and (106) as a conjugate of the antileukemic agent fludarabine; and compound (110) as a conjugate of the antibiotic cefinetazole.

Utility

The compounds and methods described herein permit significant increases in systemic blood levels of drugs or active metabolites thereof upon oral dosing of animals with the drug/linker/transporter compounds (relative to blood levels achieved with the parent compounds) when the drug is insufficiently translocated across the intestinal wall to effect therapeutic or systemic blood concentrations for the drug or when the drug is incompletely translocated across the intestinal wall.

In addition, the selection of cleavable linker also permits the drug/linker/transporter compounds described herein to provide sustained release of the drug or active metabolite thereof relative to oral dosing with the parent drug itself. In this regard, the enterohepatic recycling of the bile acid conjugates creating a reservoir for the active agent.

Pharmaceutical Formulations

When employed as pharmaceuticals, the compounds of formula (I)–(V) are usually administered in the form of pharmaceutical compositions which are administered by oral routes. Such compositions are prepared in a manner well known in the pharmaceutical art and comprise at least one active compound.

This invention also includes pharmaceutical compositions which contain, as the active ingredient, one or more of the compounds of formula (I)–(V) above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, etc. containing, for example, up to 10% by weight of the active compound using, for example, soft and hard gelatin capsules.

In preparing a formulation, it may be necessary to mill the active compound to provide the appropriate particle size prior to combining with other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. ~40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 to about 5000 mg, more usually about 10 to about 2000 mg, of the active ingredient. The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/capsule) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

Tablets, each containing 30 mg of active ingredient, are prepared as follows:

| Ingredient | Quantity (mg/capsule) |
| --- | --- |
| Active Ingredient | 30.0 mg |
| Starch | 45.0 mg |
| Microcrystalline cellulose | 35.0 mg |

-continued

| Ingredient | Quantity (mg/capsule) |
|---|---|
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. mesh U.S. sieve and mixed thoroughly. The solution of polyvinyl-pyrrolidone is mixed with the resultant powders, which are then passed through a 16 mesh U.S. sieve. The granules so produced are dried at 50 to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 4

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed though a No. 20 mesh U.S. sieve, and filled into hard gelatin capsules in 150 mg quantities.

FORMULATION EXAMPLE 5

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 mg |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 6

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

The following synthetic and biological examples are offered to illustrate this invention and are not to be construed in any way as lilmiting the scope of this invention. Unless otherwise stated, all temperatures are in degrees Celsius.

EXAMPLES

In the examples below, the following abbreviations have the following meanings. If an abbreviation is not defined, it has its generally accepted meaning.

Alloc=allyloxycarbonyl
Atm=atmosphere
Bt=benzotriazole
Cbz=carbobenzyloxy
CPM=counts per minute
DCC=dicyclohexylcarbodiimide
DMAP=4-N,N-dimethylaminopyridine
DMEM=Dulbecco's minimun eagle medium
DMF=N,N-dimethylformamide
DMSO=dimethylsulfoxide
FMOC=9-fluorenylmethyloxycarbonyl
g=gram
h=hour
HBSS=Hank's buffered saline solution
IBAT=intestinal bile acid transporter
L=liter
LBAT=liver bile acid transporter
LC/MS=liquid chromatography/mass spectroscopy
M=molar
min=minute
mL=milliliter
mmol=millimols
NTCP=Na+taurocholate cotransporting polypeptide
PBS=phosphate buffered saline
py=pyridine
TEOC-Cl=trimethylsilylethyl chloroformate
THF=tetrahydrofuran
TFA=trifluoroacetic acid
TMS=trimethylsilyl
μL microliter
μM=micromolar
v/v=volume to volume

EXPERIMENTAL METHODS

The following examples illustrate how the synthesis of drug/linker/transporter conjugates could be conducted in order to prepare compounds of formula (I), (II) and (III). The syntheses described below are illustrated in FIGS. 8-22.

EXAMPLE 1

Synthesis of Compound (2)

Following the method of Kramer[14], methanesulfonyl chloride (0.24 mol) is added dropwise at 0° C. to cholic acid (1) (0.2 mol) in 400 mL of pyridine. The mixture is stirred for 30 min at 0° C. then 2 h at room temperature. The mixture is poured into 2.5 L of 10% aqueous sulfuric acid and extracted with ethyl acetate. The combined organic phases are dried over $MgSO_4$ and evaporated to dryness. The residue is chromatographed on silica gel to give the 3-mesylate (2).

EXAMPLE 2

Synthesis of Compound (3)

For n=2:

Following the method of Kramer[14], Compound 2 (0.2 mol) is heated at 100° C. for 2 h in a mixture of ethylene glycol (400 niL) and pyridine (80 mL). The mixture is poured into 1.2 L of 10% aqueous sulfuric acid and extracted with ethyl acetate. The combined organic phases are dried over $MgSO_4$ and evaporated to dryness. The product is converted to its silyl ester derivative without further purification as described below.

Other 3β-substituted ether derivatives:

Similar compounds are prepared from other α,ω-diols according to the same method (e.g. from 1,3-propanediol, ethylene glycol).

EXAMPLE 3

Synthesis of Compound (5)

Following the method described in Batta[4], diethylazodicarboxylate (0.7 mol) is dissolved in anhydrous benzene (90 mL) and added slowly to a solution of methyl cholate (4) (0.2 mol) and PPh3 (0.7 mol) in benzene (900 mL) containing 98% formic acid (35 mL). The solution is heated under reflux for 48 h then cooled to room temperature whereupon a white solid crystallizes out. The solid is filtered off, washed with a small amount of benzene and the combined mother liquors concentrated to give a yellow solid. This solid is dissolved in anhydrous ether (500 mL) and poured into hexane (3.5 L). The resulting white solid is again filtered off and the mother liquors concentrated to dryness. The residue is dissolved in 5% methanolic KOH (1.5 L) and heated under reflux for 3 h. Water (1.5 L) is added and the mixture concentrated to half its volume under reduced pressure at 40° C. The solution is cooled on ice and acidified with dilute HCl. The resulting white solid is collected, washed with water and dried in vacuo. The product is crystallized from a mixture of chloroform-methanol.

EXAMPLE 4

Synthesis of Compound (6)

3β-Substituted ether compounds (6) are prepared from (5) and α,ω-diols as described for compound (3) above.

EXAMPLE 5

Synthesis of Compounds (7) and (8)

Compounds (7) and (8) are prepared from compounds (3) and (6) respectively. The starting material (0.15 mol) is stirred with tert-butyldimethylsilyl chloride (0.33 mol) and DMAP (0.33 mol) in dry dichloromethane (500 mL) at room temperature for 4 h. The solvent is removed by evaporation in vacuo and the residue warmed to 50° C. for 2 h in a mixture of methanol (900 mL) and water (100 mL). The solvent is concentrated again in vacuo to a volume of 100 mL and water (400 mL) added. The pH of the resulting solution is adjusted to 2 by addition of HCl. The white suspension is extracted with ethyl acetate and the combined organic phases dried over $MgSO_4$ and evaporated to dryness. The product is sufficiently pure to be used as is in the next step.

EXAMPLE 6

Synthesis of Compounds (9) and (10)

Compounds (9) and (10) are prepared from compounds (7) and (8) respectively following the method of Kramer[14]. The starting material (25 mmol) is dissolved in dry THF (250 mL) and a mixture of $NEt_3$ (75 mmol) and 2,6-dichlorobenzoyl chloride (30 mmol) is added dropwise at room temperature, before heating under reflux for 3 h. The resulting anhydride solution is cooled to 10° C. and tert-butanol (35 mmol) and DMAP (25 mmol) are added successively. The mixture is warmed to its boiling point over 1 h and then heated under reflux for 4 h. The mixture is cooled and then the THF removed via evaporation in vacuo. The residue is taken up in ethyl acetate and the solution thoroughly washed with water, dried over $MgSO_4$ and evaporated to dryness. Column chromatography on silica gel gives the tert-butyl ester products as white crystalline solids.

EXAMPLE 7

Synthesis of Compounds (11) and (12)

Compounds (11) and (12) are prepared from compounds (7) and (8) respectively via dissolution of the starting material (0.1 mol) in DMF (200 mL) and addition of diisopropylcarbodiimide (0.1 mol). After stirring for 20 min, glycine tert-butyl ester (0.1 mol) in DMF (100 mL) is added and the mixture stirred for 2 h at room temperature. The solution is concentrated in vacuo to a volume of ~50 mL, poured into ice-cold water (400 mL) and the pH adjusted to ~3 with HCl. The resulting white suspension is extracted thoroughly with ethyl acetate, the combined organic phases dried over $MgSO_4$ and evaporated to dryness. Column chromatography on silica gel gives the glycine tert-butyl ester conjugates.

EXAMPLE 8

Synthesis of Compounds (13)–(16)

Compounds (13)-(16) are prepared from compounds (9)-(12) respectively. The silyl ester starting materials (50 mmol) are dissolved in THF (200 mL) and treated with tetrabutylammonium fluoride (55 mmol) for 1 h. The reaction mixtures are poured into water and the resulting white suspensions thoroughly extracted with ethyl acetate. The combined organic phases are dried over MgSO$_4$ and evaporated to dryness. The resulting alcohol products are used without further purification.

EXAMPLE 9

Synthesis of Compounds (17)–(20)

Compounds (13)–(16) are prepared from compounds (9)–(12) respectively following the methods of Kramer[14]. The silyl ester starting materials (50 mmol) and DMAP (125 mmol) are dissolved in dry pyridine (300 mL) and treated dropwise with acetic anhydride (125 mmol) at 0° C. The reaction mixtures are stirred at room temperature for 4 h, then poured into water and extracted thoroughly with ethyl acetate. The combined organic phases are washed with saturated aqueous NaHCO$_3$ solution and dried over MgSO$_4$. The resulting crude diacetates are dissolved in THF (200 mL) and treated with tetrabutylammonium fluoride (55 mmol) for 1 h. The reaction mixtures are poured into water and the resulting white suspensions thoroughly extracted with ethyl acetate. The combined organic phases are dried over MgSO$_4$ and evaporated to dryness. The residues are dissolved in dry DMF (500 mL) and treated with pyridinium dichromate (50 mmol) for 24 h at room temperature. The reaction mixtures are poured into water and thoroughly extracted with diethyl ether. The combined organic phases are dried over MgSO$_4$ and evaporated to dryness. The residues are chromatographed on silica gel to afford the corresponding carboxylic acid products. The resulting diacetates are hydrolyzed via dissolution in 50% methanolic KOH (400 mL) at 50° C. for 2 h. Water (400 mL) is added and the mixtures concentrated to half their volume under reduced pressure at 40° C. The solutions are cooled on ice and acidified with dilute HCl. The resulting white suspensions are thoroughly extracted with ethyl acetate, the combined organic phases are dried over MgSO$_4$ and evaporated to dryness.

EXAMPLE 10

Synthesis of Compounds (21)–(24)

Compounds (21)–(24) are prepared from compounds (13)–(16) respectively. Methanesulfonyl chloride (30 mmol) is added dropwise at 0° C. to solutions of the starting alcohols (25 mmol) in 30 mL of pyridine. The mixtures are stirred for 30 min at 0° C. then 2 h at room temperature. The mixtures are poured into water, extracted thoroughly with ethyl acetate and the combined organic phases dried over MgSO$_4$. The resulting crude mesylates are dissolved in acetonitrile (200 mL) and treated with methylamine (150 mmol) at 40° C. for 2 h. Solvent is removed in vacuo and the residues are chromatographed on silica gel (eluting with EtOAc/MeOH/NEt$_3$) to afford the N-methylaminoalkyl ethers (21)–(24).

EXAMPLE 11

Synthesis of Compound (27)

The N-benzyloxycarbonylamidino compound (25), a precursor of the thrombin inhibitor melagatran, is prepared according to the method of Antonsson[2]. Compound (25) (10 mmol) is suspended in dry dichloromethane (100 mL), N,O-bis(trimethylsilyl)acetamide (15 mmol) is added and the mixture heated under reflux for 1 h to give a clear solution. This mixture is cooled to room temperature and N-(benzyloxy-carbonyloxy)succinimide (12 mmol) is added. After stirring for 3 h, the solution is poured into water, the mixture acidified with HCl to pH ~2, and then thoroughly extracted with ethyl acetate. The combined organic phases are dried over MgSO$_4$ and evaporated to dryness to yield compound (27).

EXAMPLE 12

Synthesis of Compounds (28)–(31)

The iodomethyl carbonates (28)–(31) are prepared from alcohols (13)–(16) respectively following the methods of Johansson[8]. Chloromethyl chloroformate (50 mmol) is added to a solution of the starting alcohol (25 mmol) and dry pyridine (20 mL) in dry dichloromethane (150 mL) at 0° C. After stirring for 1 h, the mixture is diluted with an equal volume of dichloromethane and washed successively with water, saturated aqueous NaHCO$_3$ and brine. The organic phase is dried over anhydrous Na$_2$SO$_4$ and concentrated, coevaporating several times with toluene to effect complete removal of water. Column chromatography on silica gel affords the intermediate chloromethyl carbonate compounds. These products are then dissolved in dry acetonitrile (250 mL) and treated with NaI (100 mmol) at 80° C. for 3 h. After removal of the solvent in vacuo, the residue is partitioned between ethyl acetate (200 mL) and water (100 mL). The organic phase is washed with 5% aqueous sodium thiosulfate, and then brine, dried over anhydrous Na$_2$SO$_4$ and concentrated. Column chromatography on silica gel affords the desired iodomethyl carbonates (28)–(31).

EXAMPLE 13

Synthesis of Compounds (32)–(35)

The iodomethyl esters (32)–(35) are prepared from acids (17)–(20) by an adaptation of the method of Johansson[8]. The acids (25 mmol) are dissolved in dry dichloromethane (300 mL) and treated with N,O-bis(trimethylsilyl)-acetamide (150 mmol) under reflux for 2 h. The solvent is removed by evaporation in vacuo and the residues redissolved in methanol (500 mL) and stirred for 2 h. The solvent is concentrated again in vacuo to a volume of ~200 mL and 40% aqueous tetrabutylammonium hydroxide solution (25 mmol) added. The solutions are dried in vacuo and coevaporated with toluene several times to azeotropically remove water. The residues are dissolved in dry dichloromethane (100 mL) and chloroiodomethane (250 mmol) is added and the mixture stirred at room temperature for 18 h. After removing the solvent in vacuo, the chloromethyl ester intermediates are isolated by chromatography on silica gel. These products are then dissolved in dry acetonitrile (250 mL) and treated with NaI (100 mmol) at 70° C. for 3 h. The reaction mixtures are filtered and the filtrates dried in vacuo. The resulting crude iodomethyl esters (32)–(35) are used as is to prepare prodrug derivatives as described below.

EXAMPLE 14

Synthesis of Compounds (36) and (37)

Compounds (36) and (37) are prepared from compounds (1) and (5) respectively. The starting materials (50 mmol) are dissolved in dry THF (500 mL) and a mixture of NEt3 (100 mmol) and 2,6-dichlorobenzoyl chloride (60 mmol) are added dropwise at room temperature, before heating under reflux for 3 h. The resulting anhydride solutions are cooled to 10° C. and tert-butanol (70 mmol) and DMAP (50 mmol) are added successively. The mixtures are warmed to boiling over 1 h and then heated under reflux for 4 h. The mixtures are cooled and then the THF removed via evaporation in vacuo. The residues are taken up in ethyl acetate and the solutions thoroughly washed with water, dried over $MgSO_4$ and evaporated to dryness. Column chromatography on silica gel gives the tert-butyl ester products as white crystalline solids.

EXAMPLE 15

Synthesis of Compounds (38) and (39)

Compounds (38) and (39) are prepared from compounds (36) and (37) respectively. The starting materials (30 mmol) are dissolved in dry acetonitrile (150 mL) together with DMAP (30 nunol). Solutions of bromoacetic anhydride (35 mmol) in acetonitrile are added dropwise and the reaction mixtures stirred for 4 h at room temperature. The solvent is removed in vacuo, the residues redissolved in ethyl acetate and washed thoroughly with a 0.2 M aqueous solution of $KHSO_4$. The organic phases are dried over $MgSO_4$ and evaporated to dryness to afford the crude bromoacetates, which are used as is in the subsequent step.

EXAMPLE 16

Synthesis of Compounds (40) and (41)

Compounds (40) and (41) are prepared from compounds (1) and (5) respectively. The starting materials (50 mmol) are dissolved in dry THF (500 mL) and a mixture of $NEt_3$ (100 mmol) and 2,6-dichlorobenzoyl chloride (60 mmol) are added dropwise at room temperature, before heating under reflux for 3 h. The resulting anhydride solutions are cooled to room temperature and glycine tert-butyl ester (60 mmol) and DMAP (60 mmol) are added successively. After stirring for 3 h at room temperature the THF is removed via evaporation in vacuo. The residues are taken up in ethyl acetate and the solutions thoroughly washed with water, dried over $MgSO_4$ and evaporated to dryness. Column chromatography on silica gel gives the glycinate ester products as white solids.

EXAMPLE 17

Synthesis of Compounds (42) and (43)

Compounds (42) and (43) are prepared from compounds (40) and (41) respectively. The starting materials (30 mmol) are dissolved in dry acetonitrile (150 mL) together with DMAP (30 mmol). Solutions of bromoacetic anhydride (35 mmol) in acetonitrile are added dropwise and the reaction mixtures stirred for 4 h at room temperature. The solvent is removed in vacuo, the residues redissolved in ethyl acetate and washed thoroughly with a 0.2 M aqueous solution of $KHSO_4$. The organic phases are dried over $MgSO_4$ and evaporated to dryness to afford the crude bromoacetates, which are used as is in the subsequent step.

EXAMPLE 18

Synthesis of Compounds (44)–(47)

Compounds (44), (45) and (46), (47) are prepared from compounds (38), (39) and (42), (43) respectively. Solutions of the starting bromoacetates (10 mmol) in dry DMSO (20 mL) are added dropwise to solutions of cyclohexylglycyl peptide (26) (10 mmol) and DMAP (10 mmol) in dry DMSO (20 mL). After stirring at room temperature for 4 h, the solvent is removed in vacuo. The residues are redissolved in ethyl acetate and washed thoroughly with a 0.2 M aqueous solution of $KHSO_4$. The organic phase is dried over $MgSO_4$ and chromatographed on silica gel to afford the pure protected peptidyl steroids. These are then treated with a mixture of dichloromethane (50 mL) and TFA (50 mL) for 1 h and the solvent removed in vacuo. The residues are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran esters as their hydrochloride salts.

EXAMPLE 19

Synthesis of Compounds (48)–(51)

Compounds (48)–(51) are prepared from compounds (13) –(16) respectively. The steroidal alcohol starting materials (10 mmol) and Cbz-protected melagatran (27) (10 mmol) dissolved in dry DMF (100 mL) are treated with diisopropylcarbodiimide (10 mmol) and DMAP (10 mmol) for 4 h at room temperature. The solvent is removed in vacuo, the residues redissolved in ethyl acetate and washed thoroughly with a 0.2 M aqueous solution of $KHSO_4$. The organic phase is dried over $MgSO_4$ and chromatographed on silica gel to afford the pure protected peptidyl steroids. These are then treated with a mixture of dichloromethane (50 mL) and TFA (50 mL) for 1 h and the solvent removed in vacuo. The residues are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran esters as their hydrochloride salts.

EXAMPLE 20

Synthesis of Compounds (52) and (53)

Compounds (52) and (53) are prepared from compounds (13) and (14) respectively. The steroidal alcohol starting materials (10 mmol) and Cbz-protected melagatran (27) (10 mmol) dissolved in dry DMF (100 mL) are treated with diisopropylcarbodiimide (10 mmol) and DMAP (10 mmol) for 4 h at room temperature. The solvent is removed in vacuo, the residues redissolved in ethyl acetate and washed thoroughly with a 0.2 M aqueous solution of $KHSO_4$. The organic phase is dried over $MgSO_4$ and chromatographed on silica gel to afford the pure protected peptidyl steroids. These are then treated with a mixture of dichloromethane (50 mL) and TFA (50 mL) for 1 h and the solvent removed in vacuo. The residues are dissolved in dry dioxane (100 mL) containing tri-n-butylamine (20 mmol), cooled to 0° C., and ethyl chloroformate (10 mmol) added dropwise. After stirring for 20 min solutions of taurine (20 mmol) in 2M aqueous NaOH (10 mL) are added dropwise and the mixtures warmed to room temperature with stirring for 2 h. The mixtures are poured into water (200 mL), neutralized with 1M aqueous HCl, and extracted thoroughly with ethyl acetate containing 5% (v/v) methanol. The organic layers are dried over MgSO$_4$ and chromatographed on silica gel to afford the pure Cbz-protected peptidyl taurocholates. These products are dissolved in a mixture of ethanol (250 mL) and 1M aqueous HCl (5 nmL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran taurocholate esters as their hydrochloride salts.

EXAMPLE 21

Synthesis of Compound (54)

Compound (27) (20 mmol) is dissolved in dioxane (100 mL) containing 2 M aqueous NaHCO$_3$ (10 mL). tert-Butyl bromoacetate (20 mmol) in dioxane (20 mL) is added dropwise and the mixture stirred at room temperature for 8 h. The mixture is concentrated to ~30 mL, poured into water (100 mL), and extracted thoroughly with ethyl acetate. The organic phase is dried over MgSO$_4$ and chromatographed on silica gel to afford pure protected melagatran tert-butyl acetate. This product is then treated with a mixture of dichloromethane (50 mL) and TFA (50 mL) for 1 h and the solvent removed in vacuo to afford compound (54).

EXAMPLE 22

Synthesis of Compounds (55)–(58)

Compounds (55)–(58) are prepared from compounds (21)–(24) respectively. The starting amines (10 mmol) and compound (54) (10 mmol) are dissolved in dry DMF (50 mL) and treated with diisopropylcarbodiimide (10 mmol) for 2 h at room temperature. The solvent is removed in vacuo, the residues redissolved in ethyl acetate and washed thoroughly with a 0.2 M aqueous solution of KHSO$_4$. The organic phase is dried over MgSO$_4$ and chromatographed on silica gel to afford the protected peptidyl steroids. These are then treated with a mixture of dichloromethane (50 mL) and TFA (50 mL) for 1 h, and the solvent removed in vacuo. The residues are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran glycolamide esters as their hydrochloride salts.

EXAMPLE 23

Synthesis of Compounds (59) and (60)

Compounds (59) and (60) are prepared from compounds (21) and (22) respectively. The starting amines (10 mmol) and (54) (10 mmol) are dissolved in dry DMF (50 11L) and treated with diisopropylcarbodiimide (10 mmol) for 2 h at room temperature. The solvent is removed in vacuo, the residues redissolved in ethyl acetate and washed thoroughly with a 0.2 M aqueous solution of KHSO$_4$. The organic phase is dried over MgSO$_4$ and chromatographed on silica gel to afford the pure protected peptidyl steroids. These are then treated with a mixture of dichloromethane (50 mL) and TFA (50 mL) for 1 h, and the solvent removed in vacuo. The residues are dissolved in dry dioxane (100 mL) containing tri-n-butylamine (20 mmol), cooled to 0C, and ethyl chloroformate (10 mmol) added dropwise. After stirring for 20 min solutions of taurine (20 mmol) in 2M aqueous NaOH (10 mL) are added dropwise and the mixtures warmed to room temperature with stirring for 2 h. The mixtures are poured into water (200 mL), neutralized with 1M aqueous HCl, and extracted thoroughly with ethyl acetate containing 5% (v/v) methanol. The organic layers are dried over MgSO$_4$ and chromatographed on silica gel to afford the pure Cbz-protected peptidyl taurocholates. These products are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran taurocholate glycolamide esters as their hydrochloride salts.

EXAMPLE 24

Synthesis of Compounds (61)–(64)

Compounds (61)–(64) are prepared from compounds (28)–(31) respectively. Cbz-protected peptide (27) (10 mmol) is dissolved in THF (100 mL) and treated with 40% aqueous tetrabutylammonium hydroxide solution (10 mmol). The solvent is removed in vacuo and the residue coevaporated with toluene several times to azeotropically remove water. The residue is reacted with iodomethyl carbonates (28)–(31) (10 mmol) in dry DMF under argon and the mixtures stirred at room temperature for 24 h. After removing the solvent in vacuo, the products are purified by chromatography on silica gel. These are then treated with a mixture of dichloromethane (80 mL) and TFA (20 mL) for 1 h, and the solvent removed in vacuo. The residues are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran carbonate prodrugs.

EXAMPLE 25

Synthesis of Compounds (65) and (66)

Compounds (65) and (66) are prepared from compounds (28) and (29) respectively. Cbz-protected peptide (27) (10 mmol) is dissolved in THF (100 mL) and treated with 40% aqueous tetrabutylammonium hydroxide solution (10 mmol). The solvent is removed in vacuo and the residue coevaporated with toluene several times to azeotropically remove water. The residue is reacted with iodomethyl carbonates (28) and (29) (10 mmol) in dry DMF under argon and the mixture stirred at room temperature for 24 h. After removing the solvent in vacuo, the products are purified by chromatography on silica gel. These are then treated with a mixture of dichloromethane (80 mL) and TFA (20 mL) for 1 h, and the solvent removed in vacuo. The residues are dissolved in dry dioxane (100 mL) containing tri-n-butylamine (20 mmol), cooled to 0° C., and ethyl chloroformate (10 mmol) added dropwise. After stirring for 20 min solutions of taurine (20 mmol) in 2 M aqueous NaOH (10 mL) are added dropwise and the mixtures warmed to room temperature with stirring for 2 h. The mixtures are poured into water (200 mL), neutralized with 1M aqueous HCl, and extracted thoroughly with ethyl acetate containing 5% (v/v) methanol. The organic layers are dried over MgSO$_4$ and chromatographed on silica gel to afford the Cbz-protected peptidyl taurocholates. These products are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran taurocholate carbonate prodrugs.

EXAMPLE 26

Synthesis of Compounds (67)–(70)

Compounds (67)–(70) are prepared from compounds (32)–(35) respectively. Cbz-protected peptide (27) (10 mmol) is dissolved in THF (100 mL) and treated with 40% aqueous tetrabutylammonium hydroxide solution (10 mmol). The solvent is removed in vacuo and the residue coevaporated with toluene several times to azeotropically remove water. The residue is reacted with iodomethyl esters (32)–(35) (10 mmol) in dry DMF under argon and the mixture stirred at room temperature for 24 h. After removing the solvent in vacuo, the products are purified by chromatography on silica gel. These are then treated with a mixture of dichloromethane (80 mL) and TFA (20 mL) for 1 h, and the solvent removed in vacuo. The residues are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran acyloxyester prodrugs.

EXAMPLE 27

Synthesis of Compounds (71) and (72)

Compounds (71) and (72) are prepared from compounds (32) and (33) respectively. Cbz-protected peptide (27) (10 mmol) is dissolved in THF (100 mL) and treated with 40% aqueous tetrabutylammonium hydroxide solution (10 mmol). The solvent is removed in vacuo and the residue coevaporated with toluene several times to azeotropically remove water. The residue is reacted with iodomethyl esters (32) and (33) (10 mmol) in dry DMF under argon and the mixture stirred at room temperature for 24 h. After removing the solvent in vacuo, the products are purified by chromatography on silica gel. These are then treated with a mixture of dichloromethane (80 mL) and TFA (20 mL) for 1 h, and the solvent removed in vacuo. The residues are dissolved in dry dioxane (100 mL) containing tri-n-butylamine (20 mmol), cooled to 0° C., and ethyl chloroformate (10 mmol) added dropwise. After stirring for 20 min solutions of taurine (20 mmol) in 2 M aqueous NaOH (10 mL) are added dropwise and the mixtures warmed to room temperature with stirring for 2 h. The mixtures are poured into water (200 mL), neutralized with 1M aqueous HCl, and extracted thoroughly with ethyl acetate containing 5% (v/v) methanol. The organic layers are dried over MgSO₄ and chromatographed on silica gel to afford the CBz-protected peptidyl taurocholates. These products are dissolved in a mixture of ethanol (250 mL) and 1M aqueous HCl (5 mL) and stirred with 5% Pd/C (3.0 g) under 1 atm hydrogen gas for 2 h. The mixtures are filtered, propylene oxide (10 mL) added, and the solutions stirred at 40° C. for 2 h. The solvent is removed in vacuo to give the melagatran taurocholate acyloxyester prodrugs.

EXAMPLE 28

Synthesis of Compound (74)

Diethylazodicarboxylate (0.7 mol) is dissolved in anhydrous benzene (90 mL) and added slowly to a solution of methyl chenodeoxycholate (73) (0.2 mol) and PPh3 (0.7 mol) in benzene (900 mL) containing 98% formic acid (35 mL). The solution is heated under reflux for 48 h then cooled to room temperature whereupon a white solid crystallizes out. The solid is filtered off, washed with a small amount of benzene and the combined mother liquors concentrated to give a yellow solid. This solid is dissolved in anhydrous ether (500 mL) and poured into hexane (3.5 L). The resulting white solid is again filtered off and the mother liquors concentrated to dryness. The residue is dissolved in 5% methanolic KOH (1.5 L) and heated under reflux for 3 h. Water (1.5 L) is added and the mixture concentrated to half its volume under reduced pressure at 40° C. The solution is cooled on ice and acidified with dilute HCl. The resulting white solid is collected, washed with water and dried in vacuo. The product is crystallized from a mixture of chloroform-methanol.

EXAMPLE 29

Synthesis of Compounds (75) and (76)

Compounds (75) and (76) are prepared from chenodeoxycholic acid and compound (74) respectively via dissolution of the starting materials (0.2 mol) in DMF (400 mL) and addition of diisopropylcarbodiimnide (0.2 mol). After stirring for 20 min, glycine benzyl ester (0.2 mol) in DMF (200 mL) is added and the mixtures stirred for 2 h at room temperature. The solutions are concentrated in vacuo to a volume of ~100 mL, poured into ice-cold water (500 mL) and the pH adjusted to ~3 with HCl. The resulting white suspensions are extracted thoroughly with ethyl acetate, the combined organic phases dried over MgSO₄ and evaporated to dryness. Column chromatography on silica gel gives the glycine benzyl ester conjugates as white waxy solids.

EXAMPLE 30

Synthesis of Compounds (77) and (78)

Compounds (77) and (78) are prepared from compounds (75) and (76) respectively following the method of Anelli[1]. Triphenylphosphine (0.1 mol) and diethylazodicarboxylate (0.1 mol) are added to solutions of the starting material (0.1 mol) in THF (1 L), then solutions of diphenylphosphoryl azide (0.1 mol) in THF (100 mL) are added dropwise over 30 min. After 24 h at room temperature more triphenylphosphine (0.05 mol) and diethylazodicarboxylate (0.05 mol) are added. After a further 5 h triphenylphosphine (0.1 mol) and water (50 mL) are added and the mixtures stirred for 4 days at room temperature. The solvent is removed in vacuo and the residues dissolved in ethyl acetate, dried over Na₂SO₄ and chromatographed on silica gel to give the 3-amino steroid products.

EXAMPLE 31

Synthesis of Compounds (79) and (80)

Compounds (79) and (80) are prepared from compounds (77) and (78) respectively by treatment of the starting material (50 mmol) in dry DMF (200 mL) with diglycolic anhydride (50 mmol) for 2 h at room temperature. The solvent is removed in vacuo and the residues chromatographed on silica gel to afford the carboxylic acid products.

EXAMPLE 32

Synthesis of Compounds (81) and (82)

Compounds (81) and (82) are prepared from compounds (75) and (76) respectively following the method of Anellil. The starting steroids (50 mmol) are heated under reflux in a mixture of carbon tetrachloride (75 mL) and pyridine (75 mL) with succinic anhydride (50 mmol) for 3 h. The solvent is removed in vacuo and the residues taken up in ethyl acetate, washed with 0.2 M aqueous $KHSO_4$, dried over $Na_2SO_4$ then chromatographed on silica gel to give the hemisuccinate products.

EXAMPLE 33

Synthesis of Compound (84)

1-[(Benzyloxy)carbonyl]-4-(tert-butoxy)pyrrolidine-2-carboxylic acid (83) (0.2 mol, Bachem) is dissolved in dry DMF (500 mL) and treated with diisopropylcarbodiimide (0.2 mol) for 20 min. Dimethylamine (0.22 mol) is added and the solution stirred for 2 h at room temperature. After removing the solvent in vacuo, the residue is chromatographed on silica gel to afford the pure dimethylamide in quantitative yield. This product is dissolved in ethanol (500 mL) and stirred with 5% Pd/C (10 g) under 1 atm hydrogen gas for 4 h. The solvent is removed in vacuo, the residue redissolved in dry DMF with triethylamine (0.2 mol) and allyl chloroformate (0.2 mol) added slowly with stirring. After 2 h at room temperature, the solvent is removed in vacuo, the residue redissolved in ethyl acetate, washed with 0.2 M aqueous $KHSO_4$, dried over $Na_2SO_4$ and evaporated to dryness. The residue is taken up in dichloromethane (100 mL) and treated for 2 h with TFA (100 mL). After removing the solvent in vacuo, the residue is chromatographed on silica gel to give hydroxyproline derivative (84).

EXAMPLE 34

Synthesis of Compound (85)

Methanesulfonyl chloride (0.12 mol) is added dropwise at 0° C. to compound (84) (0.1 mol) in 200 mL of pyridine. The mixture is stirred for 30 min at 0° C. then 2 h at room temperature. The mixture is poured into 2.5 L of 10% aqueous sulfuric acid and extracted with ethyl acetate. The combined organic phases are dried over $Na_2SO_4$ and evaporated to dryness. The crude mesylate is dissolved in DMF (200 mL), potassium thioacetate (0.12 mol) added and the mixture stirred for 6 h at room temperature. After removing the solvent in vacuo, the residue is taken up in ethyl acetate, washed with water, dried over $Na_2SO_4$ and then chromatographed on silica gel to give the thioacetate intermediate. This product is dissolved in methanol and treated with 4 equivalents of methanolic ammonia for 2 h at room temperature. Removal of the solvent in vacuo affords the thiol compound (85).

EXAMPLE 35

Synthesis of Compound (87)

Compound (86) (50 mmol, Kaneka) is dissolved in dry acetonitrile (200 mL) containing diisopropylethylamine (50 mmol) and thiol (85) (50 mmol) added dropwise under argon. After stirring for 12 h at room temperature, the solution is concentrated to ~50 mL and the carbapenem product isolated after flash chromatography on a short silica gel column.

EXAMPLE 36

Synthesis of Compound (88)

To a solution of compound (87) (25 mmol) and palladium tetrakis(triphenylphosphine) (5 mmol) in THF (100 mL) under argon is added tri-n-butyltin hydride (30 mmol) and the mixture stirred at room temperature for 2 h. After removing the solvent in vacuo, the residue is redissolved in ethyl acetate, washed with saturated aqueous $NaHCO_3$, dried over $Na_2SO_4$ and passed through a short silica gel column, eluting with ethyl acetate/methanol. The solvent is removed in vacuo then chloromethyl chloroformate (30 mmol) and dry pyridine (20 mL) are added dropwise to a solution of the residue in dry dichloromethane (150 mL) at 0° C. After stirring for 1 h, the mixture is diluted with an equal volume of dichloromethane and washed successively with water, saturated aqueous $NaHCO_3$ and brine. The organic phase is dried over anhydrous $Na_2SO_4$ and concentrated, coevaporating several times with toluene to effect complete removal of water. Column chromatography on silica gel affords the intermediate chloromethyl carbamate compound. This product is then dissolved in dry acetonitrile (250 mL) and treated with NaI (100 mmol) at 50° C. for 3 h. After removal of the solvent in vacuo, the residue is partitioned between ethyl acetate (200 mL) and water (100 mL). The organic phase is washed with 5% aqueous sodium thiosulfate, and then brine, dried over anhydrous $Na_2SO_4$ and concentrated. Column chromaography on silica gel affords the desired iodomethyl carbamate (88).

EXAMPLE 37

Synthesis of Compounds (89)–(92)

Compounds (89)–(92) are prepared from compounds (79)–(82) respectively. The steroidal carboxylic acids (10 mmol) are dissolved in THF (100 mL) and treated with 40% aqueous tetrabutylammonium hydroxide solution (10 mmol). The solvent is removed in vacuo and the residues coevaporated with toluene several times to azeotropically remove water. The residues are reacted with iodomethyl carbamate (88) (10 mmol) in dry DMF under argon and the mixtures stirred at room temperature for 24 h. After removing the solvent in vacuo, the products are purified by chromatography on silica gel. The products are dissolved in ethanol (250 mL) and stirred with 5% Pd/C (3.0 g) under 1 atm hydrogen gas for 2 h. The mixtures are filtered and the solvent is removed in vacuo to give the meropenem acyloxycarbamate prodrugs.

EXAMPLE 38

Synthesis of Compound (93)

Compound (87) (25 mmol) is dissolved in ethanol (250 mL) and stirred with 5% Pd/C (6.0 g) under 1 atm hydrogen gas for 2 h. The mixture is filtered and the solvent is removed in vacuo. The residue is dissolved in THF (100 mL) and treated with 40% aqueous tetrabutylammonium hydroxide solution (25 mmol). The solvent is removed in vacuo and the residues coevaporated with toluene several times to azeotropically remove water. The residue is dissolved in dry dichloromethane (100 mL) and chloroiodomethane (250 mmol) is added and the mixture stirred at room temperature for 18 h. After removing the solvent in vacuo, the chloromethyl ester intermediate is isolated by chromatography on silica gel. This product is then dissolved in dry acetonitrile (250 mL) and treated with NaI (100 mmol) at 70° C. for 3 h. The reaction mixture is filtered and the filtrate dried in vacuo. The resulting crude iodomethyl ester (93) is used as is to prepare prodrug derivatives described below.

EXAMPLE 39

Synthesis of Compounds (94)–(97)

Compounds (94)–(97) are prepared from compounds (79)–(82) respectively. The steroidal carboxylic acids (10 mmol) are dissolved in THF (100 mL) and treated with 40% aqueous tetrabutylammonium hydroxide solution (10 mmol). The solvent is removed in vacuo and the residues coevaporated with toluene several times to azeotropically remove water. The residues are reacted with iodomethyl ester (93) (10 mmol) in dry DMF under argon and the mixtures stirred at room temperature for 24 h. After removing the solvent in vacuo, the products are purified by chromatography on silica gel. Solutions of these products and palladium tetrakis(triphenylphosphine) (2.5 mmol) in THF (100 mL) under argon are treated with tri-n-butyltin hydride (15 mmol) and the mixtures stirred at room temperature for 2 h. After removing the solvent in vacuo, the residues are redissolved in ethyl acetate, washed with saturated aqueous NaHCO$_3$, dried over Na$_2$SO$_4$ and passed through a short silica gel column, eluting with ethyl acetate/methanol. The solvent is removed in vacuo and the residues redissolved in ethanol (250 mL) and stirred with 5% Pd/C (3.0 g) under 1 atm hydrogen gas for 2 h. The mixtures are filtered and the solvent is removed in vacuo to give the meropenem acyloxyester prodrugs.

EXAMPLE 40

Synthesis of Compound (99)

3—Oxo-deoxycholic acid (98) (50 mmol, Steraloids) is dissolved in dry dioxane (500 mL) containing tri-n-butylamine (100 mmol), cooled to 0° C., and ethyl chloroformate (50 mmol) added dropwise. After stirring for 20 min a solution of taurine (100 mmol) in 2 M aqueous NaOH (50 mL) is slowly added and the mixture warmed to room temperature with stirring for 2 h. The mixture is poured into water (1 L), neutralized with 1M aqueous HCl, and extracted thoroughly with ethyl acetate containing 5% (v/v) methanol. The organic layer is dried over MgSO$_4$ and chromatographed on silica gel to afford the 3-oxo-deoxytaurocholate (99).

EXAMPLE 41

Synthesis of Compound (101)

9-D-Arabinofuranosyl-2-fluoroadenine (100) (25 mmol, Fluka) is stirred in dry pyridine (100 mL) with dimethoxytrityl chloride for 8 h at room temperature. The solution is then cooled to 0° C., triethylsilyl chloride (60 mmol) is added and the mixture stirred at room temperature for 2 h. After removing the solvent in vacuo, the residue is dissolved in ethyl acetate, washed with water and the organic phase dried over MgSO$_4$. The solution is evaporated to dryness, the residue redissolved in dry DMF (100 mL) with DMAP (25 mmol) and a solution of TEOC-Cl (25 mmol) added dropwise over 10 min. After stirring for 4 h the solvent is removed in vacuo and the residue chromatographed on silica gel to afford the pure, fully protected nucleoside. This product is stirred in a mixture of acetic acid (50 mL) and dichloromethane (10 mL) for 2 h, the solvent removed in vacuo and the residue chromatographed on silica gel to afford the 5'-alcohol (101).

EXAMPLE 42

Synthesis of Compound (102)

Fmoc-aminoxyacetic acid (10 mmol) and diisopropylcarbodiimide (10 mmol) are stirred in dry DMF (30 mL) for 20 min and then added to a solution containing compound (101) (10 mmol) and DMAP (10 mmol) in dry DMF (30 mL). After stirring for 2 h the solvent is removed in vacuo and the residue treated with a 20% (v/v) solution of piperidine in DMF (30 mL) for 30 min. After removing the solvent in vacuo, the residue is chromatographed on silica gel to give alkoxyamine (102).

EXAMPLE 43

Synthesis of Compound (103)

3-Oxo-deoxytaurocholate (99) (10 mmol) and alkoxyamine (102) (10 mmol) are stirred for 1 h in THF (50 mL) at room temperature. After removing the solvent in vacuo, the residue is treated with tetrabutylammonium fluoride (25 mmol) in THF for 2 h. The solvent is removed again, the residue dissolved in a minimum volume of methanol and the product purified by chromatography on reverse-phase (C8) media, eluting with methanol/water/0.1% formic acid. The fludarabine oxime prodrug (103) is isolated after lyophilization.

EXAMPLE 44

Synthesis of Compound (104)

9β-D-Arabinofuranosyl-2-fluoroadenine (100) (25 mmol) is stirred in dry pyridine (100 mL) with TMSCl (100 mmol) at 0° C. for 1 h. Allyl-1-hydroxybenzotriazolyl carbonate (25 mmol) is added and the solution stirred at room temperature for 12 h. The solvent is removed in vacuo, 0.1 M HCl (100 mL) is added and the residue extracted with ethyl acetate, washed with water and the organic phase dried over MgSO$_4$. The residue is redissolved in dichloromethane (100 mL) and hydrogen fluoride-pyridine adduct (100 mmol) added. After stirring for 2 h at room temperature, the solvent is removed in vacuo, 0.1 M HCl (100 mL) is added and the residue extracted with ethyl acetate, washed with water and the organic phase dried over MgSO$_4$. The residue is chromatographed on silica gel to give the protected nucleoside (104).

EXAMPLE 45

Synthesis of Compound (106)

Cholic acid (1) (1 mmol) is dissolved in anhydrous THF (10 mL) and triethylamine (1.2 mmol) is added slowly with stirring. The solution is cooled to −5° C. in an ice-salt bath, and ethyl chloroformate (0.12 mL, 1.2 mmol) added slowly, maintaining the temperature between −5 to 0° C. After addition is completed, the cold mixture is stirred for an additional 15 minutes. A solution containing aspartic acid tert-butyl ester (1.75 mmol) in 2N NaOH (2 mL) is added and the mixture stirred for an additional 60 min at −5 to 0° C. After removal of the THF in vacuo, saturated NaHCO$_3$ (15 mL) is added and the aqueous mixture washed with EtOAc (3×10 mL), then the pH adjusted to ~3 with citric acid. The product is extracted into EtOAc (3×15 mL), and the combined organic phase dried over MgSO$_4$, and concentrated to dryness. The residue is purified by flash chromatography on silica gel (5% MeOH/CH$_2$Cl$_2$) to give the pure cholic acid adduct (105).

Compound (105) (0.5 mmol) is dissolved in dichloromethane (10 mL) and treated with DCC (0.55 mmol) and DMAP (0.1 mmol) with stirring for 15 min. (104) (0.5 mmol) is added and the mixture stirred at room temperature overnight. After filtration to remove the precipitated urea the solution is concentrated to dryness. The residue is acidified with aqueous HCl and extracted with ethyl acetate, washing with water and then the organic phase is dried over MgSO$_4$. The allyloxycarbonyl protecting group is removed from this crude product by dissolution in dichloromethane (10 mL) and treatment with Pd(PPh$_3$)$_4$ (0.1 mmol), formic acid (1 mmol) and n-butylamine (1 mmol) for 2 h. The solvent is removed in vacuo, 0.1 M HCl (20 mL) is added and the residue extracted with ethyl acetate, washed with water and the organic phase dried over MgSO$_4$. The residue is stirred in a 4.0 M solution of HCl in dioxane (10 mL) for 1 h and the solvent removed in vacuo. The desired fludarabine cholyl-aspartate ester (106) is purified by preparative HPLC.

EXAMPLE 46

Synthesis of Compound (108)

Compound (36) (4.06 g, 7.79 mmol) was heated under reflux with succinic anhydride (1.95 g, 19.5 mmol) in chloroform (60 mL) and pyridine (20 mL) for 3 hours. The solvent was removed in vacuo and the oily residue dissolved in ethyl acetate and washed with iN HCl, brine, then dried over sodium sulfate and concentrated to dryness affording (107) as a white solid (4.55 g, 94% yield). MS (ESI) m/z 620.41 (M−H⁻), 622.34 (M+H⁺).

$^1$H NMR (CDCl$_3$, 400 MHz, characteristic resonances only): 3.92 (d, 2H, J=5.6 Hz), 2.64–2.53 (m, 4H), 1.45 (s, 9H), 0.96 (d, 3H, J=6 Hz), 0.88 (s, 3H), 0.67 (s, 3H).

A solution of (107) (800mg, 1.29mmol) in ethanol (10 mL) was neutralized with a solution of 40% aqueous tetrabutylammonium hydroxide until pH~10. The solution was concentrated in vacuo to give the tetrabutylammonium salt, which was dissolved in BrCH$_2$Cl (15mL) and stirred in the dark at room temperature for 48 h. After removal of the excess BrCH$_2$Cl under reduced pressure, the residue was taken up in ethyl acetate and washed with water and brine. The organic layer was dried over sodium sulfate and concentrated in vacuo to give an oily residue. The residue was purified by flash chromatography on silica gel to give chloromethyl ester product (108) (375 mg, 44% yield).

MS (ESI) m/z 670.35 (M+H⁺).

$^1$H NMR (CDC13, 400 MHz, characteristic resonances only): 5.72 (s, 2H), 4.06 (d, 2H, J=5.2 Hz), 2.64–2.54 (m, 4H), 1.50 (s, 9H), 0.93 (d, 3H, J=6 Hz), 0.84 (s, 3H), 0.63 (s, 3H).

EXAMPLE 47

Synthesis of Compound (110)

Compound (108) (370 mg, 0.55 mmol) and sodium iodide (412 mg, 2.75 mmol) were dissolved in acetone (4 mL) and the mixture stirred at room temperature for 16 h. The mixture was filtered, and the filtrate is concentrated to an oil. The oil was dissolved in ethyl acetate (30 mL) and washed with 5% aqueous sodium thiosulfate, water and brine. After drying over sodium sulfate, concentration in vacuo yielded iodomethyl ester (109) as an oil (356mg, 85%). This material was used without further purification.

MS (ESI) m/z 762.40 (M+H⁺).

Compound (109) (356 mg, 0.47 mmol) was dissolved in DMF (5 mL) and cefinetazole sodium salt (136 mg, 0.27 mmol) and tetrabutylammonium hydrogensulfate (56 mg, 0.16 mmol) added. After stirring the mixture at 45° C. for 18 h, the solution was diluted with ethyl acetate (20 mL) and washed with water and brine. The organic layer was dried over sodium sulfate and concentrated in vacuo to give an oily residue. This material was used without further purification.

MS (ESI) m/z 1103.92 (M−H⁻), 1105.83(M+H⁺).

This oil was dissolved in a solution containing dichloromethane (2 mL) and TFA (2 mL). After stirring at room temperature for 1 h, the solvent was removed in vacuo. The oily residue was purified by preparative HPLC to afford the ceftnetazole acyloxyalkyl ester (110) as a white powder (24 mg, 9% yield).

MS (ESI) m/z 1047.92 (M−H⁻), 1049.93 (M+H⁺). $^1$H NMR (CD$_3$OD, 400 MHz, characteristic resonances only): 5.93 (d, 1H, J=6 Hz), 5.83 (d, 1H, J=5.6 Hz), 5.07 (s, 1H), 3.99 (s, 3H), 3.87 (s, 2H), 3.54 (s, 3H), 2.65–2.56 (m, 4H), 1.03 (d, 3H, J=6.8 Hz), 0.94 (s, 3H), 0.72 (s, 3H).

The $^1$H NMR. spectrum of (110) indicated the desired cefmetazole acyloxyalkyl ester (having the Δ3 alkene) was also contaminated with the double bond-migrated Δ2 product.

EXAMPLE 48

In Vitro Compound Transport Assays with IBAT and NTCP-Expressing Cell Lines (a) Inhibition of Radiolabeled Taurocholate Uptake CHO cells transfected with either the IBAT or NTCP transporter are seeded into 96-well microtiter plates at 100,000 cells/well in 100 liL DMEM containing 10% serum, glutamine and Penstrep. After overnight incubation the media is removed and test compound (25 μL) is added at 2× the final desired concentration. Tritiated taurocholate (50,000 CPM/well) is diluted with cold substrate to a final concentration of 5 μM and 25 μL/well of this mixture is added to the plate. After incubating for 1 h at room temperature the solution is removed and the plate washed 4× with PBS at 4° C. 200 μL/well of scintillant is added and the plate then read in a Wallac microbeta counter. The inhibition data is processed by standard methods to calculate an inhibition constant $K_1$ for the test compound.

(b) Trans-Stimulation of Substrate Efflux

The ability of test compounds (e.g., candidate drug/cleavable linker/transporter compounds) to serve as substrates for the IBAT or NTCP transporters is also determined by observing their trans-stimulation of tritiated taurocholate efflux from CHO cells expressing the respective transporter protein. The cells are seeded into 96-well microtiter plates at 100,000 cells/well in 100 μL DMEM containing 10% serum, glutamine and Penstrep. After overnight incubation the media is removed and the cells washed 2× with 100 μl/well HBSS. The cells are loaded with tritiated taurocholate (200,000 CPM/well diluted with cold substrate to a final concentration of 2 μM) in HBSS for 60 min then washed 6–8× with 100 μL/well HBSS. The wash solutions are removed by aspiration and solutions of the test compound in HBSS (120 μL/well) are added to the pre-loaded cells with a Cybi-Well robot. The efflux of labeled substrate is measured by removing 40 μL/well after 10 min. and 15 min and counting radioactivity on a Wallac microbeta counter. The residual radioactivity remaining in the cells is counted and efflux is normalized to the total amount of uptake (i.e. CPM efflux+CPM remaining in cells) to control for well-to-well variability in cell density. The efflux data is processed by standard methods to calculate the half-maximally effective dose ($EC_{50}$) for the test compound.

EXAMPLE 49

Standard Methods for Determination of Enzymatic Cleavage of Prodrugs in Vitro

Enhanced oral delivery of a drug molecule by attachment through a cleavable linker arm to an actively transported promoiety (transporter) requires that the drug eventually be released from the drug/cleavable linker/transporter compound (prodrug) by enzymatic cleavage in one or more tissues of the body. The stability of a novel prodrug is evaluated in one or more in vitro systems using tissues representative of those involved in the enterohepatic circulation (i.e., intestinal luminal contents, small intestinal cells, blood, liver, bile, etc.) following methods known in the art. Tissues may be obtained from any vertebrate species but most commonly are obtained from mouse, rat, hamster, guinea pig, rabbit, pig, dog, monkey or human sources. Fractions, homogenates, supernatants, extracts or other preparations of these tissues are obtained from suitable commercial sources (e.g., Pel-Freez Biologicals, Rogers, AR, or GenTest Corporation, Woburn, MA), or prepared by methods well known in the art. Representative conditions typically used for in vitro studies conducted with these preparations are described in the following table. For example, a prodrug (50 μM) is incubated with 90% human liver S9 fraction containing 1.3 mM NADPH or a suitable NADPH-generating system (e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4). The mixture is incubated at 37° C. for one hour. Aliquots (50 μL) are removed at 0, 30, and 60 min and quenched with 0.1% trifluoroacetic acid in acetonitrile. Samples are then centrifuged and analyzed by LC/MS. Similar conditions may be used with other homogenates, preparations or extracts of the tissues involved in the enterohepatic circulation. For drugs that are poorly absorbed, a preferred prodrug is one that demonstrates at least 1% cleavage to produce the free drug or an active metabolite thereof within a 60 minute period, when examined by one or more of methods III through XI as listed in Table 1. For drugs that are well absorbed, a preferred prodrug is one that demonstrates at least 1% cleavage to produce the free drug or an active metabolite thereof within a 60 minute period, when examined by any one or more of the methods listed in Table 1. Additional biological matrices are examined when considered relevant to the distribution of the drug. For example, stability in bile is examined for compounds known to be subject to biliary secretion. Stability of drug/cleavable linker/transporter compounds towards specific enzymes (e.g., carboxylesterases, cholinesterases, peptidases, etc.) is also assessed in vitro by incubation with the purified enzyme.

When the cefmetazole prodrug (110) was incubated with plasma or liver S9 samples from either rat or human sources according to the protocols in Table 1, the acyloxyalkyl ester compound was completely hydrolyzed within minutes, as assessed by LC-MS.

TABLE 1

Standard Conditions for In Vitro Evaluation of Prodrug Stability.

| Method | Tissue | Preparation | Tissue Prep Conctn | Prodrug Conctn. | Additional Cofactors | Incubation Condtn |
|---|---|---|---|---|---|---|
| I | Intestinal Luminal Contents | Intestinal Wash or Pancreatic Juice | 90% | 50M | None | 37° C. for 1 hr |
| II | Intestinal Luminal Contents | Purified Enzymes (eg: carboxypeptidase A) | 90% | 50 μM | None | 37° C. for 1 hr |
| III | Small Intestinal Cells | Cultured Enterocytes | N/A | 50 μM | None | 37° C. for 1 hr |
| IV | Small Intestinal Cells | S9 Fraction or Cytosol | 90% | 50 μM | NADPH or NADPH generating system* | 37° C. for 1 hr |
| V | Small Intestinal Cells | Microsomes | 0.8 mg protein/mL | 50 μM | NADPH or NADPH generating system* | 37° C. for 1 hr |

TABLE 1-continued

Standard Conditions for In Vitro Evaluation of Prodrug Stability.

| Method | Tissue | Preparation | Tissue Prep Conctn | Prodrug Conctn. | Additional Cofactors | Incubation Condtn |
|---|---|---|---|---|---|---|
| VI | Blood | Whole Blood, Plasma, Serum, etc. | 90% | 50 µM | None | 37° C. for 1 hr |
| VII | Liver | Cultured Hepatocytes | N/A | 50 µM | None | 37° C. for 1 hr |
| VIII | Liver | Precision Cut Liver Slices | N/A | 50 µM | None | 37° C. for 1 hr |
| IX | Liver | S9 Fraction or Cytosol | 90% | 50 µM | NADPH or NADPH generating system* | 37° C. for 1 hr |
| X | Liver | Microsomes | 0.8 mg protein/mL | 50 µM | NADPH or NADPH generating system* | 37° C. for 1 hr |
| XI | Liver | Purified Enzymes (e.g., porcine liver esterase) | 1.0 U/mL | 50 µM | Enzyme dependent | 37° C. for 1 hr |
| XII | Biliary Tract | Bile | 90% | 50 µM | None | 37° C. for 1 hr |

*NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4.

EXAMPLE 50

Determination of Oral Bioavailability of Parent Drug from Drug/Cleavable Linker/Transporter Compounds The oral bioavailability of the parent drug from the drug/cleavable linker/transporter compounds is assessed in animals by methods well known in the art. Typically, oral bioavailability is evaluated by comparison of the systemic exposure (area under the plasma or blood concentration versus time curve) for parent drug following a) oral administration of the novel drug/cleavable linker/transporter compound and b) intravenous administration of the parent drug. Typical species used for assessment of oral bioavailability include mouse, rat, guinea pig, rabbit, dog, primate, and human. Additional species may be examined where relevant to the therapeutic effect of the parent drug (e.g., woodchuck for compounds with antiviral activity against hepatitis B virus). In a typical bioavailability study, the parent drug is first administered intravenously to a group of animals/subjects in a suitable formulation at a dose sufficient to allow for determination of drug concentrations in blood, plasma or serum, and below the anticipated toxic dose. In a parallel study, the novel drug/cleavable linker/transporter compound is administered via oral gavage to an additional group of animals/subjects in a suitable formulation at a dose similar to that used for the free parent drug (based on equivalents of parent drug). Suitable formulations for intravenous administration include solutions, suspensions, etc. Suitable formulations for oral administration include solutions, suspensions, capsules, tablets, sustained delivery devices, etc. Following administration of each formulation, serial blood samples are collected from each animal/subject at intervals over a time course that may range from several minutes to several days. Blood samples are analyzed for concentrations of intact drug/cleavable linker/transporter compound, free parent drug, and any potential metabolites using suitable analytical methods. Systemic exposure to free parent drug (AUC) is calculated for each route of administration using standard methods. The percent oral bioavailability of the parent drug from the novel drug/cleavable linker/transporter compound is calculated as $$(AUC_{po}/AUC_{iv}) \times 100$$

where $AUC_{po}$ is the area under the concentration versus time curve for the free parent drug when administered orally as the drug/cleavable linker/transporter compound; $AUC_{iv}$ is the area under the concentration versus time curve for the free parent drug when administered intravenously as the parent drug.

The pharmacokinetics of the cefmetazole prodrug (110) is examined in rats. Three groups of four male Sprague-Dawley rats (approx 200 g) with jugular cannulae each received one of the following treatments: A) a single bolus intravenous injection of cefmetazole sodium salt (100 mg/kg, as a solution in water); B) a single oral dose of cefmetazole sodium salt (100 mg/kg, as a solution in water) administered by oral gavage; C) a single oral dose of (110) (210 mg/kg, as a solution in water) administered by oral gavage. Animals are fasted overnight prior to dosing and until 4 hours post-dosing. Serial blood samples are obtained over 24 hours following dosing and blood is processed for plasma by centrifugation. Plasma samples are stored at −80° C. until analyzed. Concentrations of cemetazole or (110) in plasma samples are determined by LC/MS/MS as described above. Plasma (50 µL) is precipitated by addition of 100 mL of methanol and supernatent is injected directly onto the LC/MS/MS system. Following oral administration of (110), intact (110) is undetecable in plasma at any time, but liberated cefmetazole (and its Δ2 isomer) is apparent within 30 min post dosing. The AUC for cefmetazole derived from (110) is greater than twice that observed when cefmetazole itself is administered orally to rats. These data indicate that prodrug (110) is metabolized to cefinetazole in vivo, and that a substantial improvement in oral absorption of cefmetazole is obtained when the bile acid derivative is administered.

EXAMPLE 51

Determination of Tissue Distribution, Metabolism, and Excretion of Parent Drug Following Administration of Novel Drug/Cleavable Linker/Transporter Compounds The fate of the novel drug/cleavable linker/transporter compounds and the released parent drug following oral administration in vivo is assessed in a suitable animal model. Typical species used include mouse, rat, guinea pig, rabbit, dog, primate, and human. Additional species may be examined where relevant to the therapeutic effect of the parent drug (e.g., woodchuck for compounds with antiviral activity against hepatitis B virus). In a typical tissue distribution, metabolism, or excretion study, the novel drug/cleavable linker/transporter compound is administered by oral gavage to a group of animals/subjects in a suitable formulation at a dose sufficient to allow for determination of drug/metabolite concentrations in tissues, and below the anticipated toxic dose. The drug/cleavable linker/transporter compound may be radiolabeled to allow calculation of drug recovery. Suitable formulations for oral administration include solutions, suspensions, capsules, tablets, sustained delivery devices, etc. Following administration of each formulation, serial blood samples are collected from each animal/subject at intervals over a time course that may range from several minutes to several days. Typically urine and feces are collected over the same period by use of metabolism cages. Where necessary, bile samples are collected from animals by cannulation of the common bile duct, using surgical methods well known in the art. Tissues are harvested from different groups of animals at suitable time points. Blood and tissue samples are analyzed for total radioactivity and for concentrations of intact drug/cleavable linker/transporter compound, free parent drug, and any potential metabolites using suitable analytical methods (such as LC/MS/MS).

What is claimed is:

1. A compound represented by the formula (x)

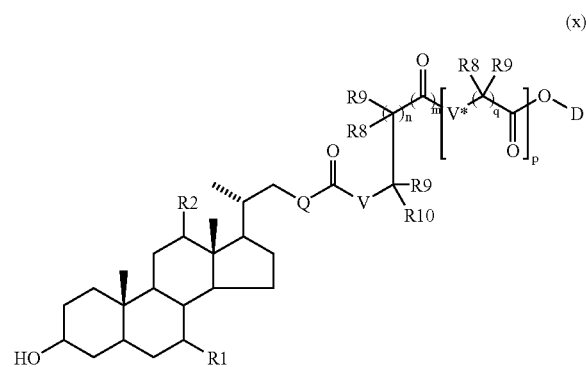

(x)

wherein:
R$^1$ is selected from the group consisting of hydrogen and OH;
R$^2$ is selected from the group consisting of hydrogen and OH;
—O—D is a drug containing at least one hydroxyl wherein O is derived from the hydroxyl moiety of the drug;
Q is CH$_2$ or O;
V and V* are independently NR$^7$, O, S or CR$^8$R$^9$;
R$^{10}$ is R$^8$ or (CR$^8$R$^9$)$_r$Z';
Z' is selected from the group consisting of CO$_2$H, SO$_3$H, OSO$_3$H, SO$_2$H, P(O)(OR$^6$)(OH), OP(O)(OR$^6$)(OH) and pharmaceutically acceptable salts thereof;
m is 0 or 1;
n is 0, 1, 2, 3 or 4;
p is 0, 1 or 2, providing that when m is 0 then p is not 0;
each q is independently 1, 2, 3 or 4;
r is 0 or 1;
R$^6$ is selected from the group consisting of alkyl, substituted alkyl, substituted aryl and substituted aryl;
each R$^7$, R$^8$ and R$^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or R$^8$ and R$^9$ together with the atoms to which they are attached form a cycloalkyl, substituted cycloalkyl, heterocycle or substituted heterocyclic ring, or, when R$^7$ and R$^9$ are present and attached to adjacent atoms, then R$^7$ and R$^9$ together with the atoms to which they are attached form a cycloalkyl, substituted cycloalkyl, heterocycle or substituted heterocyclic ring.

2. A compound represented by the formula (x)

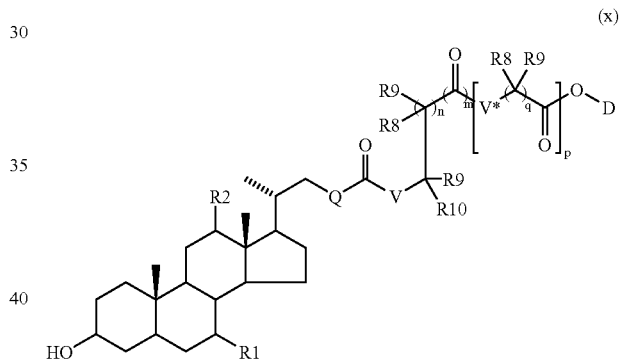

(x)

wherein:
R$^1$ is selected from the group consisting of hydrogen and OH;
R$^2$ is selected from the group consisting of hydrogen and OH;
—O—D is a drug containing at least one hydroxyl wherein O is derived from the hydroxyl moiety of the drug;
Q is CH$_2$;
V and V* are independently NR$^7$;
R$^{10}$ is R' or (CR$^8$R$^9$)$_r$Z';
Z' is selected from the group consisting of CO$_2$H, SO$_3$H, OSO$_3$H, SO$_2$H, P(O)(OR$^6$)(OH), OP(O)(OR$^6$)(OH) and pharmaceutically acceptable salts thereof;
m is 0 or 1;
n is 0, 1, 2, 3 or 4;
p is 0, 1 or 2;
each q is independently 1, 2, 3 or 4;
r is 0 or 1;
R$^6$ is selected from the group consisting of alkyl, substituted alkyl, aryl and substituted aryl;

each $R^7$, $R^8$ and $R^9$ is independently hydrogen, alkyl, substituted alkyl, alkenyl, substituted alkenyl, alkynyl, substituted alkynyl, cycloalkyl, substituted cycloalkyl, heterocycle, substituted heterocycle, aryl, substituted aryl, heteroaryl, substituted heteroaryl or $R^8$ and $R^9$ together with the atoms to which they are attached form a cycloalkyl, substituted cycloalkyl, heterocycle or substituted heterocyclic ring, or, when $R^7$ and $R^9$ are present and attached to adjacent atoms, then $R^7$ and $R^9$ together with the atoms to which they are attached form a cycloalkyl, substituted cycloalkyl, heterocycle or substituted heterocyclic ring.

3. A compound represented by the following formula

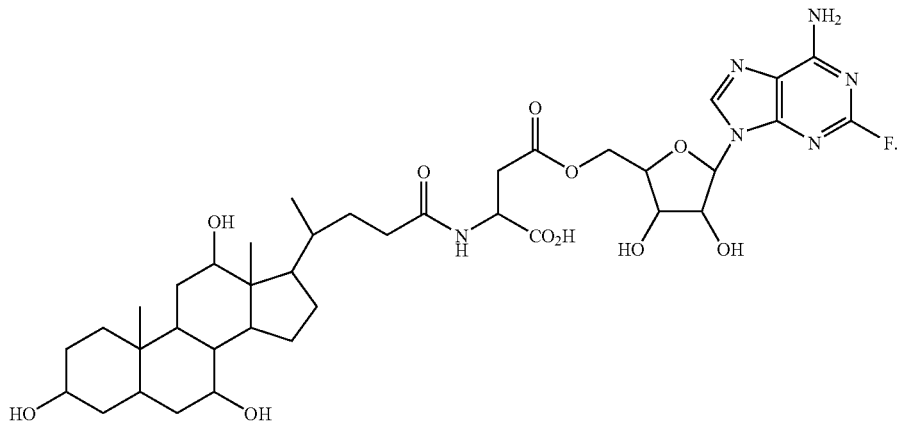

4. A pharmaceutical composititon comprising a pharmaceutically acceptable excipient and a compound according to any of claims 1, 2, and 3.

* * * * *